US011419713B2

(12) United States Patent
Kelly

(10) Patent No.: US 11,419,713 B2
(45) Date of Patent: *Aug. 23, 2022

(54) DEBRANCHING VISCERAL STENT GRAFT AND METHODS FOR USE

(71) Applicant: Sanford Health, Sioux Falls, SD (US)

(72) Inventor: Patrick W Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 470 days.

This patent is subject to a terminal disclaimer.

(21) Appl. No.: 16/424,214

(22) Filed: May 28, 2019

(65) Prior Publication Data

US 2019/0274813 A1 Sep. 12, 2019

Related U.S. Application Data

(63) Continuation of application No. 15/250,583, filed on Aug. 29, 2016, now Pat. No. 10,350,052, which is a
(Continued)

(51) Int. Cl.
*A61F 2/07* (2013.01)
*A61F 2/954* (2013.01)
(Continued)

(52) U.S. Cl.
CPC .............. *A61F 2/07* (2013.01); *A61F 2/954* (2013.01); *A61F 2/848* (2013.01); *A61F 2/852* (2013.01);
(Continued)

(58) Field of Classification Search
CPC .................. A61F 2/06–2002/007; A61F 2/954
See application file for complete search history.

(56) References Cited

U.S. PATENT DOCUMENTS

| 4,415,508 A | 11/1983 | Aida et al. |
| 5,489,295 A | 2/1996 | Piplani et al. |

(Continued)

FOREIGN PATENT DOCUMENTS

| CA | 2623977 | 7/1998 |
| CA | 2944014 | 8/2009 |

(Continued)

OTHER PUBLICATIONS

Examination Report from the Indian Intellectual Property Office for application No. 8047/CHENP/2014, dated Nov. 23, 2020.
(Continued)

*Primary Examiner* — Rebecca S Preston
(74) *Attorney, Agent, or Firm* — McDonnell Boehnen Hulbert & Berghoff LLP

(57) ABSTRACT

A visceral double-barreled main body stent graft and methods for its use, the stent graft comprises, a main body stent graft having distal and proximal ends, the main body stent graft's length ranges from about 100-120 mm and diameter at the proximal end ranges from about 30-45 mm, first and second lumens defined at the main body stent graft's distal end, the first lumen's diameter ranges from about 18-20 mm, the second lumen's diameter ranges from about 16-18 mm, the first and second lumens have about the same length from about 50-70 mm, the first lumen is secured to the second lumen along a shared length, and the main body stent graft defines a tubular wall that is contiguous with the first and second lumens such that any fluid entering the main body must exit through one of the first or second lumens.

18 Claims, 32 Drawing Sheets

Related U.S. Application Data continuation of application No. 14/625,517, filed on Feb. 18, 2015, now Pat. No. 9,427,308, which is a continuation of application No. 13/706,086, filed on Dec. 5, 2012, now Pat. No. 9,393,101.

(60) Provisional application No. 61/720,829, filed on Oct. 31, 2012, provisional application No. 61/720,846, filed on Oct. 31, 2012, provisional application No. 61/720,803, filed on Oct. 31, 2012, provisional application No. 61/716,315, filed on Oct. 19, 2012, provisional application No. 61/716,326, filed on Oct. 19, 2012, provisional application No. 61/716,292, filed on Oct. 19, 2012, provisional application No. 61/646,637, filed on May 14, 2012, provisional application No. 61/623,151, filed on Apr. 12, 2012.

(51) Int. Cl.
    *A61F 2/95* (2013.01)
    *A61F 2/82* (2013.01)
    *A61F 2/852* (2013.01)
    *A61F 2/06* (2013.01)
    *A61F 2/848* (2013.01)
    *A61F 2/856* (2013.01)

(52) U.S. Cl.
    CPC ............. *A61F 2/856* (2013.01); *A61F 2/95* (2013.01); *A61F 2/9522* (2020.05); *A61F 2002/061* (2013.01); *A61F 2002/065* (2013.01); *A61F 2002/067* (2013.01); *A61F 2002/072* (2013.01); *A61F 2002/075* (2013.01); *A61F 2002/826* (2013.01); *A61F 2002/828* (2013.01); *A61F 2220/005* (2013.01); *A61F 2220/0025* (2013.01); *A61F 2220/0058* (2013.01); *A61F 2220/0075* (2013.01); *A61F 2230/001* (2013.01); *A61F 2230/006* (2013.01); *A61F 2250/006* (2013.01); *A61F 2250/0062* (2013.01); *A61F 2250/0098* (2013.01)

(56) References Cited

U.S. PATENT DOCUMENTS

| | | | |
|---|---|---|---|
| 5,628,788 A | 5/1997 | Pinchuk | |
| 5,676,696 A | 10/1997 | Marcade | |
| 5,800,526 A | 9/1998 | Anderson et al. | |
| 5,824,044 A | 10/1998 | Quiachon et al. | |
| 5,843,158 A | 12/1998 | Lenker et al. | |
| 5,860,998 A | 1/1999 | Robinson et al. | |
| 5,906,641 A | 5/1999 | Thompson et al. | |
| 6,102,940 A | 8/2000 | Robichon et al. | |
| 6,136,022 A | 10/2000 | Nunez et al. | |
| 6,176,875 B1 | 1/2001 | Lenker et al. | |
| 6,210,435 B1 | 4/2001 | Piplani | |
| 6,224,609 B1 | 5/2001 | Ressemann et al. | |
| 6,409,757 B1 | 6/2002 | Trout et al. | |
| 6,454,796 B1 | 9/2002 | Barkman et al. | |
| 6,551,350 B1 | 4/2003 | Thornton et al. | |
| 6,695,875 B2 | 2/2004 | Stelter et al. | |
| 6,814,752 B1 | 11/2004 | Chuter | |
| 6,887,268 B2 | 5/2005 | Butaric et al. | |
| 7,122,052 B2 | 10/2006 | Greenhalgh | |
| 7,267,685 B2 | 9/2007 | Butaric et al. | |
| 7,393,357 B2 | 7/2008 | Stelter et al. | |
| 7,435,253 B1 | 10/2008 | Hartley et al. | |
| 7,537,606 B2 | 5/2009 | Hartley et al. | |
| 7,641,684 B2 | 1/2010 | Hilaire et al. | |
| 7,655,037 B2 | 2/2010 | Fleming et al. | |
| 7,678,141 B2 | 3/2010 | Greenan et al. | |
| 7,682,380 B2 | 3/2010 | Thornton et al. | |
| 7,846,194 B2 | 12/2010 | Hartley et al. | |
| 7,862,604 B1 | 1/2011 | Marcade | |
| 7,914,569 B2 | 3/2011 | Nguyen et al. | |
| 7,998,187 B2 | 8/2011 | Hartley et al. | |
| 8,021,412 B2 | 9/2011 | Hartley et al. | |
| 8,021,413 B2 | 9/2011 | Dierking et al. | |
| 8,167,930 B2 | 5/2012 | Allen et al. | |
| 9,283,068 B2* | 3/2016 | Kelly | A61F 2/848 |
| 9,427,308 B2* | 8/2016 | Kelly | A61F 2/848 |
| 10,350,052 B2* | 7/2019 | Kelly | A61F 2/954 |
| 2001/0014823 A1 | 8/2001 | Ressemann et al. | |
| 2001/0010184 A1 | 9/2001 | Dehdashtian et al. | |
| 2001/0020184 A1* | 9/2001 | Dehdashtian | A61F 2/07 623/1.16 |
| 2002/0058986 A1 | 5/2002 | Landau et al. | |
| 2002/0068967 A1 | 6/2002 | Drasler et al. | |
| 2002/0169497 A1 | 11/2002 | Wholey et al. | |
| 2003/0114923 A1 | 6/2003 | Swanick et al. | |
| 2003/0120333 A1 | 6/2003 | Ouriel | |
| 2003/0195614 A1 | 10/2003 | Ryan | |
| 2003/0199967 A1 | 10/2003 | Hartley et al. | |
| 2003/0204242 A1 | 10/2003 | Zarins | |
| 2004/0082990 A1 | 4/2004 | Hartley | |
| 2004/0117003 A1 | 6/2004 | Ouriel et al. | |
| 2004/0193252 A1 | 9/2004 | Perez et al. | |
| 2004/0193254 A1 | 9/2004 | Greenbert et al. | |
| 2004/0243221 A1 | 12/2004 | Fawzi et al. | |
| 2005/0010277 A1 | 1/2005 | Chuter | |
| 2005/0102018 A1 | 5/2005 | Carpenter et al. | |
| 2005/0131516 A1 | 6/2005 | Greenhalgh | |
| 2006/0025850 A1 | 2/2006 | Feller et al. | |
| 2006/0095116 A1 | 5/2006 | Bolduc | |
| 2006/0184228 A1 | 8/2006 | Khoury | |
| 2006/0187704 A1* | 8/2006 | Johnson | G11C 11/1653 365/158 |
| 2006/0224228 A1 | 10/2006 | Dehadashtian et al. | |
| 2006/0247761 A1 | 11/2006 | Greenberg et al. | |
| 2006/0259136 A1 | 11/2006 | Nguyen et al. | |
| 2006/0276883 A1 | 12/2006 | Greenberg et al. | |
| 2006/0287704 A1* | 12/2006 | Hartley | A61F 2/07 623/1.13 |
| 2007/0055360 A1 | 3/2007 | Hanson et al. | |
| 2007/0112581 A1 | 5/2007 | Smith et al. | |
| 2007/0162109 A1 | 7/2007 | Davila et al. | |
| 2007/0250154 A1 | 10/2007 | Greenberg et al. | |
| 2008/0046065 A1 | 2/2008 | Hartley et al. | |
| 2008/0046068 A1 | 2/2008 | Burgermeister et al. | |
| 2008/0147163 A1 | 6/2008 | Allen | |
| 2009/0099649 A1 | 4/2009 | Chobotov et al. | |
| 2009/0264987 A1 | 10/2009 | Gale | |
| 2010/0057191 A1 | 3/2010 | Pavcnik et al. | |
| 2010/0100168 A1 | 4/2010 | Chuter et al. | |
| 2011/0257731 A1 | 10/2011 | Hartley et al. | |
| 2011/0270377 A1 | 11/2011 | Hartley et al. | |
| 2012/0065725 A1 | 3/2012 | Glynn | |
| 2012/0123527 A1 | 5/2012 | Isch | |
| 2012/0290068 A1 | 11/2012 | Roeder et al. | |
| 2013/0013052 A1 | 1/2013 | Christiansen et al. | |
| 2013/0041457 A1 | 2/2013 | Zhang et al. | |
| 2013/0274851 A1 | 10/2013 | Kelly et al. | |

FOREIGN PATENT DOCUMENTS

| | | |
|---|---|---|
| CN | 2675083 | 2/2005 |
| CN | 200970283 | 11/2007 |
| CN | 101259045 | 9/2008 |
| CN | 201303993 | 9/2009 |
| CN | 101579265 | 3/2011 |
| CN | 102125470 | 7/2011 |
| CN | 102379757 | 4/2014 |
| FR | 2775182 | 8/1999 |
| JP | 1998328215 | 12/1998 |
| JP | 2000237216 | 9/2000 |
| JP | 47294988 B2 | 2/2007 |
| JP | 2008539985 | 11/2008 |
| JP | 200916008 | 7/2009 |
| JP | 2009160080 | 7/2009 |
| JP | 2011526802 | 11/2011 |
| WO | 1997/12562 | 4/1997 |
| WO | 1997/43983 | 11/1997 |

(56) References Cited

FOREIGN PATENT DOCUMENTS

| WO | 1998/09584 | 3/1998 |
|---|---|---|
| WO | 1998/27893 | 7/1998 |
| WO | 1998/53761 | 12/1998 |
| WO | 1999/65419 | 12/1999 |
| WO | 2000/18322 | 4/2000 |
| WO | 2003/099108 | 12/2003 |
| WO | 2004/110314 | 12/2004 |
| WO | 2008/021556 | 2/2008 |
| WO | 2009/046372 | 4/2009 |
| WO | 2010/120419 | 10/2010 |
| WO | 2010/144162 | 12/2010 |
| WO | 2011/108409 | 9/2011 |

OTHER PUBLICATIONS

Examination Report from the Indian Intellectual Property Office for application No. 8053/CHENP/2014, dated Nov. 23, 2020.
Search Report from the Japanese Patent Office for 2015505908, dated Jan. 20, 2017.
Search Report from the Japanese Patent Office for 2015505910, dated Jan. 20, 2017.
Search Report from the Japanese Patent Office for 2015505907, dated Jan. 12, 2017.
Search Report from the Japanese Patent Office for 2015505911, dated Jan. 27, 2017.
Search Report from the Japanese Patent Office for 2015505913, dated Jan. 20, 2017.
International Search Report for PCT/US2013/036173, dated Jul. 19, 2013.
International Search Report for PCT/US2013/036180, dated Apr. 15, 2014.
International Search Report for PCT/US2013/036184, dated Jul. 17, 2013.
International Search Report for PCT/US2013/036190, dated Jul. 17, 2013.
International Search Report for PCT/US2013/036192, dated Jul. 17, 2013.
International Search Report for PCT/US2013/036195, dated Jul. 19, 2013.
International Search Report for PCT/US2013/074359, dated Apr. 13, 2014.
Search Report from the State Intellectual Property Office of the People's Republic of China for Chinese Application No. 2013800312740, dated Oct. 9, 2015.
Search Report from the State Intellectual Property Office of the People's Republic of China for Chinese Application No. 2013800312755, dated Oct. 28, 2015.
Search Report from the State Intellectual Property Office of the People's Republic of China for Chinese Application No. 2013800312806, dated Oct. 10, 2015.
Search Report from the State Intellectual Property Office of the People's Republic of China for Chinese Application No. 2013800312986, dated Oct. 27, 2015.
Search Report from the State Intellectual Property Office of the People's Republic of China dated Aug. 20, 2015 for Application No. 201380031300X.
Search Report from the State Intellectual Property Office of the People's Republic of China dated Aug. 25, 2015 for Application No. 2013800313122.

* cited by examiner

DEBRANCHING VISCERAL STENT GRAFT AND METHODS FOR USE

CROSS-REFERENCE TO RELATED APPLICATIONS

This application is a continuation of U.S. Non-Provisional application Ser. No. 15/250,583, filed Aug. 29, 2016, which is a continuation of U.S. Pat. No. 9,427,308, issued on Aug. 30, 2016 (application Ser. No. 14/625,517, filed Feb. 18, 2015), which is a continuation of U.S. Pat. No. 9,393,101, issued on Jul. 19, 2016 (application Ser. No. 13/706,086, filed on Dec. 5, 2012), that claims the benefit of the filing date of U.S. Provisional Patent Application Ser. No. 61/623,151, filed Apr. 12, 2012, U.S. Provisional Patent Application Ser. No. 61/646,637, filed May 14, 2012, U.S. Provisional Patent Application Ser. No. 61/716,292, filed Oct. 19, 2012, U.S. Provisional Patent Application Ser. No. 61/716,315, filed Oct. 19, 2012, U.S. Provisional Patent Application Ser. No. 61/716,326, filed Oct. 19, 2012, U.S. Provisional Patent Application Ser. No. 61/720,803, filed Oct. 31, 2012, U.S. Provisional Patent Application Ser. No. 61/720,829, filed Oct. 31, 2012 and U.S. Provisional Patent Application Ser. No. 61/720,846, filed Oct. 31, 2012, which are hereby incorporated by reference in their entirety.

BACKGROUND OF THE INVENTION

Aneurysms occur in blood vessels in locations where, due to age, disease or genetic predisposition, insufficient blood vessel strength or resiliency may cause the blood vessel wall to weaken and/or lose its shape as blood flows, resulting in a ballooning or stretching of the blood vessel at the limited strength/resiliency location, thus forming an aneurysmal sac. Left untreated, the blood vessel wall may continue to expand to the point where the remaining strength of the blood vessel wall cannot hold and the blood vessel will fail at the aneurysm location, often with fatal result.

Various implantable medical devices and minimally invasive methods for implantation of these devices have been developed to deliver these medical devices within the vascular system. These devices are advantageously inserted intravascularly, typically from a delivery catheter. In order to prevent rupture of an aneurysm, a stent graft may be introduced into a blood vessel, deployed, and secured in a location within the blood vessel such that the stent graft spans the aneurysmal sac. The outer surface of the stent graft, at its opposed ends, abuts and seals against the interior wall of the blood vessel at a location where the blood vessel wall has not suffered a loss of strength or resiliency. The stent graft channels the blood flow through the hollow interior of the stent graft, thereby reducing, if not eliminating, any stress on the blood vessel wall at the aneurysmal sac location.

In the aorta of a human or animal patient, there are a number of important branch vessels which, when treating an aneurysm through deployment of an endovascular graft, must not be occluded. Current stent graft systems utilize fenestrations or perforations within stent graft walls intended to be aligned with the opening of a given branch vessel, but placement of the stent graft must be very exact and operational alignment is often unsuccessful. When proper fenestration alignment fails, the wall of the deployed stent graft prevents blood flow to the branch vessel. In this case, the physician has no endovascular backup option and must proceed with a significantly more invasive procedure.

Even when the fenestration is properly aligned with the opening of the branch vessel, the fenestration may rotate away from the branch vessel. To prevent this rotation from occurring, a stent graft may be deployed within the branch vessel with one of its ends married to or joined with the fenestration of the previously placed stent graft. The techniques to marry another stent graft to that fenestration are often time consuming, require complicated surgical procedures and demand additional vessel or vascular access points. The marrying of two stent grafts via a fenestration also has the additional problem of an inadequate seal where the two stent grafts are joined.

Further, current common iliac aneurysm treatments involve ligation or embolization of the internal iliac artery, frequently leading to side effects including, but not limited to, erectile dysfunction in men, decreased exercise tolerance, and compromise to pelvic profusion that may result in bowel ischemia and death.

SUMMARY OF THE INVENTION

Visceral Double-Barreled Main Body Stent Graft and Methods for Use

In a first aspect, the invention provides a stent graft comprising, (a) a main body stent graft having a distal end and a proximal end, wherein the main body stent graft has a length in the range from about 100 mm to about 120 mm, wherein the main body stent graft has a diameter at the proximal end in the range from about 30 mm to about 45 mm, (b) a first lumen defined at the distal end of the main body stent graft, wherein the first lumen has a diameter in the range from about 18 mm to about 20 mm, (c) a second lumen defined at the distal end of the main body stent graft, wherein the second lumen has a diameter in the range from about 16 mm to about 18 mm, wherein the first lumen and the second lumen have about the same length from about 50 mm to about 70 mm, wherein the first lumen is secured to the second lumen along a shared length, and (d) wherein the main body stent graft defines a tubular wall that is contiguous with the first lumen and the second lumen such that any fluid entering the main body must exit through one of the first lumen or the second lumen.

In a second aspect, the invention provides a stent graft comprising, (a) a main body stent graft having a distal end and a proximal end, wherein the main body stent graft has a length in the range from about 100 mm to about 120 mm, (b) a first lumen defined about 5 mm from the proximal end of the main body to the distal end of the main body, wherein the first lumen has a substantially constant diameter along its length in the range from about 18 mm to about 20 mm, (c) a second lumen defined about 5 mm from the proximal end of the main body to the distal end of the main body, wherein the second lumen has a substantially constant diameter along its length in the range from about 16 mm to about 18 mm, wherein the first lumen is secured to the second lumen along a shared length.

In a third aspect, the invention provides a method for placement of a stent graft according to the first or second aspects of the invention, comprising, (a) introducing a guidewire into an aorta via arterial access, (b) loading a delivery catheter containing a stent graft according to the first or second aspects of the invention onto the guidewire, (c) moving the delivery catheter along the guidewire and introducing the delivery catheter into the aorta via arterial access, and (d) deploying the stent graft into the thoracic aorta.

In a fourth aspect, the invention provides a method for placement of a stent graft according to the first or second aspects of the invention, comprising, (a) introducing a guidewire into an aortic arch via arterial access, (b) loading a delivery catheter containing a stent graft according to the first or second aspects of the invention onto the guidewire, wherein a distal end of the stent graft is loaded first, (c) moving the delivery catheter along the guidewire and introducing the delivery catheter into the aortic arch via arterial access, and (d) deploying the stent graft into a proximal descending aorta.

In a fifth aspect, the invention provides a method for placement of a stent graft according to the first or second aspects of the invention, comprising, (a) introducing a guidewire into an thoracic or abdominal aorta via arterial access, (b) loading a delivery catheter containing a stent graft according to the first or second aspects of the invention onto the guidewire, (c) moving the delivery catheter along the guidewire and introducing the delivery catheter into the thoracic or abdominal aorta via arterial access, and (d) deploying the stent graft into the thoracic or abdominal aorta.

The double-barreled stent graft and methods described with respect to the first through the fifth aspects of the invention provide numerous benefits. One advantage over previously known single lumen main body stent grafts, the double-barreled stent graft can also be used as a "platform" or "anchor" that enables a surgeon to debranch visceral vessels, for example, while maintaining blood flow to the rest of the body without putting a patient on bypass, providing a significant improvement over prior devices and techniques. This anchoring main body stent graft can be utilized in combination with any embodiment of the debranching stent grafts and stent graft limbs disclosed herein. In one non-limiting example, the double-barreled stent graft can be used for the treatment of any aneurysm of any anatomical variation or other type of diseased aorta or traumatic injury.

In addition, the double-barreled stent graft may be deployed transapically, transfemorally, via the right subclavian artery, or via any other accessible artery. When the double-barreled stent graft is deployed in vivo, aortic flow is compartmentalized immediately, which increases surgical options by allowing the surgeon to engage in individual selection of the lumens for placement of additional debranching stent grafts. The second lumen provides a built-in back-up system in case an issue arises with stent placement in the first lumen, for example. The double-barreled stent graft also minimizes surgical impact on the patient and leads to reduced complication rates, reduced risk of renal failure, bowel ischemia, and heart attack and decreased time for patient stabilization.

Further, the contiguous nature of the walls of the double-barreled stent graft's main body with the first and second lumens has the additional benefit of preventing extraneous blood flow into the aneurysm. The walls of the double-barreled stent graft provide a complete circumferential seal and there is no external compromise or compression of the lumen walls, which prevents blood flow through the lumens from being affected. Previous "sandwich," "snorkel" and "chimney" devices were constructed by simultaneously placing two or more single lumen stent grafts side by side within the aorta. These previous stent grafts defined open spaces where the walls of the lumens did not completely abut each other or the aortic walls and allowed blood to flow through the open spaces and into the aneurysm. These previous devices were further subject to collapse or compression due to external pressures.

In addition, the cylindrical nature of walls of the double-barreled stent graft provide more positive fixation with the wall of the aorta than provided by previous devices.

Aortic Arch Double-Barreled Main Body Stent Graft and Methods for Use

In a sixth aspect, the invention provides a stent graft comprising, (a) a main body stent graft having a distal end and a proximal end, wherein the main body stent graft has a length in the range from about 50 mm to about 70 mm, wherein the main body stent graft has a diameter at the proximal end in the range from about 40 mm to about 60 mm, (b) a first lumen defined at the distal end of the main body stent graft, wherein the first lumen has a diameter in the range from about 18 mm to about 30 mm, (b) a second lumen defined at the distal end of the main body stent graft, wherein the second lumen has a diameter in the range from about 18 mm to about 30 mm, (c) wherein the first lumen is secured to the second lumen along a shared length, wherein the shared length of the first lumen and the second lumen is in the range from about 30 mm to about 65 mm, and (d) wherein the main body stent graft defines a tubular wall that is contiguous with the first lumen and the second lumen such that any fluid entering the main body must exit through one of the first lumen or the second lumen.

In one embodiment of the sixth aspect of the invention, the first lumen and the second lumen are defined by a seam starting at the distal end of the main body stent graft and extending towards the proximal end of the main body stent graft.

In another embodiment, sixth aspect of the invention further comprises a cylindrical stent graft structure coextensive with and disposed on an exterior of the main body stent graft.

In a further embodiment, the sixth aspect of the invention further comprises a stent valve affixed to the proximal end of the main body stent graft, where a free end of the stent valve is covered and a portion of the stent valve extending between the free end and the main body stent graft is uncovered.

In a seventh aspect, the invention provides a method for placement of a stent graft from the sixth aspect of the invention, comprising, (a) introducing a guidewire into an aorta via arterial access, (b) loading a delivery catheter containing a stent graft according to the sixth aspect of the invention onto the guidewire, (c) moving the delivery catheter along the guidewire and introducing the delivery catheter into the aorta via arterial access, and (d) deploying the stent graft into the aorta.

In one embodiment, the seventh aspect further comprises (e) loading a second delivery catheter containing a debranching stent graft according to the thirteenth aspect of the invention onto the guidewire, (f) moving the second delivery catheter along the guidewire and introducing the delivery catheter into the aorta via arterial access, and (g) deploying the debranching stent graft into one of the aorta or a lumen of a previously-placed stent graft, such as a stent graft according to the sixth aspect of the invention within the aorta.

In another embodiment, the seventh aspect still further comprises, (h) introducing a second guidewire into the aorta via arterial access, (i) loading a third delivery catheter containing a great vessel limb according to the thirteenth aspect of the invention onto the second guidewire, (j) moving the third delivery catheter along the second guidewire and introducing the third delivery catheter into a selected leg of the debranching stent graft via arterial access, and (k) deploying a proximal end of the great vessel limb into the selected leg of the debranching stent graft according to the thirteenth aspect of the invention.

In an eighth aspect, the invention provides a method for placement of a stent graft from the sixth aspect of the invention, comprising, (a) introducing a guidewire into an aortic arch via the femoral artery, (b) loading a delivery catheter containing a stent graft according to the sixth aspect of the invention onto the guidewire, wherein a distal end of the stent graft is loaded first, (c) moving the delivery catheter along the guidewire and introducing the delivery catheter into the aortic arch via arterial access, and (d) deploying the stent graft into a proximal descending aorta.

In a ninth aspect, the invention provides a method for placement of a stent graft from the sixth aspect of the invention, comprising, (a) introducing a guidewire into an ascending aorta via arterial access, (b) loading a delivery catheter containing a stent graft according to the sixth aspect of the invention onto the guidewire, (c) moving the delivery catheter along the guidewire and introducing the delivery catheter into the ascending aorta via arterial access, and (d) deploying the stent graft into the ascending aorta.

The double-barreled stent graft and methods described with respect to the sixth through the ninth aspects of the invention provide numerous benefits. One advantage over previously known single lumen main body stent grafts, the double-barreled stent graft can also be used as a "platform" or "anchor" that enables a surgeon to debranch Great vessels, for example, while maintaining blood flow to the rest of the body without putting a patient on bypass, providing a significant improvement over prior devices and techniques. This anchoring main body stent graft can be utilized in combination with any embodiment of the debranching stent grafts and/or stent graft limbs disclosed herein. In one non-limiting example, the double-barreled stent graft can be used for the treatment of any aneurysm of any anatomical variation or other type of diseased aorta or traumatic injury.

In addition, the double-barreled stent graft may be deployed transapically, transfemorally, via the right subclavian artery, or via any other accessible artery. Unlike previously known stent grafts, the double-barreled stent graft can be deployed in the ascending aorta. Further, when the double-barreled stent graft is deployed in vivo, aortic flow is compartmentalized immediately, which increases surgical options by allowing the surgeon to engage in individual selection of the lumens for placement of additional debranching stent grafts. The second lumen provides a built-in back-up system in case an issue arises with stent placement in the first lumen, for example. The double-barreled stent graft also minimizes surgical impact on the patient and leads to reduced complication rates, reduced risk of renal failure, bowel ischemia, and heart attack and decreased time for patient stabilization.

Further, the contiguous nature of the walls of the double-barreled stent graft's main body with the first and second lumens has the additional benefit of preventing extraneous blood flow into the aneurysm. The walls of the double-barreled stent graft provide a complete circumferential seal and there is no external compromise or compression of the lumen walls, which prevents blood flow through the lumens from being affected. Previous "sandwich," "snorkel" and "chimney" devices were constructed by simultaneously placing two or more single lumen stent grafts side by side within the aorta. These previous stent grafts defined open spaces where the walls of the internal lumens did not completely abut each other or the aortic walls and allowed blood to flow through the open spaces and into the aneurysm. These previous devices were further subject to collapse or compression due to external pressures.

In addition, the cylindrical nature of walls of the double-barreled stent graft provide more positive fixation with the wall of the aorta than provided by previous devices.

Debranching Visceral Stent Graft and Methods for Use

In a tenth aspect, the invention provides a debranching stent graft comprising, (a) a main body stent graft with a bifurcation defining a first leg and a second leg, wherein the main body stent graft has a distal end and a proximal end, (b) wherein the main body stent graft has a diameter at the proximal end in the range from about 18 mm to about 22 mm, (c) wherein the first leg and the second leg each have a diameter in the range from about 14 mm to about 16 mm, (d) wherein the distance from the proximal end of the main body to the distal end of the first leg is in the range from about 70 mm to about 90 mm, (e) and wherein the distance from the proximal end of the main body to the distal end of the second leg is in the range from about 80 mm to about 100 mm, and wherein the second leg is at least about 10 mm longer than the first leg.

In one embodiment of the tenth aspect of the invention, the second leg is no more than about 20 mm longer than the first leg. In another embodiment of the tenth aspect of the invention, the bifurcation occurs in the range from about 30 mm to about 40 mm from the proximal end.

In one embodiment, the tenth aspect of the invention further comprises a first visceral limb joined with one of the first leg or the second leg at the distal end of the main body stent graft. In a further embodiment, the first visceral limb has a bifurcation defining a third leg and a fourth leg.

In still another embodiment, the tenth aspect of the invention further comprises a second visceral limb attached to the other of the first leg or the second leg.

In an eleventh aspect, the invention provides a debranching stent graft comprising, (a) a main body stent graft with a bifurcation defining a first leg and a second leg, wherein the main body stent graft has a distal end and a proximal end, (b) wherein the main body stent graft has a diameter at the proximal end in the range from about 28 mm to about 36 mm, (c) wherein the first leg and the second leg each have a diameter of about 14 mm, (d) wherein the distance from the proximal end of the main body to the distal end of the first leg is about 70 mm, (e) and wherein the distance from the proximal end of the main body to the distal end of the second leg is about 80 mm.

In one embodiment, the eleventh aspect further comprises a visceral limb attached to the first leg at the distal end of the main body stent graft, wherein the first visceral limb has a bifurcation defining a third leg and a fourth leg, wherein the bifurcation occurs immediately at the proximal end of the first visceral limb, wherein the first visceral limb has a length of about 30 mm, and wherein each of the third leg and the fourth leg have a diameter of about 7 mm.

In one embodiment, the eleventh aspect further comprises, a visceral extension joined with the second leg, wherein the visceral extension has a proximal end and a distal end, wherein the visceral extension comprises a tubular main leg with a bifurcation defining a first extension leg and a second extension leg, wherein the first extension leg has a distal diameter of about 7 mm and the second extension leg has a distal diameter of about 16 mm, and wherein the visceral extension has a diameter of about 15 mm at the proximal end and a diameter of about 20 mm at the bifurcation, wherein the visceral extension has a length of about 93 mm.

In a twelfth aspect, the invention provides a method for placement of a debranching stent graft according to the tenth or eleventh aspect of the invention, comprising (a) introducing a guidewire into an aorta via arterial access, (b) loading a delivery catheter containing a debranching stent graft according to the tenth or eleventh aspect of the invention onto the guidewire, (c) moving the delivery catheter along the guidewire and introducing the delivery catheter into the aorta via arterial access, (d) and deploying the debranching stent graft into one of the aorta or a lumen of a previously-placed stent graft, such as a stent graft according to the first or second aspects of the invention within the aorta.

In one embodiment, the twelfth aspect further comprises, (e) introducing a second guidewire into the aorta via arterial access, (f) loading a second delivery catheter containing a visceral limb stent graft according to the tenth or eleventh aspect of the invention onto the second guidewire, (g) moving the second delivery catheter along the second guidewire and introducing the second delivery catheter into a selected leg of the debranching stent graft according to the tenth or eleventh aspect of the invention via arterial access, and (h) deploying a proximal end of the visceral limb stent graft into the selected leg of the debranching stent graft according to the tenth or eleventh aspect of the invention.

In another embodiment, the twelfth aspect further comprises, (i) introducing a third guidewire into the aorta via arterial access and into a selected lumen of the debranching stent graft according to the tenth or eleventh aspect of the invention, (j) loading a third delivery catheter containing a visceral extension stent graft according to the tenth or eleventh aspect of the invention onto the third guidewire, (k) moving the third delivery catheter along the third guidewire and introducing the third delivery catheter into the selected lumen of the debranching stent graft via arterial access, and (l) deploying a proximal end of the visceral extension stent graft into the selected lumen of the debranching stent graft, while the distal end extends into a native vessel.

The debranching stent graft and methods described with respect to the tenth through the twelfth aspects of the invention provide numerous benefits. For example, the debranching stent graft can be used in combination with any embodiment of the double-barreled stent graft or stent graft limb disclosed herein, or other main body anchoring stent graft, for treatment of any aneurysm of any anatomical variation or other type of diseased aorta or traumatic injury. The debranching stent graft also beneficially adds another level of debranching, from one level to two, via the first and second legs. In addition, a further level of debranching, from two levels to four, can be obtained depending on the visceral limb(s) selected for use in certain embodiments. Further, the modular nature of the visceral limbs, in some embodiments, provides versatility for stent selection and provides built-in back-up systems so the surgeon can diverge from the planned treatment plan. These capabilities ensure that blood flow to end organs is maintained during the entire procedure.

Further, the debranching stent graft allows for a top-down debranching approach, which can be advantageous depending on the desired vessel location for placement of the stent-graft. One non-limiting example is to use an arm approach when stenting the visceral arteries. The arm approach provides an optimal angle of attack, whether there is a normal or tortuous path to reach the vessel, to extend a guidewire through a leg of the debranching stent graft and into the visceral arteries in order to place an extension stent graft from the top-down. This approach moves the stent graft and guidewire with the natural direction of blood flow ensuring natural laminar flow.

Debranching Great Vessel Stent Graft and Methods for Use

In a thirteenth aspect, the invention provides a debranching stent graft comprising, (a) a main body stent graft with a first bifurcation defining a first leg and a second leg, wherein the main body stent graft has a distal end and a proximal end, wherein the main body stent graft has a diameter at the proximal end in the range from about 18 mm to about 28 mm, (b) wherein the first leg and the second leg each have a diameter in the range from about 12 mm to about 18 mm, (c) wherein the distance from the proximal end of the main body to the distal end of the first leg is in the range from about 30 mm to about 50 mm, and (d) wherein the distance from the proximal end of the main body to the distal end of the second leg is in a range from about 50 mm to about 70 mm.

In one embodiment of the thirteenth aspect of the invention, the first bifurcation occurs in the range from about 20 mm to about 45 mm from the proximal end.

In another embodiment, the thirteenth aspect of the invention further comprises a first great vessel limb joined with one of the first leg or the second leg at the distal end of the main body stent graft. In a further embodiment, the first great vessel limb has a bifurcation defining a third leg and a fourth leg.

In still another embodiment, the thirteenth aspect of the invention further comprises a second visceral limb attached to the other of the first leg or the second leg.

In a further embodiment, the second visceral limb comprises an extension stent graft.

In a fourteenth aspect, the invention provides a method for placement of a debranching stent graft according to the thirteenth aspect of the invention, comprising (a) introducing a guidewire into an aorta via arterial access, (b) loading a delivery catheter containing a debranching stent graft according to the thirteenth aspect of the invention onto the guidewire, (c) moving the delivery catheter along the guidewire and introducing the delivery catheter into the aorta via arterial access, and (d) deploying the debranching stent graft into one of the aorta or a lumen of a previously-placed stent graft, such as a stent graft according to the sixth aspect of the invention within the aorta.

In one embodiment, the fourteenth aspect further comprises, (e) introducing a second guidewire into the aorta via arterial access, (f) loading a second delivery catheter containing a great vessel limb according to the thirteenth aspect of the invention onto the second guidewire, (g) moving the second delivery catheter along the second guidewire and introducing the second delivery catheter into a selected leg of the debranching stent graft via arterial access, and (h) deploying a proximal end of the great vessel limb into the selected leg of the debranching stent graft.

In one embodiment, the fourteenth aspect still further comprises, (i) introducing a third guidewire into the aorta via arterial access and into a selected lumen of the debranching stent graft, (j) loading a third delivery catheter containing an extension stent graft according to the thirteenth aspect of the invention onto the third guidewire, (k) moving the third delivery catheter along the third guidewire and introducing the third delivery catheter into the selected lumen of the debranching stent graft via arterial access, and (l) deploying a proximal end of the extension stent graft into the selected lumen of the debranching stent graft, while the distal end of the extension stent graft extends into a vessel.

In a fifteenth aspect, the invention provides a method for placement of a debranching stent graft according to the thirteenth aspect of the invention, comprising (a) introducing a guidewire into an aortic arch via arterial access, (b) loading a delivery catheter containing a debranching stent graft according to the thirteenth aspect of the invention onto the guidewire, (c) moving the delivery catheter along the guidewire and introducing the delivery catheter into the aortic arch via arterial access, and (d) deploying the debranching stent graft into one of the proximal descending aorta or a lumen of a previously-placed stent graft, such as a stent graft according to the sixth aspect of the invention within the proximal descending aorta.

In a sixteenth aspect, the invention provides a method for placement of a debranching stent graft according to the thirteenth aspect of the invention, comprising (a) introducing a guidewire into an ascending aorta via arterial access, (b) loading a delivery catheter containing a debranching stent graft according to the thirteenth aspect of the invention onto the guidewire, (c) moving the delivery catheter along the guidewire and introducing the delivery catheter into the ascending aorta via arterial access, and (d) deploying the debranching stent graft into one of the ascending aorta or a lumen of a previously-placed stent graft, such as a stent graft according to the sixth aspect of the invention within the ascending aorta.

In one embodiment, the sixteenth aspect further comprises, (e) introducing a second guidewire into the ascending aorta via arterial access and into a selected leg of the debranching stent graft according to the thirteenth aspect of the invention, (f) loading a second delivery catheter containing a great vessel limb according to the thirteenth aspect of the invention onto the second guidewire, (g) moving the second delivery catheter along the second guidewire and introducing the second delivery catheter into the selected leg of the debranching stent graft via arterial access, and (h) deploying a proximal end of the great vessel limb according to the thirteenth aspect of the invention into the selected leg of the debranching stent graft.

In one embodiment, the sixteenth aspect still further comprises, (i) introducing a third guidewire into the ascending aorta via arterial access and into a selected leg of the debranching stent graft, (j) loading a third delivery catheter containing an extension stent graft according to the thirteenth aspect of the invention onto the third guidewire, (k) moving the third delivery catheter along the third guidewire and introducing the third delivery catheter into the selected leg of the debranching stent graft via arterial access, and (l) deploying a proximal end of the extension stent graft into the selected leg of the debranching stent graft, while the distal end of the extension stent graft extends into a great vessel.

The debranching stent graft and methods described with respect to the thirteenth through the sixteenth aspects of the invention provide numerous benefits. For example, the debranching stent graft can be used in combination with any embodiment of the double-barreled stent graft or stent graft limb disclosed herein, or other main body anchoring stent graft, for treatment of any aneurysm of any anatomical variation or other type of diseased aorta or traumatic injury. The debranching stent graft also beneficially adds another level of debranching, from one level to two, via the first and second legs. In addition, a further level of debranching, from two levels to four, can be obtained depending on the Great vessel limb(s) selected for use in certain embodiments. Further, the modular nature of the Great vessel limbs, in some embodiments, provides versatility for stent selection and provides built-in back-up systems so the surgeon can diverge from the planned treatment plan. These capabilities ensure that blood flow to end organs is maintained during the entire procedure.

Debranching Stent Graft Limb and Methods for Use

In a seventeenth aspect, the invention provides a debranching stent graft limb comprising, (a) a main body stent graft limb with a bifurcation defining a first leg and a second leg, wherein the main body stent graft limb has a distal end and a proximal end, (b) wherein the main body stent graft limb has a diameter at the proximal end in the range from about 14 mm to about 18 mm, (c) wherein the first leg has a diameter ranging from about 8 mm to about 12 mm, (d) wherein the second leg has a diameter ranging from about 6 mm to about 10 mm, and (e) wherein the distance from the proximal end of the main body to the distal end of the first leg and the second leg is in the range from about 70 mm to about 90 mm, and wherein the diameter of the first leg is about 2 mm greater than the diameter of the second leg.

In one embodiment, the seventeenth aspect further comprises (f) a first limb expanded within the first leg and coupled to the first leg via passive fixation and (g) a second limb expanded within the second leg and coupled to the second leg via passive fixation.

In an eighteenth aspect, the invention provides a method for placement of a debranching stent graft limb according to the seventeenth aspect of the invention, comprising, (a) introducing a guidewire into the appropriately sized branched arterial configuration via arterial access, (b) loading a delivery catheter containing a debranching stent graft limb according to the seventeenth aspect of the invention onto the guidewire, (c) moving the delivery catheter along the guidewire and introducing the delivery catheter into the appropriately sized branched arterial configuration via the arterial access, and (d) deploying the debranching stent graft limb into the appropriately sized branched arterial configuration and/or a lumen of a previously-placed stent graft, such as a stent graft according to the tenth, eleventh or thirteenth aspect of the invention.

In one embodiment, the eighteenth aspect of the invention further comprises (e) loading a second delivery catheter containing a first limb according to the seventeenth aspect of the invention onto a proximal end of the guidewire, (f) moving the second delivery catheter along the guidewire and introducing the second delivery catheter into the first leg of the debranching stent graft limb via arterial access, and (g) deploying a proximal end of the first limb the first leg of the debranching stent graft limb.

In another embodiment, the eighteenth aspect of the invention still further comprises (h) introducing a second guidewire into the appropriately sized branched arterial configuration through the second leg of a debranching stent limb according to the seventeenth aspect of the invention via arterial access, (i) loading a third delivery catheter containing a second limb according to the seventeenth aspect of the invention onto the second guidewire, (j) moving the third delivery catheter along the second guidewire and introducing the third delivery catheter into the second leg of the debranching stent graft limb via arterial access, and (k) deploying a proximal end of the second limb into the second leg of the debranching stent graft limb in the appropriately sized branched arterial configuration.

In a nineteenth aspect, the invention provides a method for placement of a debranching stent graft limb according to the seventeenth aspect of the invention, comprising, (a) introducing a guidewire into a common iliac artery via arterial access, (b) loading a delivery catheter containing a debranching stent graft limb according to the seventeenth aspect of the invention onto the guidewire, (c) moving the delivery catheter along the guidewire and introducing the delivery catheter into the common iliac artery via arterial access, and (d) deploying the debranching stent graft limb into the common iliac artery and/or a lumen of a previously-placed stent graft, such as a stent graft according to the tenth, eleventh or thirteenth aspect of the invention.

The debranching stent graft limb and methods described with respect to the seventeenth through the nineteenth aspects of the invention provide numerous benefits. For example, the debranching stent graft limb, deployed in combination with an embodiment of the debranching stent graft, can be used for the treatment of any aneurysm of any anatomical variation or other type of diseased artery or traumatic injury. The debranching stent graft limb also beneficially adds another level of debranching via the first and second legs. This provides a built-in back-up system so the surgeon can diverge from the planned treatment plan in during a debranching procedure.

The debranching stent graft limb has the additional advantage of allowing for revision procedures. For example, if a patient with a previous aortic aneurysm repair, such as a standard infra-renal stent, has a new aneurysm form in the common iliac, the treatment under previous techniques would require embolization of the internal iliac. This is because previous up-and-over techniques would be blocked by previously placed stents. In this scenario, however, a top-down arm approach can be used to place debranching stent graft limb and then to place extension stent grafts into the external and internal iliac arteries.

Combination Double-Barreled and Debranching Stent Grafts and Methods for Use

In a twentieth aspect, the invention provides a stent graft comprising, (a) a main body stent graft defining a single lumen and having a distal end and a proximal end, (b) a first bifurcation in the range from about 20 mm to about 30 mm from the proximal end of the main body defining a first lumen and a second lumen, wherein the main body stent graft defines a tubular wall that is contiguous with the first lumen and the second lumen such that any fluid entering the main body stent graft must exit by entering one of the first lumen or the second lumen, wherein the main body stent graft has a diameter at the proximal end in the range from about 40 mm to about 60 mm, wherein the first lumen and the second lumen each have a diameter in the range from about 18 mm to about 30 mm, wherein the length from the proximal end of the main body stent graft to the distal end of the second lumen is in the range from about 70 mm to about 90 mm, (c) a second bifurcation within the second lumen about 30 mm from the distal end of the second lumen defining a first leg and a second leg, wherein the first leg and the second leg each have a diameter in the range from about 14 mm to about 16 mm, and (d) a third bifurcation within the second leg about 20 mm to 30 mm distal from the second bifurcation defining a third leg and a fourth leg, wherein the third leg and the fourth leg each have a diameter in the range from about 7 mm to about 12 mm, wherein the third and fourth leg each have a length in the range from about 20 mm to about 30 mm.

In one embodiment of the twentieth aspect, the first lumen is secured to the second lumen along a shared length of about 30 mm.

In another embodiment of the twentieth aspect, the first lumen and the second lumen each retain a substantially cylindrical profile.

In a twenty-first aspect, the invention provides a stent graft comprising, (a) a main body stent graft defining a single lumen and having a distal end and a proximal end, (b) a first bifurcation in the range from about 20 mm to about 30 mm from the proximal end of the main body defining a first lumen and a second lumen, wherein the main body stent graft has a diameter at the proximal end in the range from about 40 mm to about 60 mm, wherein the first lumen has a diameter in the range from about 20 mm to about 30 mm at the first bifurcation and has a diameter in the range from about 20 mm to 40 mm at the distal end of the first lumen, wherein the first lumen has a length of about 50 mm to about 150 mm from the first bifurcation to the distal end of the first lumen, wherein the second lumen has a diameter in the range from about 20 mm to about 30 mm at the first bifurcation, (c) a second bifurcation within the second lumen about 30 mm from the distal end of the second lumen defining a first leg and a second leg, wherein the first leg and the second leg each have a diameter in the range from about 14 mm to about 16 mm, wherein the length from the proximal end of the main body stent graft to the distal end of the second lumen's second leg is in the range from about 50 mm to about 70 mm, and (d) a third bifurcation within the first leg that defines a third leg and a fourth leg, wherein the third leg and the fourth leg each have a diameter from about 7 mm to about 12 mm, wherein the third and fourth leg each have a length in the range from about 20 mm to about 30 mm.

In one embodiment of the twenty-first aspect, the first lumen is secured to the second lumen along a shared length from the first bifurcation to the third bifurcation.

In a twenty-second aspect, the invention provides a method for placement of a stent graft according to one of the twentieth or twenty-first aspects of the invention, comprising, (a) introducing a guidewire into an thoracic aorta via arterial access, (b) loading a delivery catheter containing a stent graft according to one of the twentieth or twenty-first aspects of the invention onto the guidewire, (c) moving the delivery catheter along the guidewire and introducing the delivery catheter into the thoracic aorta via arterial access, and (d) deploying the stent graft into the thoracic aorta.

In a twenty-third aspect, the invention provides a method for placement of a stent graft according to one of the twentieth or twenty-first aspects of the invention, comprising, (a) introducing a guidewire into an aorta via arterial access, (b) loading a delivery catheter containing a stent graft according to one of the twentieth or twenty-first aspects of the invention onto the guidewire, (c) moving the delivery catheter along the guidewire and introducing the delivery catheter into the aorta via arterial access, and (d) deploying the stent graft into the aorta.

In a twenty-fourth aspect, the invention provides a method for placement of a stent graft according to one of the twentieth or twenty-first aspects of the invention, comprising, (a) introducing a guidewire into an ascending aorta via arterial access, (b) loading a delivery catheter containing a stent graft according to one of the twentieth or twenty-first aspects of the invention onto the guidewire, (c) moving the delivery catheter along the guidewire and introducing the delivery catheter into the ascending aorta via arterial access, and (d) deploying the stent graft into the ascending aorta.

The stent graft and methods described with respect to the twentieth through the twenty-fourth aspects of the invention provide numerous benefits. One advantage over previously known single lumen main body stent grafts, the double-barreled stent graft can also be used as a "platform" or "anchor" that enables a surgeon to debranch Great vessels, for example, while maintaining blood flow to the rest of the body without putting a patient on bypass. This anchoring main body stent graft can be utilized in combination with any embodiment of the debranching stent grafts and/or stent graft limbs disclosed herein. In one non-limiting example, the double-barreled stent graft can be used for the treatment of any aneurysm of any anatomical variation or other type of diseased aorta or traumatic injury.

Further, the double-barreled stent graft may be deployed transapically, transfemorally, via the right subclavian artery, or via any other accessible artery. Unlike previously known stent grafts, the double-barreled stent graft can be deployed in the ascending aorta. When the double-barreled stent graft is deployed in vivo, aortic flow is compartmentalized immediately, which increases surgical options by allowing the surgeon to engage in individual selection of the lumens for placement of additional debranching stent grafts. The second lumen provides a built-in back-up system in case an issue arises with stent placement in the first lumen, for example. The double-barreled stent graft also minimizes surgical impact on the patient and leads to reduced complication rates, reduced risk of renal failure, bowel ischemia, and heart attack and decreased time for patient stabilization.

In addition, the contiguous nature of the walls of the double-barreled stent graft's main body with the first and second lumens has the additional benefit of preventing extraneous blood flow into the aneurysm. The walls of the double-barreled stent graft provide a complete circumferential seal and there is no external compromise or compression of the lumen walls, which prevents blood flow through the lumens from being affected. Previous "sandwich," "snorkel" and "chimney" devices were constructed by simultaneously placing two or more single lumen stent grafts side by side within the aorta. These previous stent grafts defined open spaces where the walls of the internal lumens did not completely abut each other or the aortic walls and allowed blood to flow through the open spaces and into the aneurysm. These previous devices were further subject to collapse or compression due to external pressures.

In addition, the cylindrical nature of walls of the double-barreled stent graft provide more positive fixation with the wall of the aorta than provided by previous devices.

DETAILED DESCRIPTION

Figure 1A:
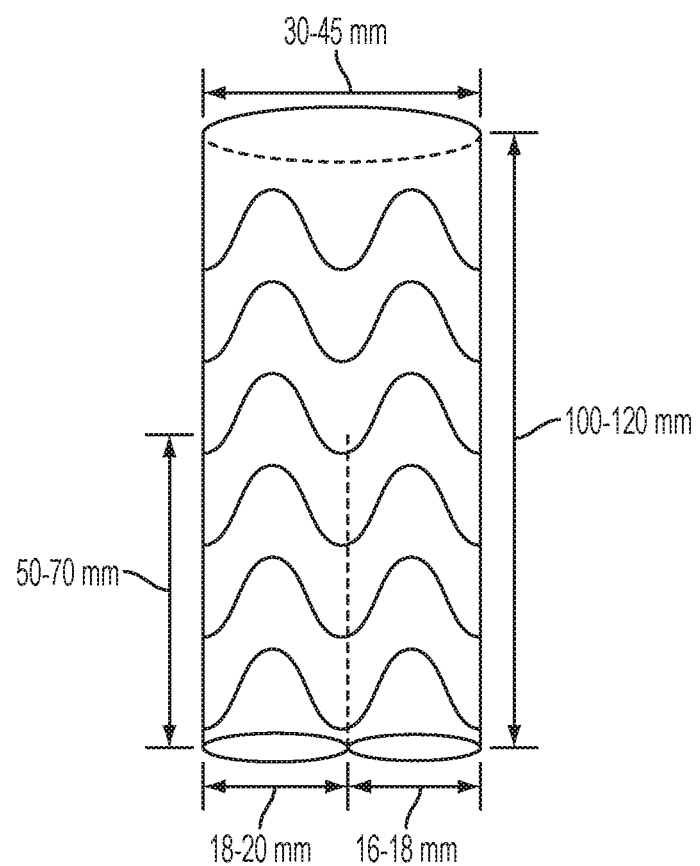
FIG. 1A is an isometric view illustrating the dimensions of one embodiment of a double-barreled stent graft according to the first aspect of the invention.

The present disclosure provides for stent grafts and methods for an anchoring main body stent and/or bridging a defect in a main vessel near one or more branch vessels, for example at or in the vicinity of a bifurcation in the arterial system of a patient.

As used herein, "endo-debranching" is an endovascular surgical technique that refers to placing stent grafts in series to exclude (repair) diseased aorta and to place stent grafts into the branch vessels connected with the aneurysmal sac and/or other vessels, thus allowing exclusion (repair) of the diseased aorta while maintaining blood flow.

As used herein, "branch vessel" refers to a vessel that branches off from a main vessel. The "branch vessels" of the thoracic and abdominal aorta include the innominate, left common carotid, left subclavian, celiac, superior mesenteric arteries, renal(s), and all other minor branches. This does not limit the division of the aorta into the iliac arteries. As another example, the hypogastric artery is a branch vessel to the common iliac, which is a main vessel in this context. Thus, it should be seen that "branch vessel" and "main vessel" are relative terms.

As used herein, "Great vessels" includes the right innominate, the left common carotid, and the left subclavian arteries.

As used herein, "diseased aorta" refers to any diseased portion of the aorta extending from and including the aortic outflow tract to the femoral arteries.

As used herein, "passive fixation" refers to friction, interaction between the cloth of the grafts, radial strength of the stent and blood pressure that holds the component stent grafts together at the site of overlap.

As used herein, an "anchoring main body stent graft" refers to the first stent placed during a debranching procedure, where that first stent graft is in direct contact with a non-diseased portion of the arterial vessel wall.

As used herein, with respect to measurements, "about" means +/−5%.

As used herein, with respect to cylindrical configurations or profiles and constant lumen diameters, "substantially" means being largely but, in some instances, not wholly that which is specified. In other words, lumens and cylinders may not be perfectly round.

As used herein, a "fenestration" refers to perforations within stent graft walls intended to be aligned with the opening of a given branch vessel.

As used herein, a "stent graft" is a tubular, radially-expandable device comprising a fluid-tight fabric supported by a stent, and is used to bridge diseased arteries. Such stent grafts and methods for their deployment and use are known to those of skill in the art. For example, vascular sheaths can be introduced into the patient's arteries, through which items, including but not limited to, guidewires, catheters and, eventually, the stent graft, is passed.

As used herein, "stent" is typically a cylindrical frame and means any device or structure that adds rigidity, expansion force, or support to a prosthesis, while "stent graft" refers to a prosthesis comprising a stent and a graft material associated therewith that forms a fluid-tight lumen through at least a portion of its length. A "graft" is a cylindrical liner that may be disposed on the stent's interior, exterior or both. A wide variety of attachment mechanisms are available to join the stent and graft together, including but not limited to, sutures, adhesive bonding, heat welding, and ultrasonic welding.

The stent can be made of any suitable material, including but not limited to biocompatible metals, implantable quality stainless steel wires, nickel and titanium alloys, and biocompatible plastics attached to a graft. Any suitable fluid tight graft material can be used. In a preferred embodiment, the graft material is a biocompatible fabric, including but not limited to woven or knitted polyester, such as poly(ethylene terephthalate), polylactide, polyglycolide and copolymers thereof; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. Materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. The graft material may also include extracellular matrix materials.

The covered stent grafts can be made of any suitable material, including but not limited to polytetrafluoroethylene (ePTFE) lined nickel-titanium alloy stent. The stent grafts are preferably covered and flexible. The stent grafts may contain any other suitable components, such as surface modifications including but not limited to covalent attachment of heparin.

The stent graft components can be variously sized (i.e.: length, diameter, etc.) as suitable for an intended use, and are preferably larger in diameter than the inner vessel diameter to be treated. For example, aortic components can be oversized by approximately 10-20%; limb components can be oversized by approximately 25%.

The stent grafts of the present invention may contain any further suitable components, including but not limited to radiopaque markers to aid in visualization and to facilitate accurate placement of the stent graft. These radiopaque markers may take the form of gold bands at the distal end of each individual lumen of a given stent graft or a directional marker, for example in the shape of an "S" or any other suitable form for indicating direction and orientation of the stent graft. In addition, bi-directional anchoring hooks formed as part of the two most proximal individual stents of a given stent graft may be utilized to gain solid purchase in the non-diseased portion of a vessel wall. Further, a fixation stent may be used at the proximal end of a main body stent graft that allows for radial force fixation within the vessel in conjunction with bidirectional hooks.

Double-Barreled Stent Grafts

The double-barreled stent graft can be used for the treatment of any aneurysm of any anatomical variation or other type of diseased aorta or traumatic injury.

Visceral Double-Barreled Main Body Stent Graft and Methods for Use

Figure 1B:
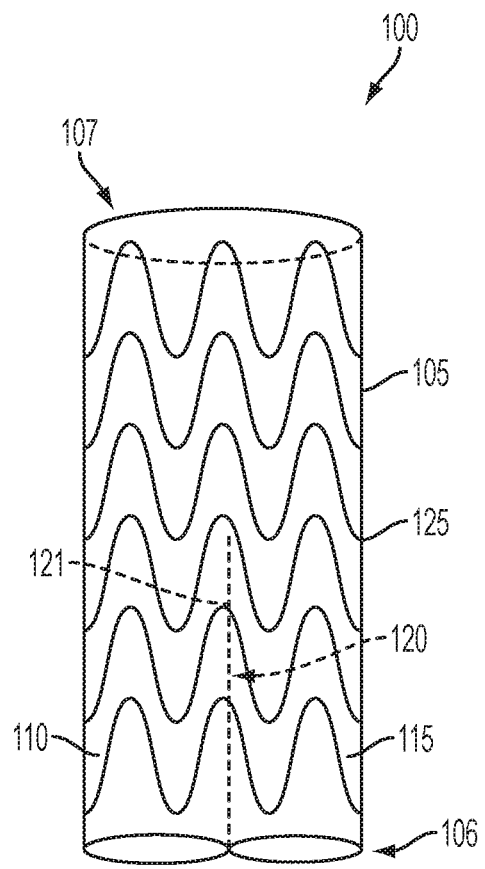
FIG. 1B is an isometric view of one embodiment of a double-barreled stent graft according to the first aspect of the invention.

In a first aspect, as exemplified in FIGS. 1A and 1B, the invention provides a stent graft 100 comprising, (a) a main body stent graft 105 having a distal end 106 and a proximal end 107, wherein the main body stent graft 105 has a length in the range from about 100 mm to about 120 mm, wherein the main body stent graft 105 has a diameter at the proximal end 107 in the range from about 30 mm to about 45 mm, (b) a first lumen 110 defined at the distal end 106 of the main body stent graft 105, wherein the first lumen 110 has a diameter in the range from about 18 mm to about 20 mm, (c) a second lumen 115 defined at the distal end 106 of the main body stent graft 105, wherein the second lumen 115 has a diameter in the range from about 16 mm to about 18 mm, wherein the first lumen 110 and the second lumen 115 have the same length of about 50 mm to about 70 mm, wherein the first lumen 110 is secured to the second lumen 115 along a shared length 120, and (d) wherein the main body stent graft 105 defines a tubular wall 125 that is contiguous with the first lumen 110 and the second lumen 115 such that any fluid entering the main body stent graft 105 must exit through one of the first lumen 110 or the second lumen 115.

In one embodiment, the double barreled main body stent graft 100 can be made by joining two existing single lumen stent graft extensions or limbs to the complete periphery of a distal end of an existing single lumen main body stent graft and then joining the two single lumen extensions and/or limbs to one another along a shared length. The main body stent graft can be joined with two existing single lumen stent grafts using adhesive, sewing, bonding, or welding, or any other known mechanism, for example. The same means can be used to join the two single lumens along a shared length. This embodiment maintains the two single lumen extensions or limbs in a substantially cylindrical configuration. In a further embodiment, the double barreled main body stent graft can be made by sewing a seam partially or completely up the middle of an existing stent graft, to create the two separate "barrels" or lumens. In another embodiment, the double barreled main body stent graft can be clamped partially or completely up the middle of an existing stent graft, to create the two separate lumens. Alternatively, the double-barreled main body stent graft can be manufactured as unitary dual lumen device using any suitable process. Using a seam or clamp technique allows the tubular wall 125 of the main body stent graft 105 to remain contiguous with the walls of first lumen 110 and the second lumen 115 such that any fluid entering the main body must exit through one of the first lumen 110 or the second lumen 115.

In a preferred embodiment, the double-barreled stent graft 100 can be used as an anchoring main body stent graft for debranching procedures.

In one embodiment, the shared length 120 of the first and second lumens is a minimum of about 30 mm. This length provides adequate overlap for passive fixation to other modular stent grafts, for example, debranching great vessel stent grafts, debranching visceral stent grafts, extension stent grafts, other stent grafts of the present invention, or any other limb-type stent graft during stent graft debranching procedures.

In one embodiment, the first lumen 110 and the second lumen 115 are defined by a seam 121 at the distal end of the main body graft. As shown in FIGS. 1B and 2B, the proximal end 107, 207 of the main body stent graft 105, 205 remains substantially cylindrical to maintain a complete seal with the aortic wall. In another embodiment, the visceral double-barreled stent graft 100, 200 further includes a cylindrical stent graft structure, discussed in detail with respect to the sixth aspect of the invention, that is coextensive with and disposed on an exterior of the main body stent graft 105, 205.

In another embodiment, the diameter of the first lumen 110 is about 2 mm greater than the diameter of the second lumen 115. In a preferred embodiment, the diameter of the first lumen 110 is about 18 mm and the diameter of the second lumen 115 is about 16 mm. In various embodiments, the diameter of the first lumen 110 may be between about 18-20 mm, 19-20 mm or 20 mm, while the diameter of the second lumen 115 may be between about 16-18 mm or about 16-17 mm.

In a further embodiment, the length of the main body stent graft 105 is about 100 mm and, in various embodiments, may be between about 100-120 mm, 100-115 mm, 100-110 mm, 100-105 mm, 105-120 mm, 110-120 mm, 115-120 mm or about 120 mm.

In various embodiments, the diameter of the proximal end of the main body stent graft may be between about 30-45 mm, 32-43 mm, 35-40 mm, 30 mm, 35 mm, 40 mm or about 45 mm.

Figure 2A:
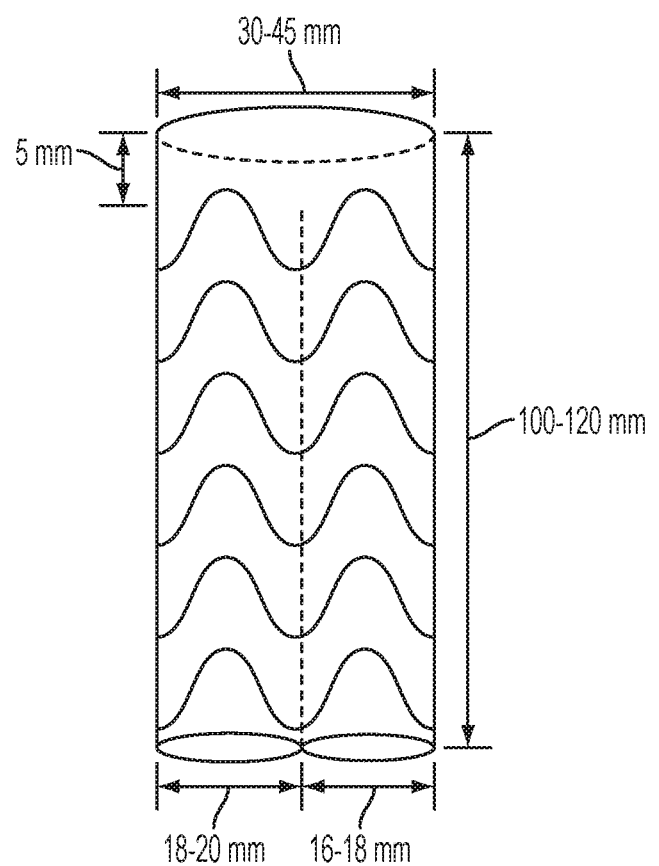
FIG. 2A is an isometric view illustrating the dimensions of one embodiment of a double-barreled stent graft according to the second aspect of the invention.
Figure 2B:
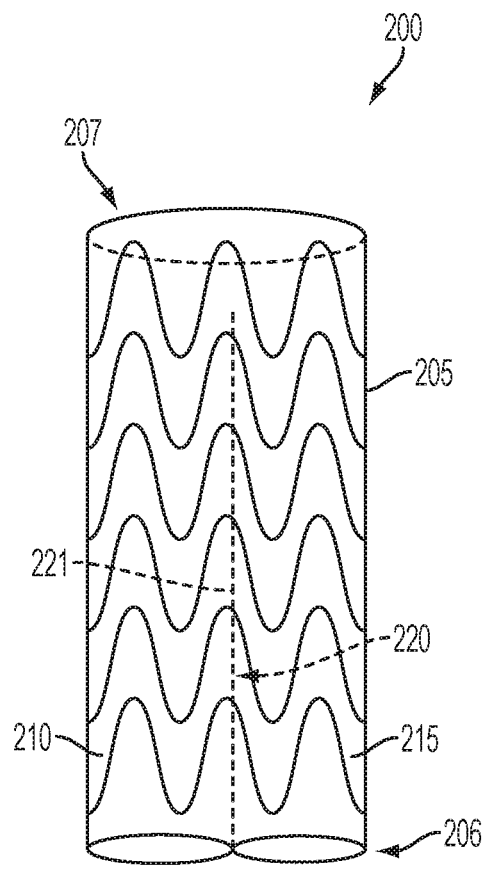
FIG. 2B is an isometric view of one embodiment of a double-barreled stent graft according to the second aspect of the invention.

In a second aspect, as shown in FIGS. 2A and 2B, the invention provides a stent graft 200 comprising, (a) a main body stent graft 205 having a distal end 206 and a proximal end 207, wherein the main body stent graft 205 has a length in the range from about 100 mm to about 120 mm, (b) a first lumen 210 defined about 5 mm from the proximal end 207 of the main body stent graft 205 to the distal end 206 of the main body 205, wherein the first lumen 210 has a substantially constant diameter along its length in the range from about 18 mm to about 20 mm, (c) a second lumen 220 defined about 5 mm from the proximal end 207 of the main body stent graft 205 to the distal end 206 of the main body stent graft 205, wherein the second lumen 215 has a substantially constant diameter along its length in the range from about 16 mm to about 18 mm, wherein the first lumen 210 is secured to the second lumen 215 along a shared length 220.

The main body stent graft 205 defines a single lumen with a uniform side wall at the proximal end 207 extending 5 mm towards the distal end 206 to ensure that the profile of the proximal end 207 remains substantially cylindrical to maintain a complete seal with the aortic wall.

Any of the additional embodiments discussed with respect to the first aspect of the invention can likewise be used with the second aspect of the invention.

Figure 3:
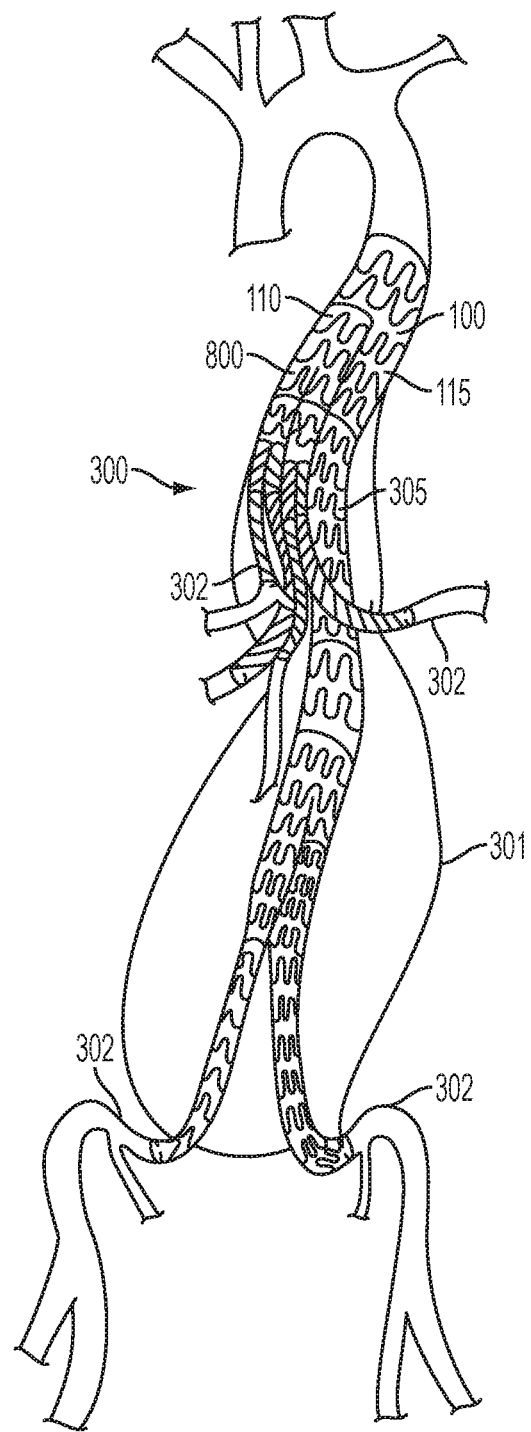
FIG. 3 is a cross-sectional view of a thoracic abdominal aortic aneurysm with an isometric view of one embodiment of a double-barreled stent graft, a debranching visceral stent graft and multiple stent graft extenders after deployment during a debranching procedure.

In a third aspect, see for example FIG. 3, the invention provides a method for placement of a stent graft 100, 200 according to the first or second aspects of the invention, comprising, (a) introducing a guidewire into an aorta 300 via arterial access, (b) loading a delivery catheter containing a stent graft 100, 200 according to the first or second aspects of the invention onto the guidewire, (c) moving the delivery catheter along the guidewire and introducing the delivery catheter into the aorta 300 via arterial access, and (d) deploying the stent graft 100, 200 into the aorta 300.

In one example, FIG. 3 shows a visceral double-barreled main body stent graft 100 acting as a platform or anchor. A debranching visceral stent graft 800 is deployed within the first lumen 110 of the double-barreled main body stent graft 100 and a visceral extension stent graft 305 is deployed within the second lumen 115. Additional extension stent grafts and a bifurcated stent graft are linked in series across the aneurysmal sac 301 to the native vessels 302 to complete the debranching of the aneurysm.

In one embodiment, the visceral double-barreled stent grafts 100, 200 may be used in an antegrade deployment in the thoracic aorta in the normal direction of blood flow. In an example visceral antegrade deployment, the distal portion of the stent graft can be placed about 11 cm above the celiac artery. In this antegrade deployment, one of the first or second lumens of the double-barreled stent grafts is dedicated to the visceral segment of the aorta, while the other lumen is dedicated to the revascularization of the infra-renal aorta.

In a fourth aspect, not shown, the invention provides a method for placement of a stent graft 100, 200 according to the first or second aspects of the invention, comprising, (a) introducing a guidewire into an aortic arch via arterial access, (b) loading a delivery catheter containing a stent graft 100, 200 according to the first or second aspects of the invention onto the guidewire, wherein a distal end 106, 206 of the stent graft is loaded first, (c) moving the delivery catheter along the guidewire and introducing the delivery catheter into the aortic arch via arterial access, and (d) deploying the stent graft 100, 200 into a proximal descending aorta.

In a fifth aspect, not shown, the invention provides a method for placement of a stent graft 100, 200 according to the first or second aspects of the invention, comprising, (a) introducing a guidewire into a thoracic or abdominal aorta via arterial access, (b) loading a delivery catheter containing a stent graft 100, 200 according to the first or second aspects of the invention onto the guidewire, (c) moving the delivery catheter along the guidewire and introducing the delivery catheter into the thoracic or abdominal aorta via arterial access, and (d) deploying the stent graft 100, 200 into the thoracic or abdominal aorta.

In one embodiment, a main body of a debranching stent graft is sized so as to slide into one of the lumens of the double-barreled main body stent graft, while the other lumen can be used for stenting of a lower extremity, such as the infrarenal segment. In one embodiment, he debranching stent graft is held in place through passive fixation.

Aortic Arch Double-Barreled Main Body Stent Graft and Methods for Use

Figure 4A:
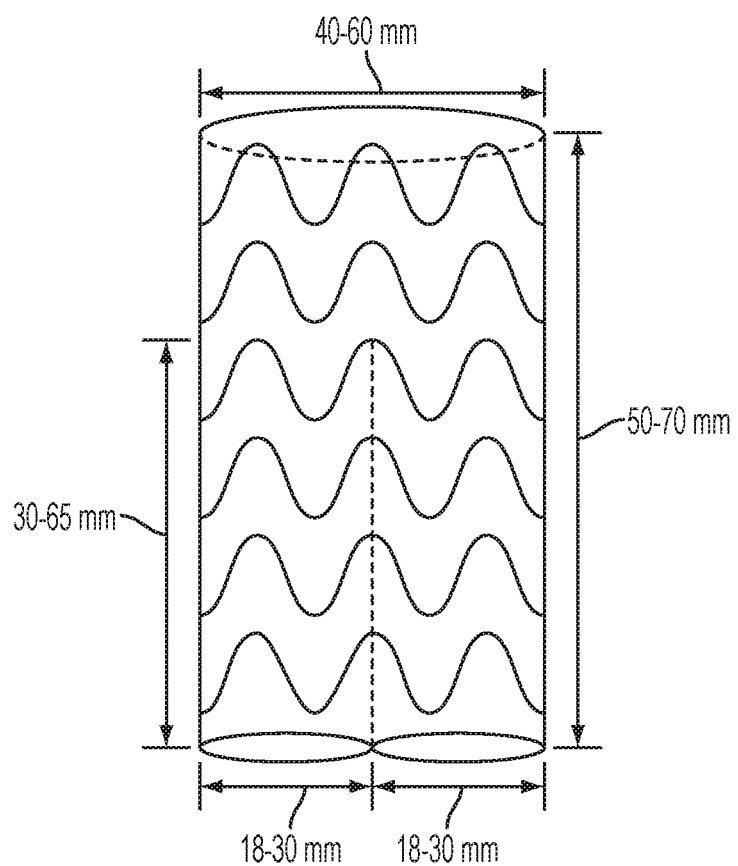
FIG. 4A is an isometric view illustrating the dimensions of one embodiment of a double-barreled stent graft according to the sixth aspect of the invention.
Figure 4B:
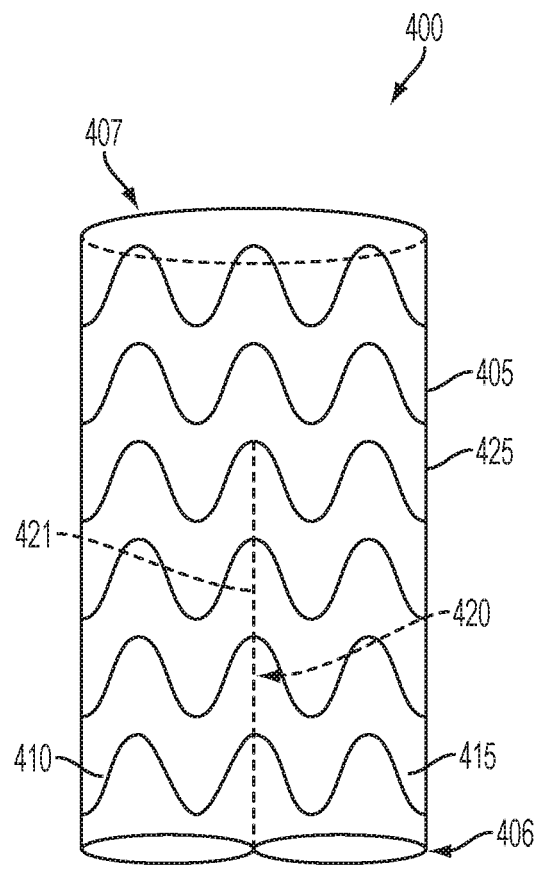
FIG. 4B is an isometric view of one embodiment of a double-barreled stent graft according to the sixth aspect of the invention.

In a sixth aspect, as shown in FIGS. 4A and 4B, the invention provides a stent graft 400 comprising, (a) a main body stent graft 405 having a distal end 406 and a proximal end 407 wherein the main body stent graft 405 has a length in the range from about 50 mm to about 70 mm, wherein the main body stent graft 405 has a diameter at the proximal end 407 in the range from about 40 mm to about 60 mm, (b) a first lumen 410 defined at the distal end of the main body stent graft 405, wherein the first lumen 410 has a diameter in the range from about 18 mm to about 30 mm, (b) a second lumen 415 defined at the distal end 406 of the main body stent graft 405, wherein the second lumen 415 has a diameter in the range from about 18 mm to about 30 mm, (c) wherein the first lumen 410 is secured to the second lumen 415 along a shared length 420, wherein the shared length of the first lumen 410 and the second lumen 415 is in the range from about 30 mm to about 65 mm, and (d) wherein the main body stent graft 405 defines a tubular wall 425 that is contiguous with the first lumen 410 and the second lumen 415 such that any fluid entering the main body stent graft 405 must exit through one of the first lumen 410 or the second lumen 415.

In one embodiment, the double barreled main body stent graft 400 can be made by joining two existing single lumen stent graft extensions or limbs to the complete periphery of a distal end of an existing single lumen main body stent graft and then joining the two single lumen extensions and/or limbs to one another along a shared length. The main body stent graft can be joined with two existing single lumen stent grafts using adhesive, sewing, bonding, or welding, or any other known mechanism, for example. The same means can be used to join the two single lumens along a shared length. This embodiment maintains the two single lumen extensions or limbs in a substantially cylindrical configuration. In a further embodiment, the double barreled main body stent graft can be made by sewing a seam partially or completely up the middle of an existing stent graft, to create the two separate "barrels" or lumens. In another embodiment, the double barreled main body stent graft can be clamped partially or completely up the middle of an existing stent graft, to create the two separate lumens. Alternatively, the double-barreled main body stent graft can be manufactured as unitary dual lumen device using any suitable process. Using a seam or clamp technique allows the tubular wall 425 of the main body stent graft 405 to remain contiguous with the walls of first lumen 410 and the second lumen 415 such that any fluid entering the main body must exit through one of the first lumen 410 or the second lumen 415.

In one embodiment of the sixth aspect of the invention, the first lumen and the second lumen are defined by a seam 421 starting at the distal end 406 of the main body stent graft 405 and extending towards the proximal end 407 of the main body stent graft 405. In one preferred embodiment, the shared length 421 of the first lumen 410 and the second lumen 415 is about 30 mm and, in various embodiments, the shared length 421 may be between about 30-65 mm, 30-60 mm, 30-55 mm, 30-50 mm, 30-45 mm, 30-40 mm or 30-35 mm. Alternatively, the shared length 421 of the first lumen 410 and the second lumen 415 is about 70 mm.

In various embodiments, the length of the main body stent graft 405 may be between about 50-70 mm, 50-65 mm, 50-60 mm, 50-55 mm, 50 mm, 55-70 mm, 60-70 mm, 65-70 mm or about 70 mm.

In one embodiment, the diameter of the first lumen 410 is about the same as the diameter of the second lumen 415. In one preferred embodiment, the diameter of the first lumen 410 is about 20 mm and the diameter of the second lumen 415 is about 20 mm. In various embodiments, the diameter of the first lumen 410 may be between about 18-30 mm, 20-28 mm, 22-26 mm, or 24 mm. In various embodiments, the diameter of the second lumen 415 may be between about 18-30 mm, 20-28 mm, 22-26 mm or about 24 mm.

In another preferred embodiment, the main body stent graft 405 has a diameter at the proximal end 406 of about 40 mm. In still another preferred embodiment, the length of the main body stent graft 405 is about 50 mm and, in various embodiments, the length of the main body stent graft 405 may be between about 40-60 mm, 42-58 mm, 44-56 mm, 46-54 mm, 48-52 mm, 40 mm or about 60 mm.

Figure 5A:
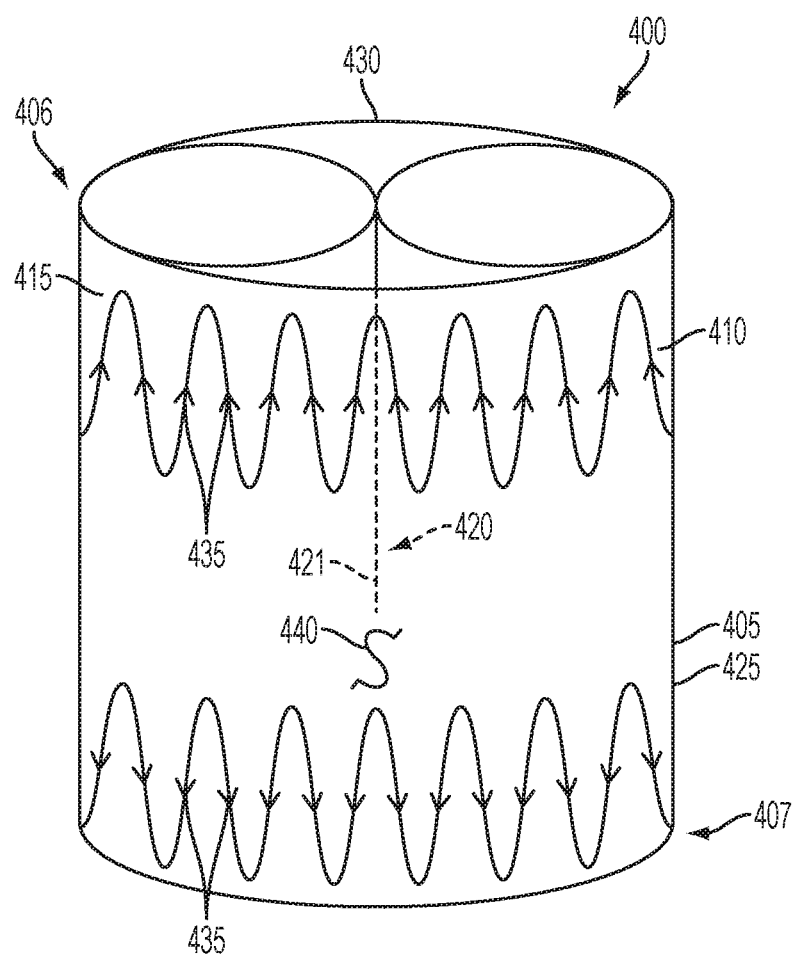
FIG. 5A is an isometric view of one embodiment of a double-barreled stent graft according to the sixth aspect of the invention with a cylindrical stent graft structure disposed on an exterior of the main body stent graft.

In another embodiment, as shown in FIG. 5A, the sixth aspect of the invention further comprises a cylindrical stent graft structure 430 coextensive with and disposed on an exterior of the main body stent graft 405. The cylindrical stent graft structure 430 maintains the double-barreled stent graft 400 in a substantially cylindrical shape to assist with facial contact with the vessel wall along the length of the stent graft resulting in a complete circumferential seal and to ensure blood flow is maintained through both lumens 410, 415. When the double-barreled stent graft 400 is deployed in the ascending aorta or the proximal descending aorta, maintaining the cylindrical shape of the double-barreled stent graft 400 is particularly important.

In one embodiment, the cylindrical stent graft structure 430 may further define bi-directional anchor hooks 435. These bi-directional anchor hooks 435 attach to the aortic wall preventing or limiting migration of the main body stent graft 405 within the aorta.

In another embodiment, the cylindrical stent graft structure 430 may further include radiopaque markers 440 in the form of gold bands at the distal end of each individual lumen of a given stent graft. These radiopaque markers 440 help the surgeon ensure that the double-barreled stent graft 400 is properly oriented within the aorta prior to deployment and further assist with guidewire placement within the first and/or second lumens 410, 415.

In yet another embodiment, the cylindrical stent graft structure 430 may further include a directional marker 445 of any shape or configuration, for example, an "S" shape. The directional marker 445 helps the surgeon ensure that the double-barreled stent graft 400 is properly oriented within the aorta prior to deployment.

Figure 5B:
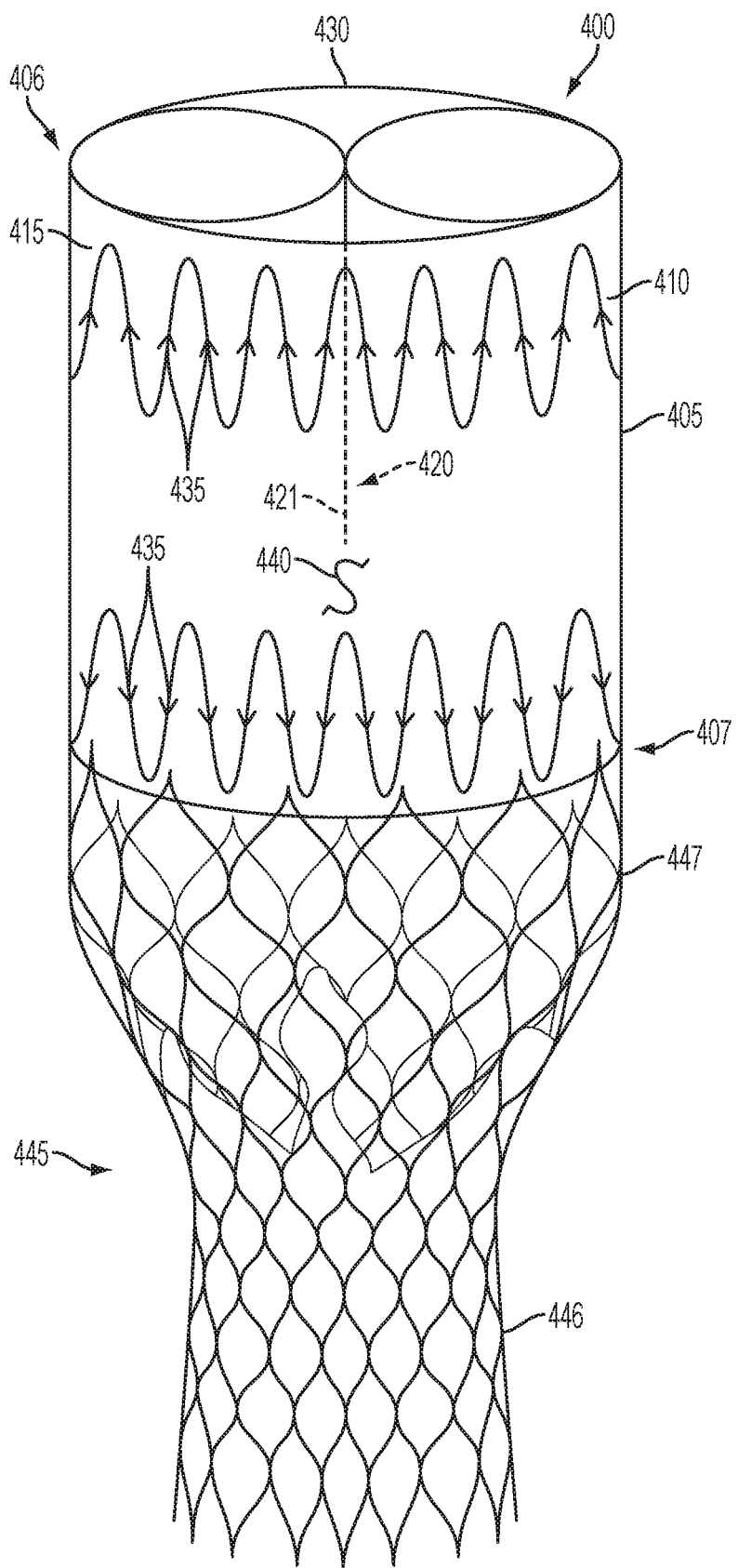
FIG. 5B is an isometric view of one embodiment of a double-barreled stent graft according to the sixth aspect of the invention with a cylindrical stent graft structure disposed on an exterior of the main body stent graft and a stent valve attached to the proximal end of the main body stent graft.

In one embodiment, shown in FIG. 5B, a stent valve 445 is affixed to the proximal end 407 of the main body stent graft 405, where a free end 446 of the stent valve 445 is covered and a portion of the stent valve 447 extending between the free end 446 and the proximal end 407 of the main body stent graft 405 is uncovered. As used herein, a "stent valve" is a percutaneous self-expanding valve affixed to a proximal end 407 of the main body stent graft 405 with the uncovered portion 447 overlaying the coronary arteries 455 to maintain blood flow. An exemplary embodiment of the stent valve includes the Corevalve® manufactured by Medtronic. In one embodiment, the free end 446 of the stent valve 445 is covered with an impervious natural or synthetic material. In one embodiment, the stent valve 445 may be placed in the outflow tract 451 of the aortic valve. The stent valve's anchoring mechanism is derived from, for example, a funnel shape with a larger diameter at the free end 446 and smaller diameter at the point where the covered portion meets the uncovered portion 447. This embodiment may be used in combination with any of the anchoring main body stent grafts of the present invention.

In a seventh aspect, the invention provides a method for placement of a stent graft 400 from the sixth aspect of the invention, comprising, (a) introducing a guidewire into an aorta via arterial access, (b) loading a delivery catheter containing a stent graft 400 according to the sixth aspect of the invention onto the guidewire, (c) moving the delivery catheter along the guidewire and introducing the delivery catheter into the aorta via arterial access, and (d) deploying the stent graft 400 into the aorta.

In one embodiment, the seventh aspect further comprises (e) loading a second delivery catheter containing a debranching stent graft 1100 according to the thirteenth aspect of the invention onto the guidewire, (f) moving the second delivery catheter along the guidewire and introducing the delivery catheter into the aorta via arterial access, and (g) deploying the debranching stent graft 1100 into one of the aorta or a lumen of a previously-placed stent graft, such as a stent graft 400 according to the sixth aspect of the invention within the aorta.

In one embodiment, a main body of the debranching stent graft 1100 is sized so as to slide into one of the lumens of the double-barreled main body stent graft 400, while the other lumen can be used an extension stent graft. In one embodiment, the debranching stent graft 1100 and extension stent graft are held in place through passive fixation.

In another embodiment, the seventh aspect still further comprises, (h) introducing a second guidewire into the aorta via arterial access, (i) loading a third delivery catheter containing a great vessel limb 1325 according to the thirteenth aspect of the invention onto the second guidewire, (j) moving the third delivery catheter along the second guidewire and introducing the third delivery catheter into a selected leg of the debranching stent graft 1100 via arterial access, and (k) deploying a proximal end 1326 of the great vessel limb 1325 into the selected leg of the debranching stent graft 1100.

In an eighth aspect, the invention provides a method for placement of a stent graft 400 from the sixth aspect of the invention, comprising, (a) introducing a guidewire into an aortic arch via arterial access, (b) loading a delivery catheter containing a stent graft 400 according to the sixth aspect of the invention onto the guidewire, wherein a distal end 406 of the stent graft 405 is loaded first, (c) moving the delivery catheter along the guidewire and introducing the delivery catheter into the aortic arch via arterial access, and (d) deploying the stent graft 400 into a proximal descending aorta.

In another embodiment, the aortic arch double-barreled stent graft may be used in a retrograde deployment in the aortic arch against the normal direction of blood flow. In the retrograde deployment, the proximal portion of the stent graft can be placed about 11 cm distal to the left subclavian artery. In this retrograde deployment, one of the first or second lumens is dedicated to the Great vessels, while the other lumen is dedicated to the ascending aorta.

Figure 6:
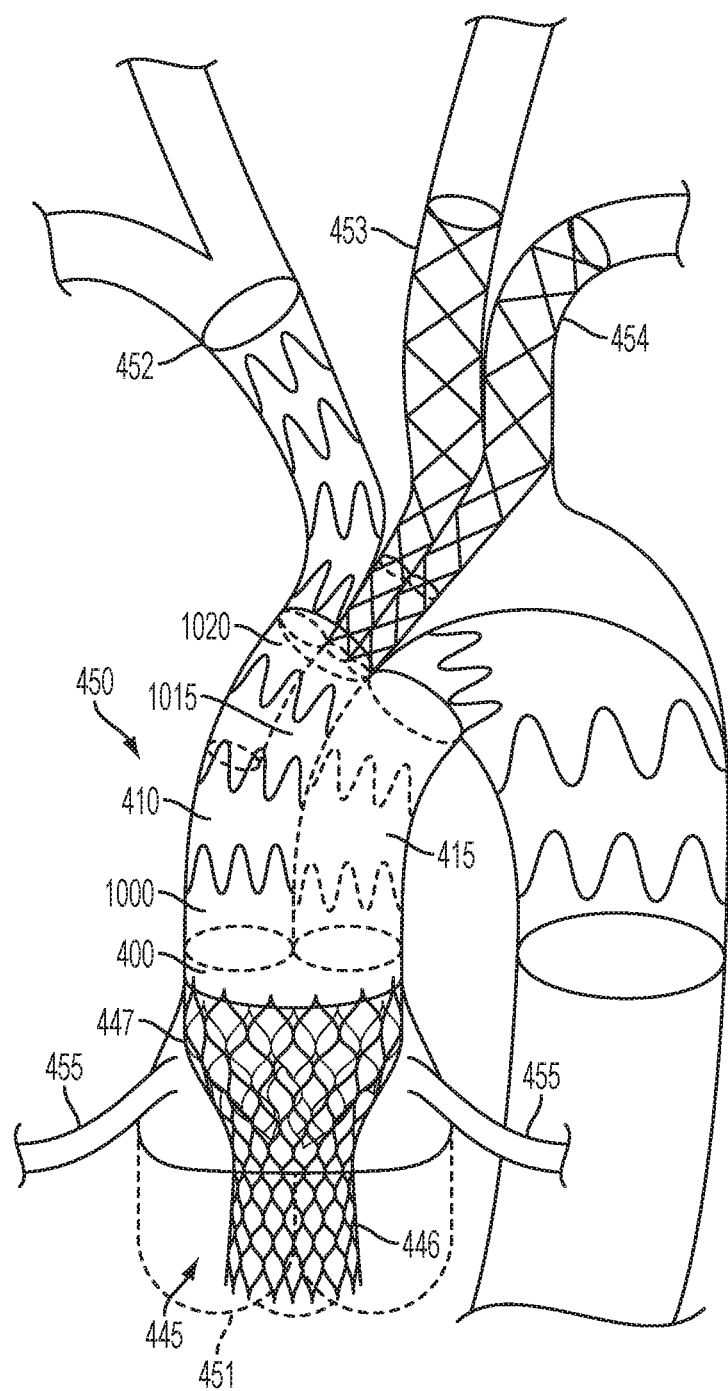
FIG. 6 is a cross-sectional view of the ascending aorta and the proximal descending aorta with an isometric view of one embodiment of a double-barreled stent graft including a stent valve, a debranching visceral stent graft and multiple stent graft extenders after deployment during a debranching procedure.

In a ninth aspect, as shown in FIG. 6, the invention provides a method for placement of a stent graft 400 from the sixth aspect of the invention, comprising, (a) introducing a guidewire into an ascending aorta 450 via arterial access, (b) loading a delivery catheter containing a stent graft 400 according to the sixth aspect of the invention onto the guidewire, (c) moving the delivery catheter along the guidewire and introducing the delivery catheter into the ascending aorta 450 via arterial access, and (d) deploying the stent graft 400 into one or both of an aortic outflow tract 451 or the ascending aorta 450.

In one embodiment, the double-barreled stent graft 400 may be used in an antegrade deployment in the ascending aorta 450 in the normal direction of blood flow. This is considered a "transapical" approach. As used herein, the "transapical" approach is made through the left ventricle through an apex of the heart into the ascending aorta 450 in order to debranch the aortic arch in an antegrade manner. Specifically, the double barrel stent graft 400 is loaded in a catheter in reverse and deployed antegrade. In this transapical antegrade deployment, the proximal portion of the double-barreled stent graft 400 is deployed within about one centimeter of the aortic valve coronary arteries 455. In the embodiment utilizing a stent valve 445, the free covered end 446 of the stent valve lies in the aortic outflow tract 451, while the uncovered portion 447 of the stent valve lays across the coronary arteries 455 permitting blood flow to continue in a normal manner. According to this transapical antegrade deployment, one of the first or second lumens 410, 415 of the double-barreled stent graft 400 is dedicated to the innominate artery 452, while the other lumen is dedicated to the left common carotid 453 and the left subclavian arteries 454.

Debranching Stent Grafts

The debranching stent grafts can be used for the treatment of any aneurysm of any anatomical variation or other type of diseased aorta or traumatic injury. The debranching stent grafts, in particular, are able to connect to almost any vessel anatomy, and thus provide an ease of use in a variety of different patients. In addition, the debranching stent graft can be used in combination with any embodiment of the double-barreled stent graft or stent graft limb disclosed herein, or other main body anchoring stent graft. The core debranching stent graft comprises a main body stent graft with a bifurcation defining a first leg and a second leg. This core can be used modularly with limbs that may be selected based on the debranching procedure required and a given patient's vasculature.

Debranching Visceral Stent Graft and Methods for Use

In a tenth aspect, as shown in FIGS. 7A-9B, the invention provides a debranching stent graft 700, 800, 900 comprising, (a) a main body stent graft 705, 805, 905 with a bifurcation 710, 810, 910 defining a first leg 715, 815, 915 and a second leg 720, 820, 920, wherein the main body stent graft 705, 805, 905 has a distal end 706, 806, 906 and a proximal end 707, 807, 907, (b) wherein the main body stent graft 705, 805, 905 has a diameter at the proximal end 707, 807, 907 in the range from about 18 mm to about 22 mm, (c) wherein the first leg 715, 815, 915 and the second leg 720, 820, 920 each have a diameter in the range from about 14 mm to about 16 mm, (d) wherein the distance from the proximal end 707, 807, 907 of the main body stent graft 705, 805, 905 to the distal end 706, 806, 906 of the first leg 715, 815, 915 is in the range from about 70 mm to about 90 mm, (e) and wherein the distance from the proximal end 707, 807, 907 of the main body stent graft 705, 805, 905 to the distal end 721, 821, 921 of the second leg 720, 820, 920 is in the range from about 80 mm to about 100 mm, and wherein the second leg 720, 820, 920 is at least about 10 mm longer than the first leg 715, 815, 915. Like numbers denote like features in FIGS. 7A-9B.

The debranching visceral stent graft 700 may be deployed within a lumen of a double-barreled main body stent graft as a second level in a debranching procedure or placed in direct contact with a vessel wall as an anchoring main body stent graft. In addition, the debranching visceral stent graft 700, 800, 900 could be deployed in the lumen of any previously-placed appropriately sized stent graft.

In one preferred embodiment, the second leg 720, 820, 920 is no more than about 20 mm longer than the first leg 715, 815, 915. The difference in length between the two legs allows for a smaller constraining device to be used for deployment and further eases selection of the individual vessels for stenting by providing a better radiographical visualization of the legs. In a further preferred embodiment, the distance from the proximal end 707, 807, 907 of the main body stent graft 705, 805, 905 to the distal end 706, 806, 906 of the first leg 715, 815, 915 is about 70 mm, and the distance from the proximal end 707, 807, 907 of the main body stent graft 705 to the distal end of the second leg 720 is about 80 mm. In various embodiments, the distance from the proximal end 707, 807, 907 of the main body stent graft 705, 805, 905 to the distal end 706, 806, 906 of the first leg 715, 815, 915 may be between about 70-90 mm, 70-85 mm, 70-80 mm or 70-75 mm. In various embodiments, the distance from the proximal end 707, 807, 907 of the main body stent graft 705, 805, 905 to the distal end of the second leg 720, 820, 920 may be between about 80-100 mm, 80-95 mm, 80-90 mm or 80-85 mm.

In another preferred embodiment, the bifurcation 710, 810, 910 occurs in the range from about 30 mm to about 40 mm from the proximal end 707, 807, 907. This provides 30-40 mm for passive fixation with a lumen of an anchoring double-barreled main body stent graft 100, 200 or any other anchoring stent graft and/or 30-40 mm of substantially cylindrical wall at the proximal end 707, 807, 907 of the main body stent graft 705, 805, 905 for direct facial contact with the aortic wall when the debranching visceral stent graft 700, 800, 900 is acting as a main body anchor.

In an additional preferred embodiment, the diameter of the main body stent graft 705, 805, 905 at the proximal end 707, 807, 907 is about 20 mm and, in various embodiments, may be between about 18-22 mm, 19-22 mm, 20-22 mm, 21-22 mm or about 22 mm.

In one embodiment, the tenth aspect of the invention further comprises a first visceral limb 725, 825, 925 joined with one of the first leg 715, 815, 915 or the second leg 720, 820, 920 at the distal end of the main body stent graft 705, 805, 905.

In a preferred embodiment, as shown in FIGS. 8A-9B, the first visceral limb 825, 925 is joined with one of the first leg 815, 915 or the second leg 820, 920 via a seam 831, 931. In this embodiment, the first visceral limb 825, 925 preferably has a diameter at the proximal end 826, 926 of about 14 mm and, in various embodiments, may be between about 14-16 mm or 14-15 mm. Further in this embodiment, the first visceral limb 825, 925 preferably has a length in the range from about 30 mm to about 50 mm and, in various embodiments, may be between about 30-45 mm, 30-40 mm, 30-35 mm or about 30 mm. Also in this embodiment, the first visceral limb 825, 925 may have a bifurcation 830, 930 defining a third leg 835, 935 and a fourth leg 840, 940, and the bifurcation 830, 930 preferably occurs approximately at the seam. Here, each of the third leg 835, 935 and the fourth leg 840, 940 preferably have a diameter of about 7 mm. In a further preferred embodiment, as shown for example in FIGS. 8A and 8B, the tenth aspect of the invention further comprises a second visceral limb 845, 945 attached to the other of the first leg 815, 915 or the second leg 820, 920. In this embodiment, the second visceral limb 845, 945 can take the form of any embodiment of the first limb 725, 825, 925 discussed throughout.

In another preferred embodiment, the first visceral limb 725 is joined with one of the first leg 715 or the second leg 720 via passive fixation. In this embodiment, the first visceral limb 725 preferably has a diameter at the proximal end 726 in a range from about 15 mm to about 17 mm and, in various embodiments, may be between about 15-16 mm, 16-17 mm or about 15 mm. The diameter at the proximal end 726 of the visceral limb 725 should be at least about 1 mm larger than the diameter of the leg that receives the limb and the length of the overlap between the leg and limb should be at least 30 mm in order for passive fixation to be effective.

Figure 7A:
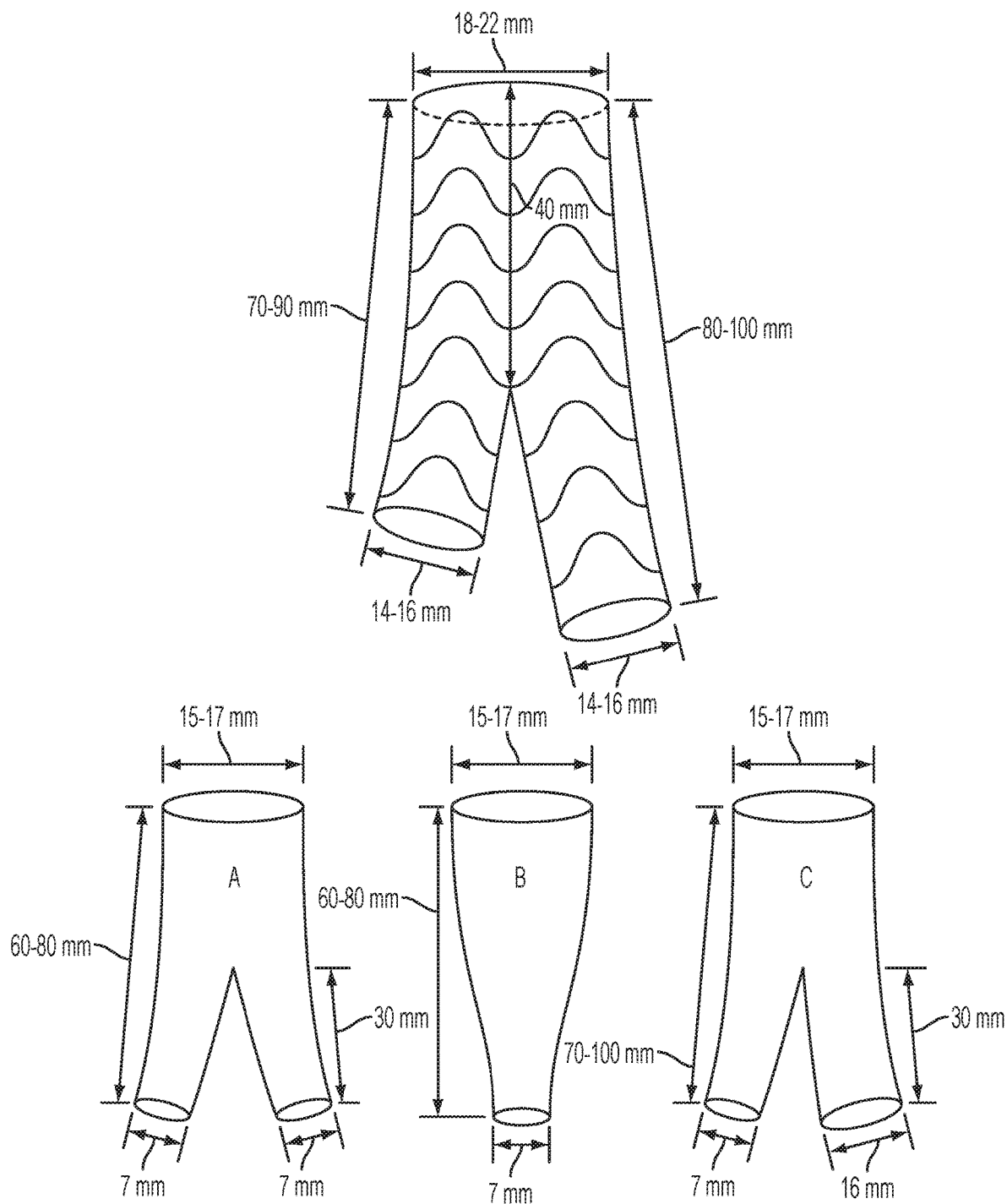
FIG. 7A is an isometric view illustrating the dimensions of one embodiment of a debranching visceral stent graft according to the tenth aspect of the invention as well as example modular visceral limbs coupled with passive fixation, for example.
Figure 7B:
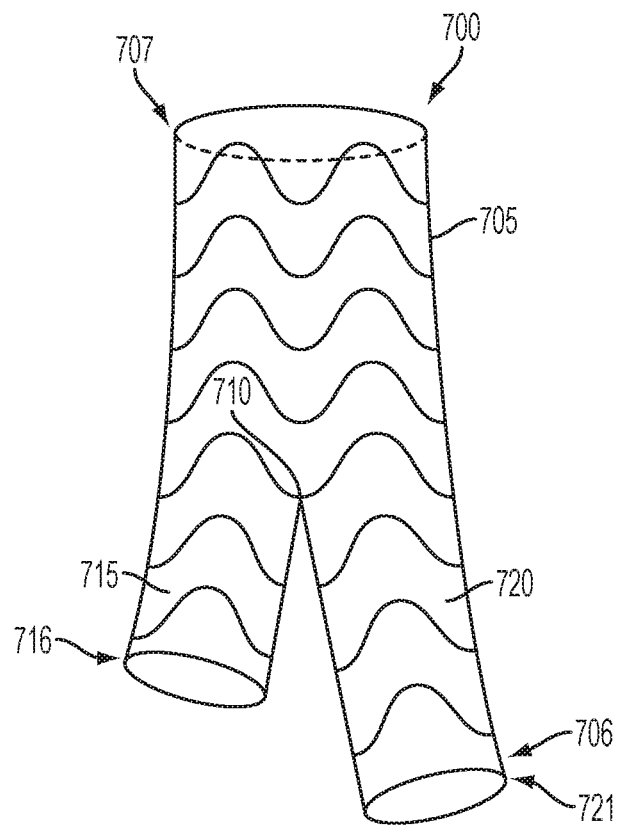
FIG. 7B is an isometric view of one embodiment of a debranching visceral stent graft according to the tenth aspect of the invention as well as example modular visceral limbs coupled with passive fixation, for example.
Figure 7B:
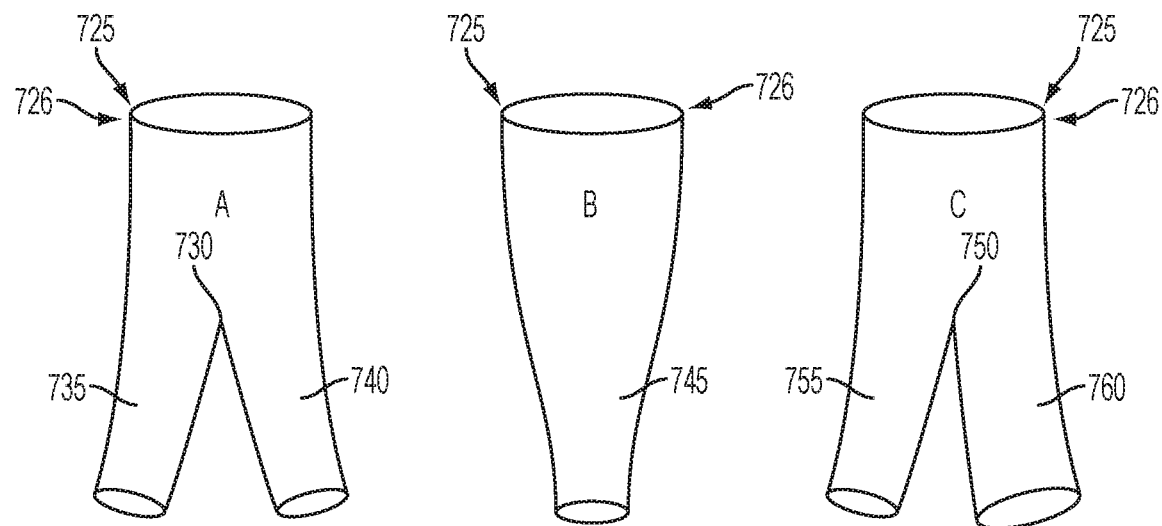
Figure 8A:
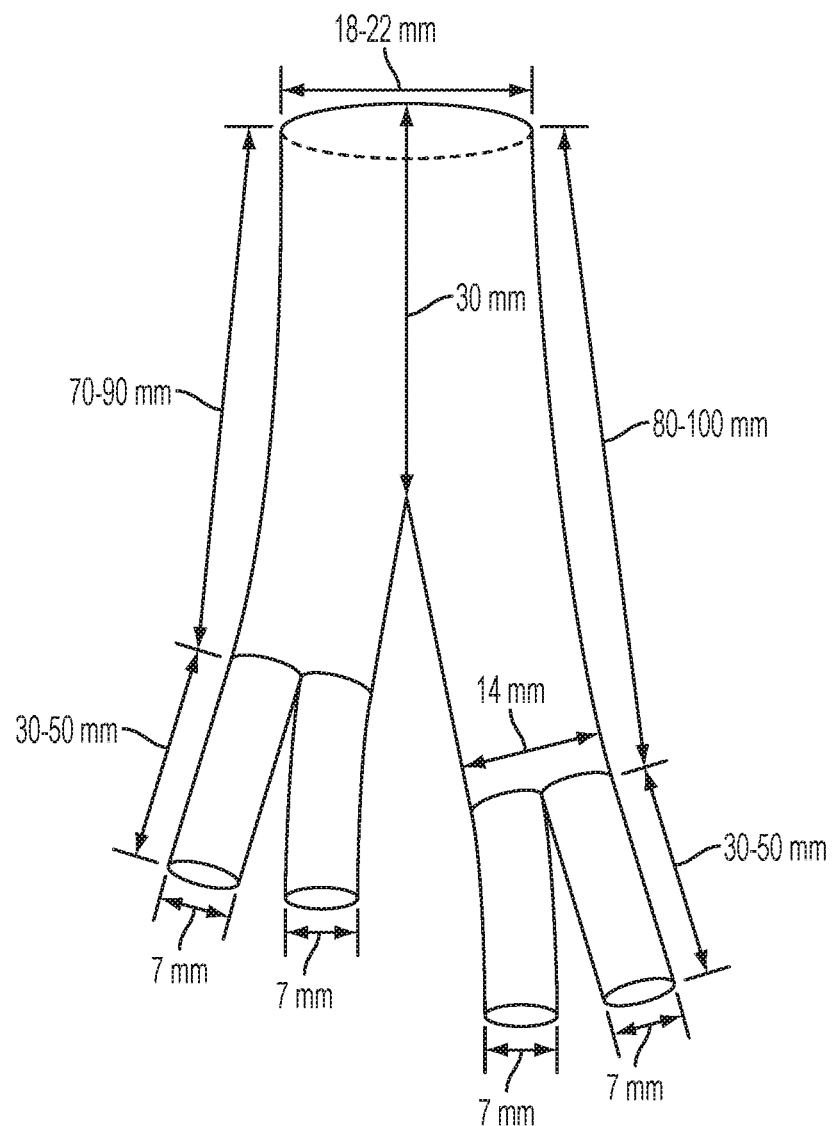
FIG. 8A is an isometric view illustrating the dimensions of one embodiment of a debranching visceral stent graft according to the tenth aspect of the invention with visceral limbs in a unitary configuration.
Figure 8B:
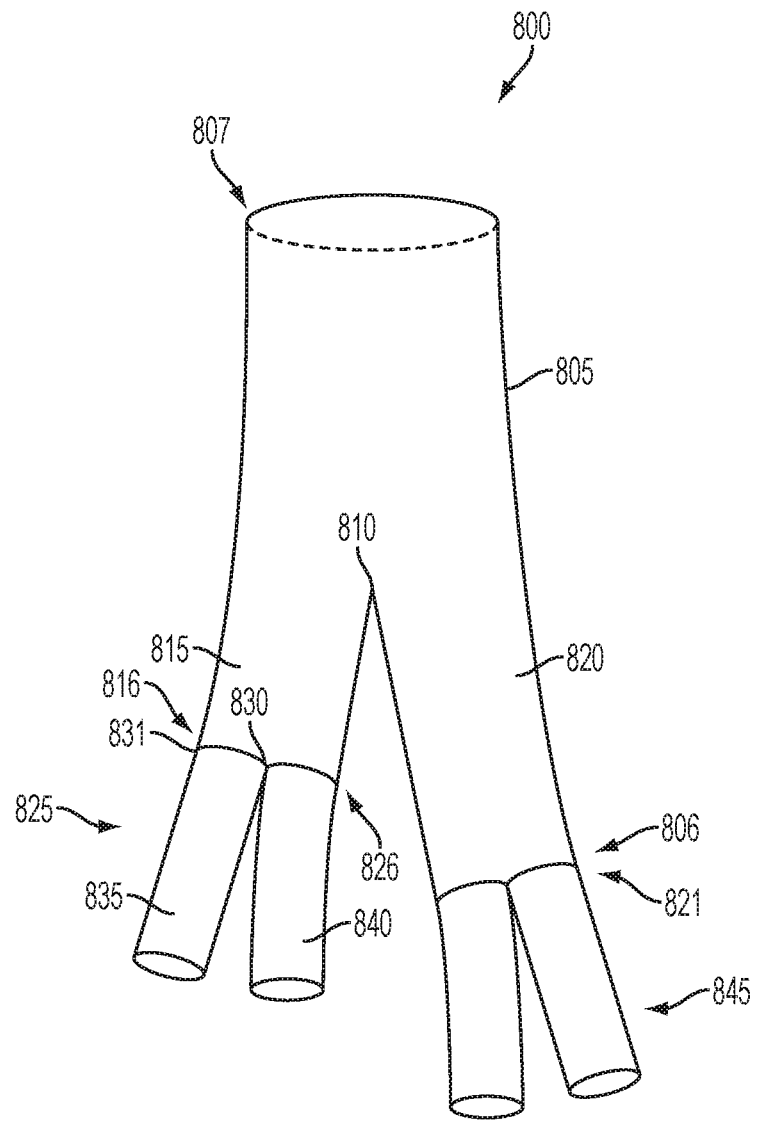
FIG. 8B is an isometric view of one embodiment of a debranching visceral stent graft according to the tenth aspect of the invention with visceral limbs in a unitary configuration.
Figure 9A:
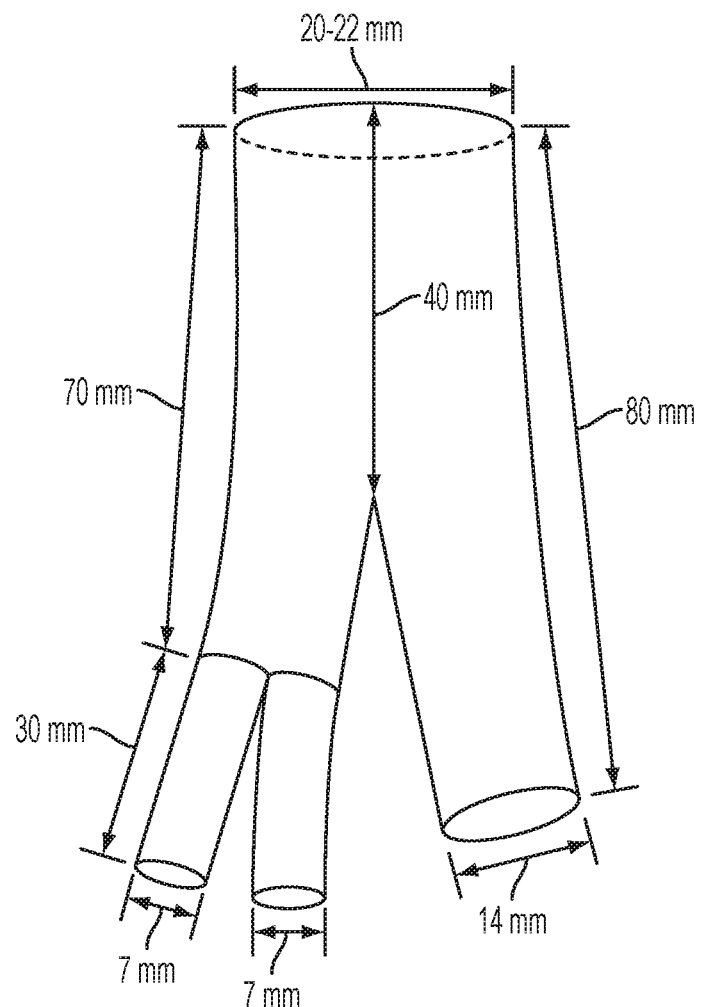
FIG. 9A is an isometric view illustrating the dimensions of one embodiment of a debranching visceral stent graft according to the tenth aspect of the invention with a visceral limb in a unitary configuration.
Figure 9B:
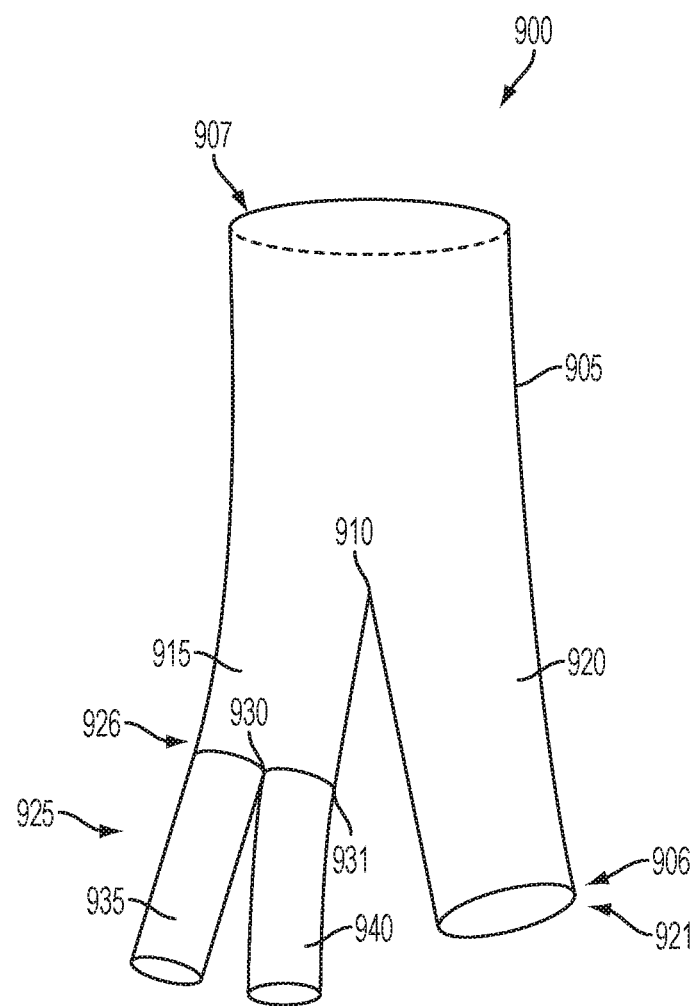
FIG. 9B is an isometric view of one embodiment of a debranching visceral stent graft according to the tenth aspect of the invention with a visceral limb in a unitary configuration.

In one passive fixation embodiment, shown in FIG. 7A, Detail A and 7B, Detail A, the first visceral limb 725 preferably has a length in the range from about 60 mm to about 80 mm and, in various embodiments, may be between about 60-75 mm, 60-70 mm, 60-65 mm, 60 mm, 65-80 mm, 70-80 mm, 75-80 mm or about 80 mm. In a further embodiment, the first visceral limb 725 may have a bifurcation 730 defining a third leg 735 and a fourth leg 740, and the third leg 735 and the fourth leg 740 preferably each have a length of about 30 mm. In still another embodiment, each of the third leg 735 and the fourth leg 740 preferably have a diameter of about 7 mm.

In another passive fixation embodiment, shown in FIG. 7A, Detail B and 7B, Detail B, the first visceral limb 725 preferably has a length in the range from about 60 mm to about 80 mm and, in various embodiments, may be between about 60-75 mm, 60-70 mm, 60-65 mm, 60 mm, 65-80 mm, 70-80 mm, 75-80 mm or about 80 mm. In a further embodiment, the first visceral limb 725 defines a single lumen 745, and the first visceral limb 725 preferably has a diameter at the distal end 746 of about 7 mm.

In a further passive fixation embodiment, shown in FIG. 7A, Detail C and 7B, Detail C, the first visceral limb 725 has a length in the range preferably from about 70 mm to about 100 mm and, in various embodiments, may be between about 70-95 mm, 70-90 mm, 70-85 mm, 70-80 mm, 70-75 mm, 70 mm, 75-100 mm, 80-100 mm, 85-100 mm, 90-100 mm, 95-100 mm or about 100 mm. In a further embodiment, the first visceral limb 725 has a bifurcation 750 defining a third leg 755 and a fourth leg 760, and the third leg 755 and the fourth leg 760 preferably each have a length of about 30 mm. In yet a further embodiment, the third leg 755 preferably has a diameter of about 7 mm and the fourth leg 760 preferably has a diameter of about 16 mm.

Each of the foregoing visceral limb 725 embodiments can be used interchangeably with the first or second leg 715, 720 of the debranching stent graft 700.

Figure 10A:
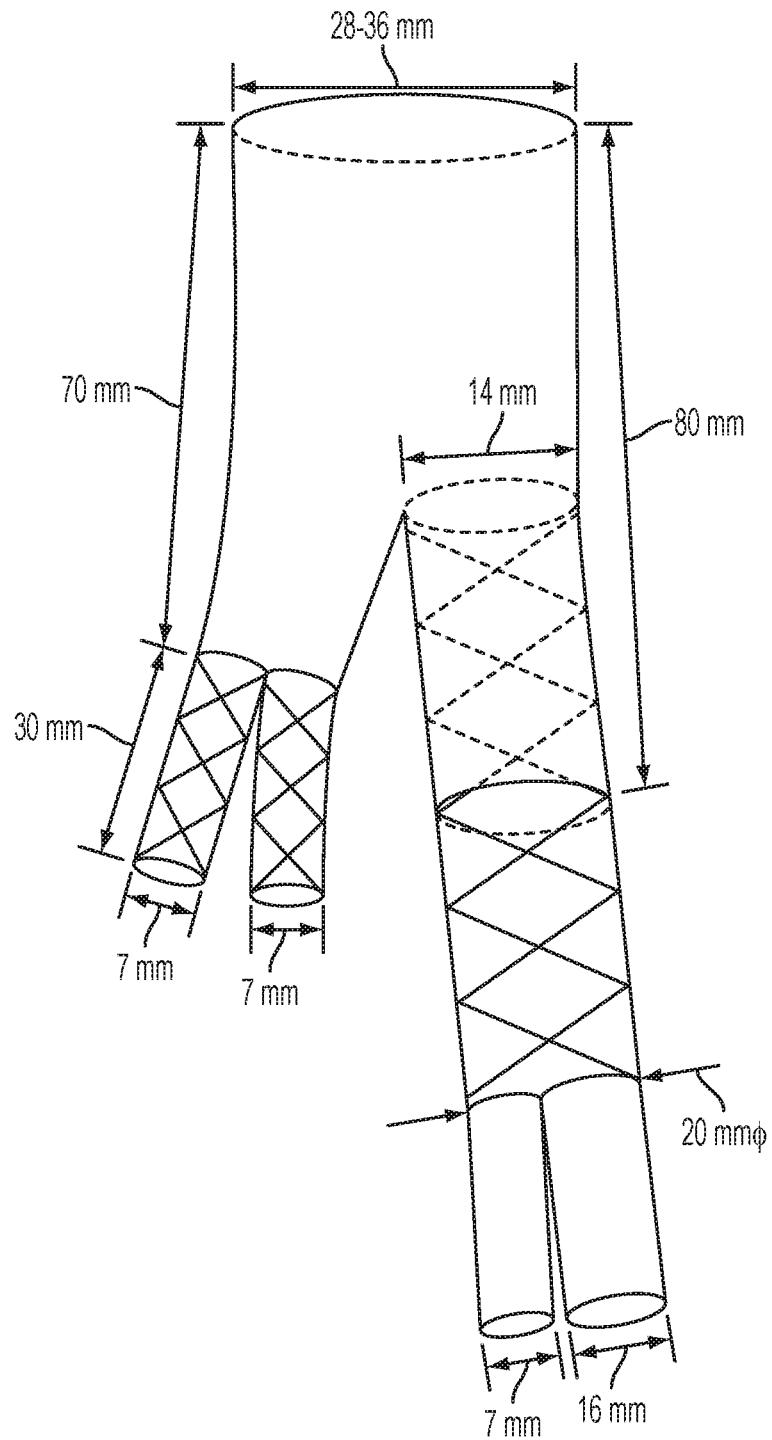
FIG. 10A is an isometric view illustrating the dimensions of one embodiment of a debranching visceral stent graft according to the eleventh aspect of the invention with a visceral limb joined to the first leg in a unitary configuration and a visceral extension deployed within the second leg.
Figure 10B:
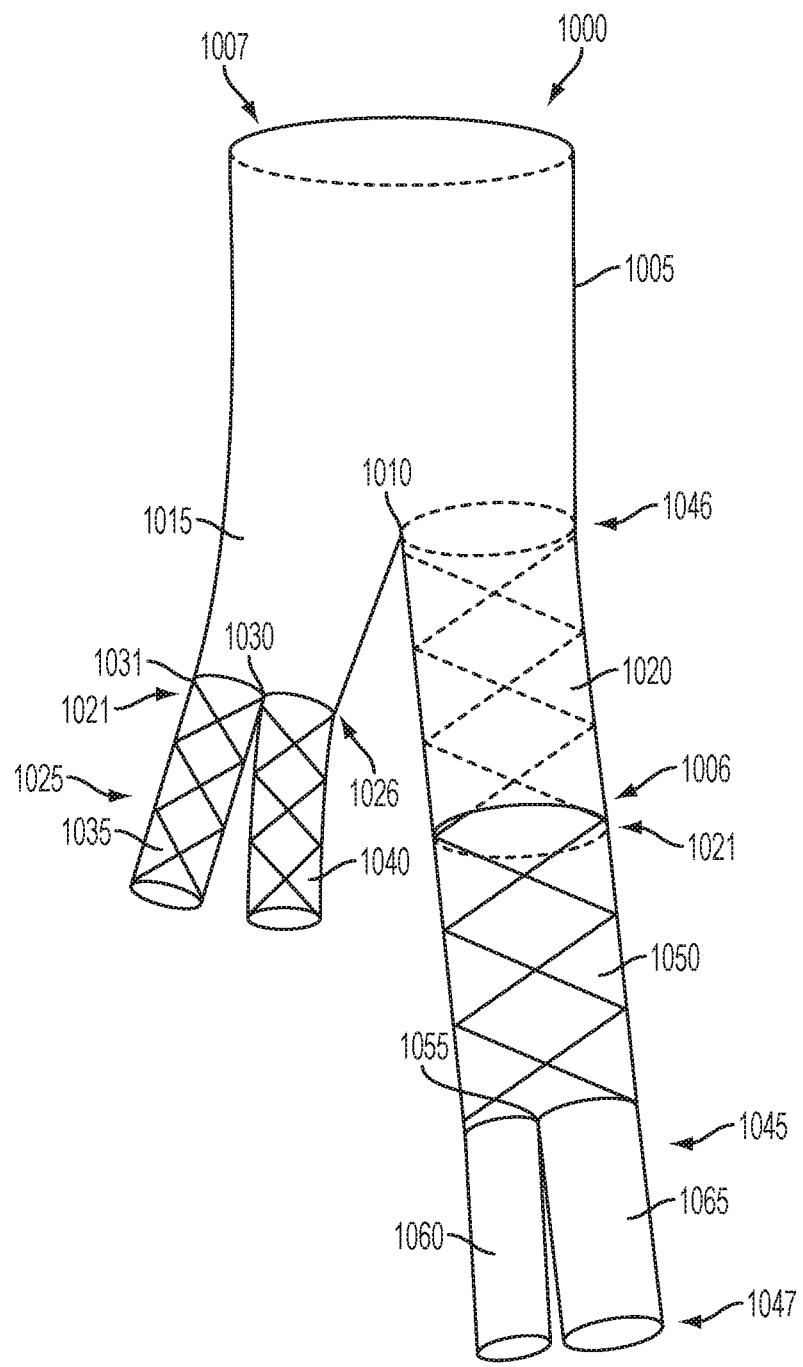
FIG. 10B is an isometric view of one embodiment of a debranching visceral stent graft according to the eleventh aspect of the invention with a visceral limb joined to the first leg in a unitary configuration and a visceral extension deployed within the second leg.

In an eleventh aspect, as shown in FIGS. 10A and 10B, the invention provides a debranching stent graft 1000 comprising, (a) a main body stent graft 1005 with a bifurcation 1010 defining a first leg 1015 and a second leg 1020, wherein the main body stent graft 1050 has a distal end 1006 and a proximal end 1007, (b) wherein the main body stent graft 1005 has a diameter at the proximal end 1007 in the range from about 28 mm to about 36 mm, (c) wherein the first leg 1015 and the second leg 1020 each have a diameter of about 14 mm, (d) wherein the distance from the proximal end 1007 of the main body stent graft 1005 to the distal end 1016 of the first leg 1015 is about 70 mm, (e) and wherein the distance from the proximal end 1007 of the main body stent graft 1005 to the distal end 1021 of the second leg 1020 is about 80 mm. In various embodiments, the diameter at the proximal end 1007 of the main body 1005 may be between about 28-36 mm, 28-34 mm, 28-32 mm, 28-30 mm, 28 mm, 30-36 mm, 32-36 mm, 34-36 mm or about 36 mm.

In one embodiment according to either the tenth or eleventh aspect of the invention, the second leg 720, 820, 920, 1020 defines at least one fenestration.

In another embodiment, as shown in FIGS. 10A and 10B, the eleventh aspect further comprises, a first visceral limb 1025 attached to the first leg 1015 at the distal end 1006 of the main body stent graft 1005, where the first visceral limb 1025 has a bifurcation 1030 defining a third leg 1035 and a fourth leg 1040, where the bifurcation 1030 occurs immediately at the proximal end 1026 of the first visceral limb 1025, where the first visceral limb 1025 has a length of about 30 mm, and where each of the third leg 1035 and the fourth leg 1040 have a diameter of about 7 mm.

In a further embodiment, as shown in FIGS. 10A and 10B, the eleventh aspect further comprises, a visceral extension 1045 joined with the second leg 1020, wherein the visceral extension 1045 has a proximal end 1046 and a distal end 1047, wherein the visceral extension 1045 comprises a tubular main leg 1050 with a bifurcation 1055 defining a first extension leg 1060 and a second extension leg 1065, wherein the first extension leg 1060 has a distal diameter of about 7 mm and the second extension leg 1065 has a distal diameter of about 16 mm, and wherein the visceral extension 1045 has a diameter of about 15 mm at the proximal end 1046 and a diameter of about 20 mm at the bifurcation 1055, wherein the visceral extension 1045 has a length of about 93 mm. In various embodiments, the length of the visceral extension 1045 may be between about 82-199 mm, 87-177 mm, 93-156 mm, 109-140 mm, or about 124 mm, about 82 mm, about 156 mm or about 199 mm.

In a twelfth aspect, as shown in FIG. 3, the invention provides a method for placement of a debranching stent graft 700, 800, 900 according to the tenth or eleventh aspect of the invention, comprising (a) introducing a guidewire into the aorta 300 via arterial access, (b) loading a delivery catheter containing a debranching stent graft 700, 800, 900 according to the tenth or eleventh aspect of the invention onto the guidewire, (c) moving the delivery catheter along the guidewire and introducing the delivery catheter into the aorta via arterial access, (d) and deploying the debranching stent graft 700, 800, 900 into one of the aorta 300 or a lumen of a previously-placed stent graft, such as a stent graft 100, 200 according to the first or second aspects of the invention within the aorta 300.

In one embodiment, as shown in FIG. 3, the twelfth aspect further comprises, (e) introducing a second guidewire into the aorta 300 via arterial access, (f) loading a second delivery catheter containing a visceral limb 725, 825, 925 according to the tenth or eleventh aspect of the invention onto the second guidewire, (g) moving the second delivery catheter along the second guidewire and introducing the second delivery catheter into the first leg 715, 815, 915 or the second leg 720, 820, 920 of the debranching stent graft 700, 800, 900 via arterial access, and (h) deploying a proximal end 726, 826, 926 of the visceral limb stent graft 700, 800, 900 into the first leg 715, 815, 915 or the second leg 720, 820, 920 of the debranching stent graft 700, 800, 900.

In another embodiment, not shown, the twelfth aspect further comprises, (i) introducing a third guidewire into the aorta via arterial access and into a selected lumen of the debranching stent graft 700, 800, 900, (j) loading a third delivery catheter containing a visceral extension stent graft 1045 according to the tenth or eleventh aspect of the invention onto the third guidewire, (k) moving the third delivery catheter along the third guidewire and introducing the third delivery catheter into the selected lumen of the debranching stent graft 700, 800, 900 via arterial access, and (l) deploying a proximal end 1046 of the visceral extension stent graft 1045 into the selected lumen of the debranching stent graft 700, 800, 900, while the distal end extends into a native vessel.

Debranching Great Vessel Stent Graft and Methods for Use

Figure 11A:
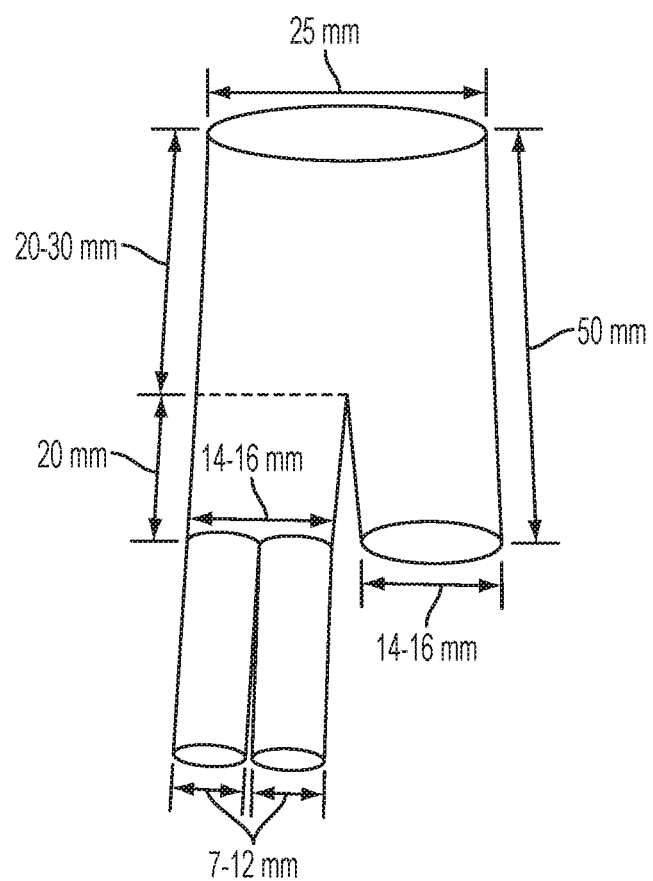
FIG. 11A is an isometric view illustrating the dimensions of one embodiment of a debranching Great vessel stent graft according to the thirteenth aspect of the invention with a Great vessel limb joined to the first leg in a unitary configuration.
Figure 11B:
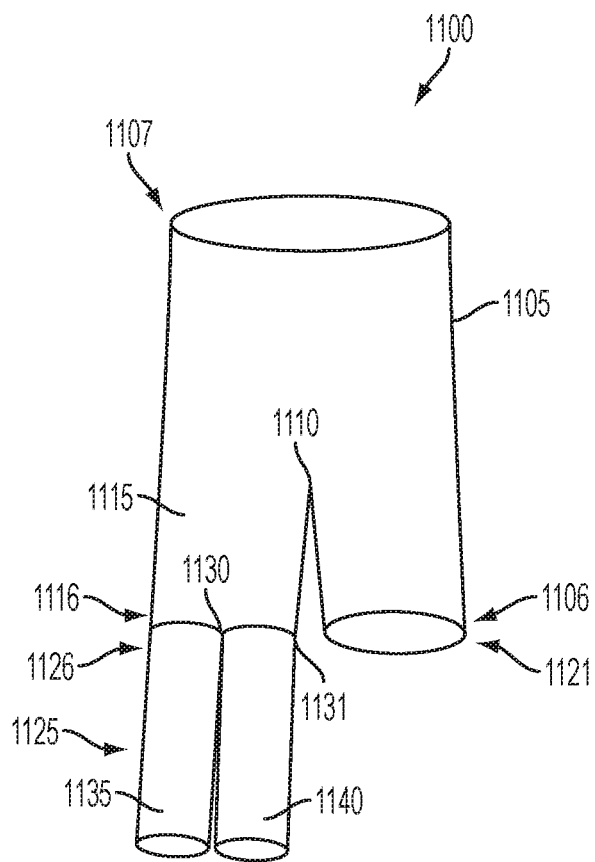
FIG. 11B is an isometric view of one embodiment of a debranching Great vessel stent graft according to the thirteenth aspect of the invention with a Great vessel limb joined to the first leg in a unitary configuration.
Figure 12A:
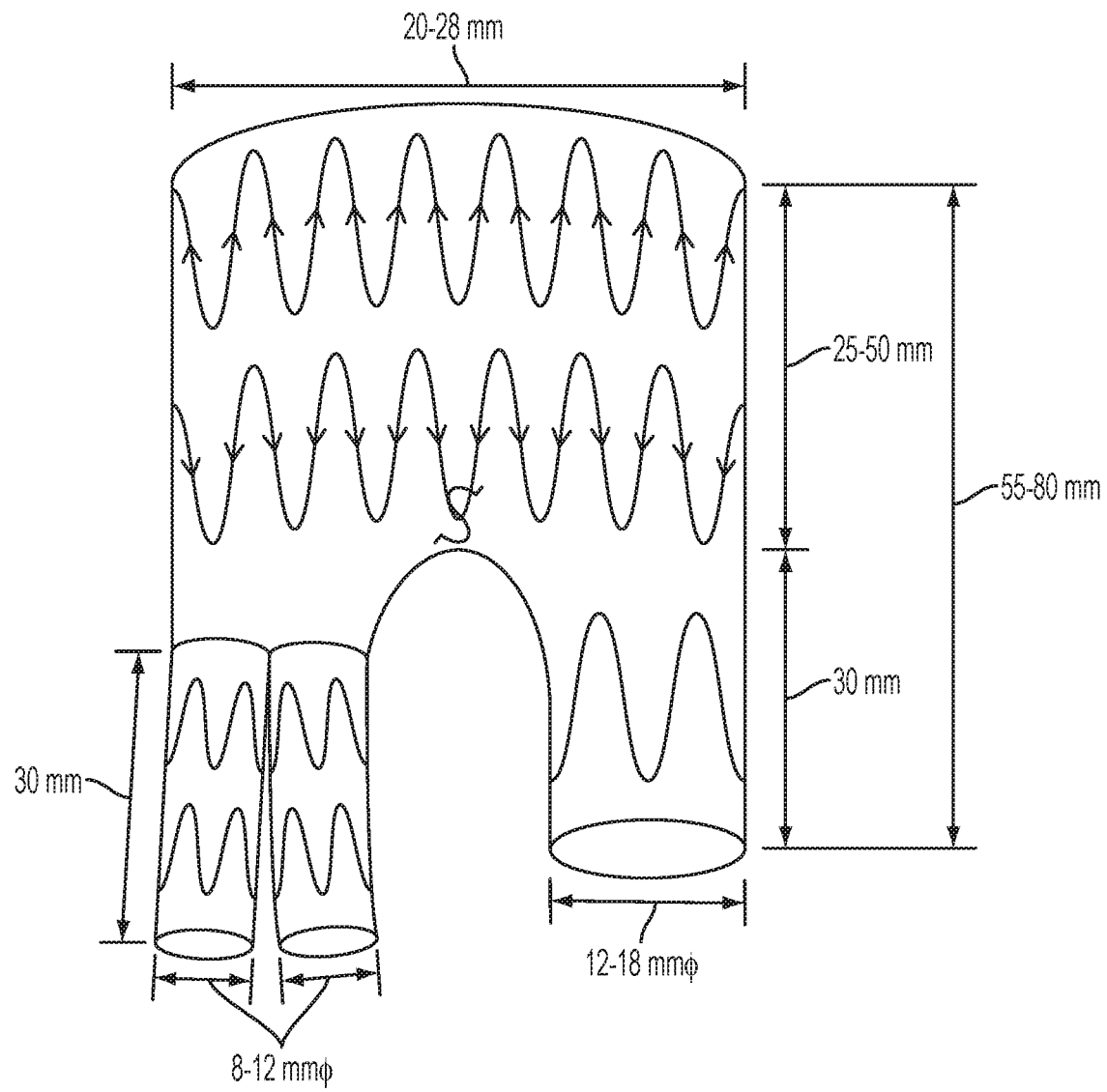
FIG. 12A is an isometric view illustrating the dimensions of one embodiment of a debranching Great vessel stent graft according to the thirteenth aspect of the invention with a Great vessel limb joined to the first leg in a unitary configuration.
Figure 12B:
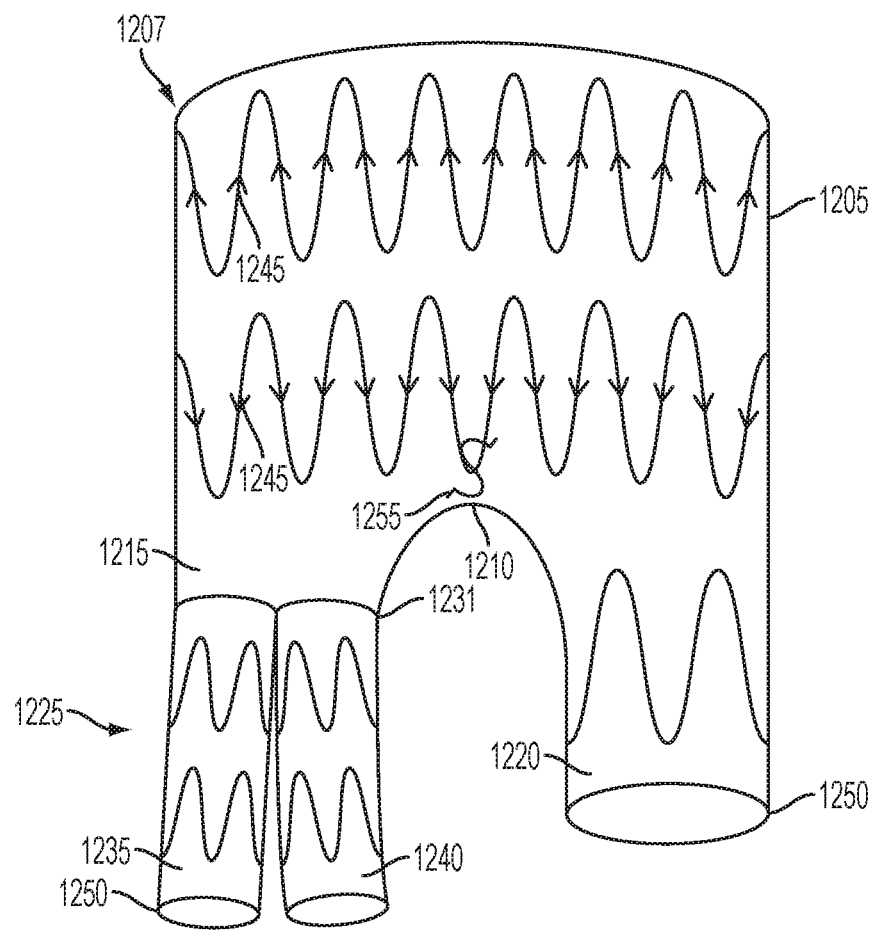
FIG. 12B is an isometric view one embodiment of a debranching Great vessel stent graft according to the thirteenth aspect of the invention with a Great vessel limb joined to the first leg in a unitary configuration.

In a thirteenth aspect, as shown for example in FIGS. 11A-12, the invention provides a debranching stent graft 1100 comprising, (a) a main body stent graft 1105 with a first bifurcation 1110 defining a first leg 1115 and a second leg 1120, wherein the main body stent graft 1105 has a distal end 1106 and a proximal end 1107; wherein the main body stent graft 1105 has a diameter at the proximal end 1106 in the range from about 18 mm to about 28 mm, (b) wherein the first leg 1115 and the second leg 1120 each have a diameter in the range from about 12 mm to about 18 mm, (c) wherein the distance from the proximal end 1106 of the main body stent graft 1105 to the distal end 1116 of the first leg 1115 is in the range from about 30 mm to about 50 mm, and (d) wherein the distance from the proximal end 1107 of the main body stent graft 1105 to the distal end 1121 of the second leg 1120 is in a range from about 50 mm to about 70 mm.

Like the debranching visceral stent graft, the debranching great vessel stent graft may be deployed within a lumen of a double-barreled main body stent graft as a second level in a debranching procedure or placed in direct contact with a vessel wall as an anchoring main body stent graft. In addition, the debranching great vessel stent graft could be deployed in the lumen of any previously-placed appropriately sized stent graft.

In one preferred embodiment, the diameter of the main body stent graft 1105 at the proximal end 1107 is about 25 mm and, in various embodiments, may be between about 18-28 mm, 20-26 mm, 22-25 mm or 24-25 mm. In another preferred embodiment, the first bifurcation 1110 occurs in the range from about 20 mm to about 45 mm from the proximal end 1107 and, in various embodiments, the distance of the first bifurcation 1110 to the proximal end 1107 may be between about 20-50 mm, 25-40 mm, 30-35 mm or about 30 mm. In a further preferred embodiment, the first leg 1115 and the second leg 1120 each have a diameter of about 14 mm and, in various embodiments, may be between about 12-18 mm, 13-17 mm, 14-15 mm or 14-16 mm.

In another embodiment, the thirteenth aspect of the invention further comprises a first great vessel limb 1125 joined with one of the first leg 1115 or the second leg 1120 at the distal end 1106 of the main body stent graft 1105.

In one preferred embodiment shown in FIGS. 11A and 11B, the first great vessel limb 1125 is joined with one of the first leg 1115 or the second leg 1120 via a seam 1131. In this embodiment, the first great vessel limb 1125 preferably has a diameter at the proximal end 1126 in the range from about 14-16 mm and, in various embodiments, the diameter at the proximal end 1126 of the first great vessel limb 1125 may be between about 14-16 mm, 14-15 mm or about 14 mm. Further in this embodiment, the first great vessel limb 1125 preferably has a length about 30 mm. Also in this embodiment, the first great vessel limb 1125 may have a bifurcation 1130 defining a third leg 1135 and a fourth leg 1140, and the bifurcation 1130 preferably occurs approximately at the seam 1131. Here, each of the third leg 1135 and the fourth leg 1140 preferably have a diameter in the range from about 7 mm to about 12 mm.

In a further preferred embodiment, as shown in FIG. 12, the first great vessel limb 1225 is again joined with one of the first leg 1215 or the second leg 1220 via a seam 1231. In this embodiment, the main body stent graft 1205 has a diameter at the proximal end 1207 in the range from about 20 mm to about 28 mm, where the first bifurcation 1210 occurs in the range from about 25 mm to about 45 mm from the proximal end 1207 of the main body stent graft 1205, and where each of the third leg 1235 and the fourth leg 1240 have a diameter in the range from about 8 mm to about 12 mm. In various embodiments, the diameter at the proximal end 1207 of the main body stent graft 1205 may be between about 22-26 mm, 24-26 mm or about 26 mm. In various embodiments, the distance of the first bifurcation 1210 to the proximal end 1207 may be between about 20-45 mm, 25-40 mm, 30-35 mm or about 30 mm. In various embodiments, the diameter of each of the third leg 1235 and the fourth leg 1240 may be between about 8-11 mm, 9-11 mm, 9-12 mm or about 10 mm. In various embodiments, the diameter of the second leg 1220 may be between about 12-18 mm, 14-16 mm or about 14 mm. In various embodiments the length from the proximal end 1207 of the main body stent graft 1205 to the distal end of the second leg 1220 may be between about 55-80 mm, 60-75 mm, 60-70 mm, 60-65 mm, 60-80 mm, 65-80 mm, 70-80 mm, 75-80 mm or about 60 mm or about 80 mm.

In one embodiment, the thirteenth aspect of the invention further comprises a plurality of bi-directional anchor hooks 1245 attached to two adjacent stents at the proximal end of the main body stent graft 1205.

In still another embodiment, the thirteenth aspect of the invention further comprises a radiopaque band 1250 disposed at the distal end of each of the first leg 1215, third leg 1235 and fourth leg 1240.

In another embodiment, the main body stent graft 1205 may further include a directional marker 1255 on the main body stent graft 1205 in any configuration, for example, an "S" shape.

Figure 13A:
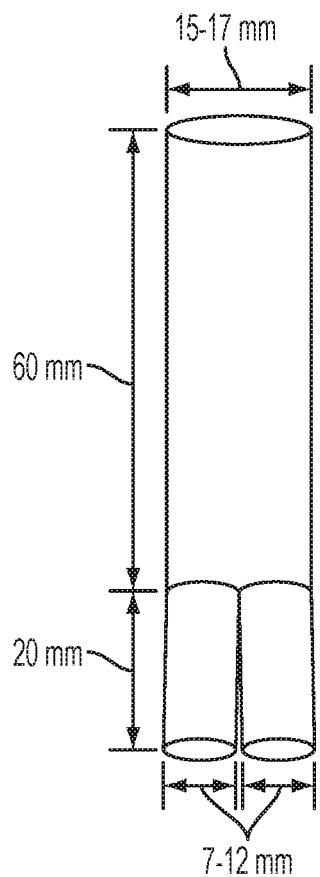
FIG. 13A is an isometric view illustrating the dimensions of one embodiment of a Great vessel limb according to the thirteenth aspect of the invention with a Great vessel limb for deployment and passive fixation in a debranching Great vessel stent graft.
Figure 13B:
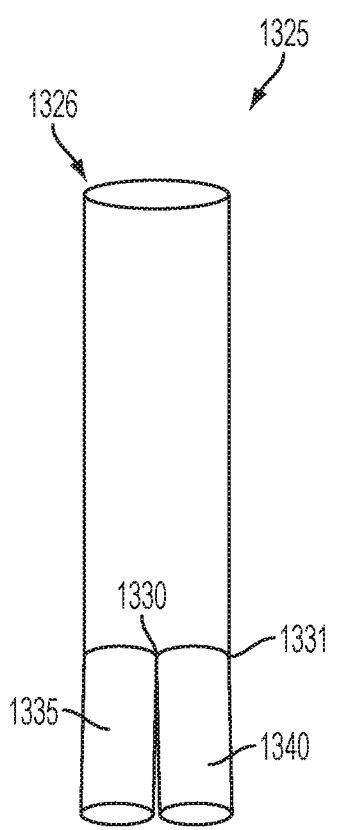
FIG. 13B is an isometric view of one embodiment of a Great vessel limb according to the thirteenth aspect of the invention with a Great vessel limb for deployment and passive fixation in a debranching Great vessel stent graft.

In another preferred embodiment, as shown in FIGS. 13A and 13B, the first great vessel limb 1325 is joined with one of the first leg 1115 or the second leg 1120 via passive fixation. In this embodiment, the first great vessel limb 1325 preferably has a diameter at the proximal end 1326 in a range from about 15 mm to about 17 mm and, in various embodiments, may be between about 15-16 mm, 16-17 mm or about 16 mm. The diameter at the proximal end 1326 of the great vessel limb 1325 should be at least 1 mm larger than the diameter of the leg that receives the limb and the overlap between the leg and limb should be at least 30 mm in order for passive fixation to be effective. Further in this embodiment, the first great vessel limb 1325 preferably has a length in the range from about 60 mm to about 100 mm and, in various embodiments, may be between about 60-75 mm, 60-70 mm, 60-65 mm or about 60 mm. In one passive fixation embodiment, the first great vessel limb 1335 has a bifurcation 1330 defining a third leg 1335 and a fourth leg 1340, and the third leg 1335 and the fourth leg 1340 each preferably have a length of about 30 mm. In this passive fixation embodiment, each of the third leg 1335 and the fourth leg 1340 preferably have a diameter in the range from about 7 mm to about 12 mm. In various embodiments, the length of the third leg 1335 may be between about 8-11 mm, 9-11 mm, 9-10 mm or about 10 mm. In various embodiments, the length of the fourth leg 1340 may be between about 7-11 mm, 7-10 mm, 7-9 mm, 7-8 mm or about 7 mm.

In still another embodiment, the thirteenth aspect of the invention further comprises a second great vessel limb attached to the other of the first leg 1115 or the second leg 1120. The second great vessel limb can take the form of any embodiment of the first great vessel limb 1325. In a further embodiment, the second great vessel limb comprises an extension stent graft.

In one embodiment, the second leg 1120 defines at least one fenestration.

In a fourteenth aspect, the invention provides a method for placement of a debranching stent graft 1100, 1200 according to the thirteenth aspect of the invention, comprising (a) introducing a guidewire into an aorta via arterial access, (b) loading a delivery catheter containing a debranching stent graft 1100 according to the thirteenth aspect of the invention onto the guidewire, (c) moving the delivery catheter along the guidewire and introducing the delivery catheter into the aorta via arterial access, and (d) deploying the debranching stent graft 1100 into one of the aorta or a lumen of a previously-placed stent graft, such as a stent graft 400 according to the sixth aspect of the invention within the aorta.

In one embodiment, the fourteenth aspect further comprises, (e) introducing a second guidewire into the aorta via arterial access, (f) loading a second delivery catheter containing a great vessel limb 1325 according to the thirteenth aspect of the invention onto the second guidewire, (g) moving the second delivery catheter along the second guidewire and introducing the second delivery catheter into a selected leg of the debranching stent graft 1100 via arterial access, and (h) deploying a proximal end 1326 of the great vessel limb 1325 into the selected leg of the debranching stent graft 1100, 1200.

In one embodiment, the fourteenth aspect still further comprises, (i) introducing a third guidewire into the descending aorta via arterial access and into a selected lumen of the debranching stent graft according to the thirteenth aspect of the invention, (j) loading a third delivery catheter containing an extension stent graft onto the third guidewire, (k) moving the third delivery catheter along the third guidewire and introducing the third delivery catheter into the selected lumen of the debranching stent graft 1100, 1200 via arterial access, and (l) deploying a proximal end of the extension stent graft into the selected lumen of the debranching stent graft 1100, 1200, while the distal end of the extension stent graft extends into a vessel.

In a fifteenth aspect, the invention provides a method for placement of a debranching stent graft 1100, 1200 according to the thirteenth aspect of the invention, comprising (a) introducing a guidewire into an aortic arch via arterial access, (b) loading a delivery catheter containing a debranching stent graft 1100, 1200 according to the thirteenth aspect of the invention onto the guidewire, (c) moving the delivery catheter along the guidewire and introducing the delivery catheter into the aortic arch via arterial access, and (d) deploying the debranching stent graft 1100, 1200 into one of the proximal descending aorta or a lumen of a previously-placed stent graft, such as a stent graft 400 according to the sixth aspect of the invention within the proximal descending aorta.

In a sixteenth aspect, as shown in FIG. 6, the invention provides a method for placement of a debranching stent graft 1100, 1200 according to the thirteenth aspect of the invention, comprising (a) introducing a guidewire into an ascending aorta via arterial access, (b) loading a delivery catheter containing a debranching stent graft 1100, 1200 according to the thirteenth aspect of the invention onto the guidewire, (c) moving the delivery catheter along the guidewire and introducing the delivery catheter into the ascending aorta via arterial access, and (d) deploying the debranching stent graft 1100, 1200 into one of the ascending aorta or a lumen of a previously-placed stent graft, such as a stent graft, 400 according to the sixth aspect of the invention within the ascending aorta.

In one embodiment, the sixteenth aspect further comprises, (e) introducing a second guidewire into the ascending aorta via arterial access and into a selected leg of the debranching stent graft 1100, 1200, (f) loading a second delivery catheter containing a great vessel limb 1325 according to the thirteenth aspect of the invention onto the second guidewire, (g) moving the second delivery catheter along the second guidewire and introducing the second delivery catheter into the selected leg of the debranching stent graft via arterial access, and (h) deploying a proximal end 1326 of the great vessel limb 1325 into the selected leg of the debranching stent graft 1100, 1200.

In one embodiment, the sixteenth aspect still further comprises, (i) introducing a third guidewire into the ascending aorta via arterial access and into a selected leg of the debranching stent graft 1100, 1200 according to the thirteenth aspect of the invention, (j) loading a third delivery catheter containing an extension stent graft according to the thirteenth aspect of the invention onto the third guidewire, (k) moving the third delivery catheter along the third guidewire and introducing the third delivery catheter into the selected leg of the debranching stent graft via arterial access, and (l) deploying a proximal end of the extension stent graft into the selected leg of the debranching stent graft 1100, 1200, while the distal end of the extension stent graft extends into a great vessel.

Debranching Stent Graft Limb and Methods for Use

The debranching stent graft limbs can be used to exclude a diseased artery/arteries involving a branched arterial configuration, including any aneurysm of any anatomical variation or other type of diseased artery or traumatic injury. The debranching stent graft limbs of the invention are able to connect to almost any anatomy, and thus provide an ease of use in a variety of patients. Deliverance of these debranching stent graft limbs may be in either an antegrade or retrograde manner, thus allowing approach to almost any diseased artery. When this debranching stent graft limb is used in combination with an existing aortic stent graft platform, one non-limiting embodiment may be treatment of common iliac aneurysms in which the stent graft may be oriented within the common iliac artery and the first and second expandable prostheses extended into the external and internal iliac arteries, respectively, to maintain pelvic blood flow.

Figure 14A:
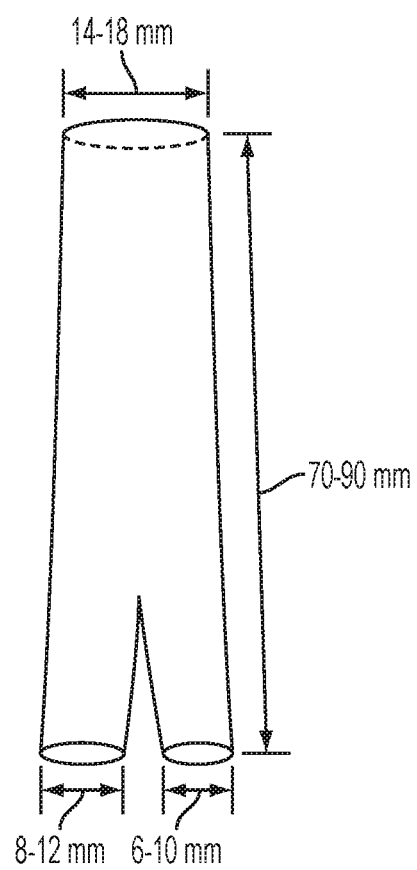
FIG. 14A is an isometric view illustrating the dimensions of one embodiment of a debranching stent graft limb according to the seventeenth aspect of the invention.
Figure 14B:
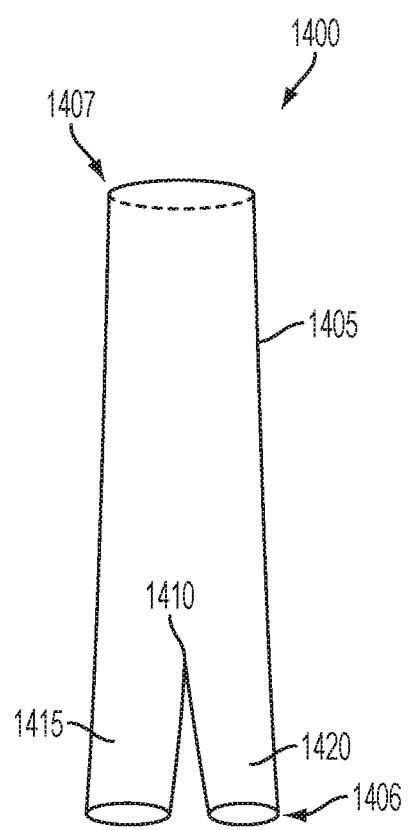
FIG. 14B is an isometric view of one embodiment of a debranching stent graft limb according to the seventeenth aspect of the invention.

In a seventeenth aspect, as shown in FIGS. 14A and 14B, the invention provides a debranching stent graft limb 1400 comprising, (a) a main body stent graft limb 1405 with a bifurcation 1410 defining a first leg 1415 and a second leg 1420, wherein the main body stent graft limb 1405 has a distal end 1406 and a proximal end 1407, (b) wherein the main body stent graft limb 1405 has a diameter at the proximal end in the range from about 14 mm to about 18 mm, (c) wherein the first leg 1415 has a diameter ranging from about 8 mm to about 12 mm, (d) wherein the second leg 1420 has a diameter ranging from about 6 mm to about 10 mm, and (e) wherein the distance from the proximal end 1407 of the main body stent graft 1405 to the distal end 1416 of the first leg 1415 and the second leg 1421 is in the range from about 70 mm to about 90 mm, and wherein the diameter of the first leg 1415 is about 2 mm greater than the diameter of the second leg 1420.

In one preferred embodiment, the diameter of the first leg 1415 is about 10 mm and the diameter of the second leg 1420 is about 8 mm. In various embodiments, the diameter of the first leg 1415 may be between about 8-12 mm, 8-11 mm, 8-10 mm, 9-10 mm, 9-11 mm or 9-12 mm. In various embodiments, the diameter of the second leg 1420 may be between about 6-10 mm, 7-9 mm, 7-8 mm or about 7 mm.

In another preferred embodiment, the diameter of the main body stent graft limb 1405 at the proximal end 1407 is about 16 mm and, in various embodiments, may be between 14-18 mm, 15-17 mm or about 16 mm.

In a further preferred embodiment, the distance from the proximal end 1407 of the main body stent graft 1405 to the distal end 1416 of the first leg 1415 and the second leg 1421 is 80 mm and, in various embodiments, may be between about 70-90 mm, 70-85 mm, 75-85 mm, or 75-90 mm.

In a further preferred embodiment, the distance from the proximal end 1407 of the main body stent graft 1405 to the bifurcation 1410 is about 40 mm to 60 mm.

In yet another embodiment, the seventeenth aspect further comprises a first limb expanded within the first leg 1415 and coupled to the first leg 1415 via passive fixation and a second limb expanded within the second leg 1420 and coupled to the second leg 1420 via passive fixation.

Figure 15A:
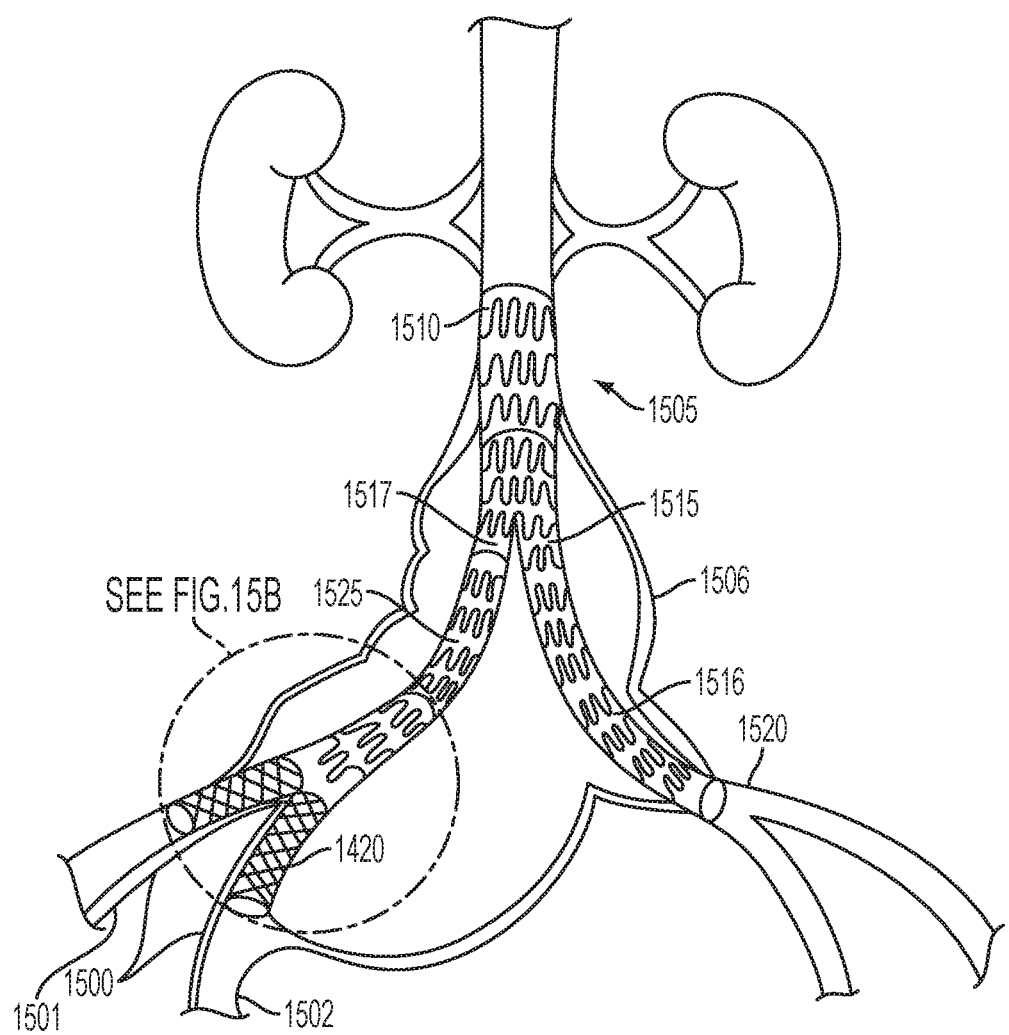
FIG. 15A is a cross-sectional view of the abdominal aorta with an isometric view of one embodiment of a debranching stent graft limb according to the seventeenth aspect of the invention after deployment during a debranching procedure.
Figure 15B:
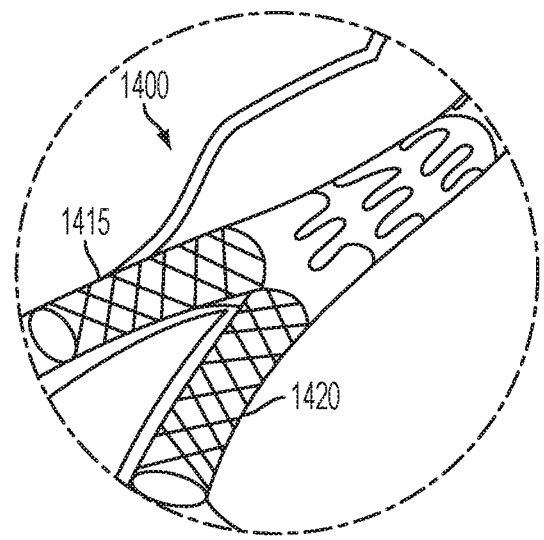
FIG. 15B is a detail view of a cross-section of the aneurysmal sac with an isometric view of one embodiment of a debranching stent graft limb according to the seventeenth aspect of the invention after deployment during a debranching procedure.

In an eighteenth aspect, as shown in FIG. 15, the invention provides a method for placement of a debranching stent graft limb 1400 according to the seventeenth aspect of the invention, comprising, (a) introducing a guidewire into any appropriately sized branched arterial configuration 1500 via arterial access, (b) loading a delivery catheter containing a debranching stent graft limb 1400 according to the seventeenth aspect of the invention onto the guidewire, (c) moving the delivery catheter along the guidewire and introducing the delivery catheter into the appropriately sized branched arterial configuration 1500 via arterial access, and (d) deploying the debranching stent graft limb 1400 into one of the appropriately sized branched arterial configuration 1500 and/or a lumen of a previously-placed stent graft, such as a stent graft according to the tenth, eleventh or thirteenth aspect of the invention.

In one example shown in FIG. 15, a main body stent graft 1510 is anchored in non-diseased tissue of the aorta 1505. A bifurcated stent graft 1515 is then deployed within the lumen of the main body stent graft 1510, with one lumen 1516 extending into left common iliac artery 1520 and the other lumen 1517 extending within the aneurysmal sac 1506. An extension stent graft 1525 is shown deployed within the lumen 1517 within the aneurysmal sac 1506. The debranching stent graft limb 1400 is shown deployed within the extension stent graft 1525 to bridge the aneurysmal sac 1506 and stent the right external iliac artery 1501. In practice, an additional extension stent graft (not shown) would typically then be deployed into the right internal iliac artery 1502, as described below.

In one embodiment, as shown in FIG. 15, the eighteenth aspect of the invention further comprises (e) loading a second delivery catheter containing a first limb according to the seventeenth aspect of the invention onto a proximal end of the guidewire, (f) moving the second delivery catheter along the guidewire and introducing the second delivery catheter into the first leg 1415 of the debranching stent graft limb 1400 via arterial access, and (g) deploying a proximal end of the first limb into the first leg 1415 of the debranching stent graft limb 1400.

In another embodiment, as shown in FIG. 15, the eighteenth aspect of the invention still further comprises (h) introducing a second guidewire into the appropriately sized branched arterial configuration through the second leg 1420 of a debranching stent limb 1400 according to the seventeenth aspect of the invention via arterial access, (i) loading a third delivery catheter containing a second limb according to the seventeenth aspect of the invention onto the second guidewire, (j) moving the third delivery catheter along the second guidewire and introducing the third delivery catheter into the second leg 1420 of the debranching stent graft limb 1400 via arterial access, and (k) deploying a proximal end of the second limb into the second leg 1420 of the debranching stent graft limb 1400 in the appropriately sized branched arterial configuration.

In one embodiment, the appropriately sized branched arterial configuration comprises the common iliac artery.

In a further embodiment, the invention further comprises placing an axillary conduit in the exposed artery in the arm. The axillary conduit serves to stabilize the exposed access point of the artery for guidewire and catheter entry. The axillary conduit may be utilized with any exposed artery access point in any of the methods described herein.

In a nineteenth aspect, the invention provides a method for placement of a debranching stent graft limb 1400 according to the seventeenth aspect of the invention, comprising, (a) introducing a guidewire into a common iliac artery via arterial access, (b) loading a delivery catheter containing a debranching stent graft limb 1400 according to the seventeenth aspect of the invention onto the guidewire, (c) moving the delivery catheter along the guidewire and introducing the delivery catheter into the common iliac artery via arterial access, and (d) deploying the debranching stent graft limb 1400 into one of the common iliac artery and/or a lumen of a previously-placed stent graft, such as a stent graft according to the tenth, eleventh or thirteenth aspect of the invention.

Combination Double-Barreled and Debranching Stent Grafts and Methods for Use

The combination double-barreled and debranching Great vessel main body stent grafts can be used to treat any aneurysm of any anatomical variation or other type of diseased artery or traumatic injury. This combination stent graft may be used in an antegrade deployment in the ascending aorta in the normal direction of blood flow. In the antegrade deployment, the proximal portion of the stent graft can be deployed within one centimeter of the aortic valve coronary arteries. In this arrangement, one of the first or second lumens of the combination stent graft is dedicated to the innominate artery, while the other lumen is dedicated to the left common carotid and the left subclavian arteries. Alternatively, the stent graft may be used in a retrograde deployment in the aortic arch against the normal direction of blood flow. In the retrograde deployment, the proximal portion of the combination stent graft can be placed about 11 cm distal to the left subclavian artery. In this arrangement, one of the first or second lumens is dedicated to the Great vessels, while the other lumen is dedicated to the ascending aorta.

Figure 16A:
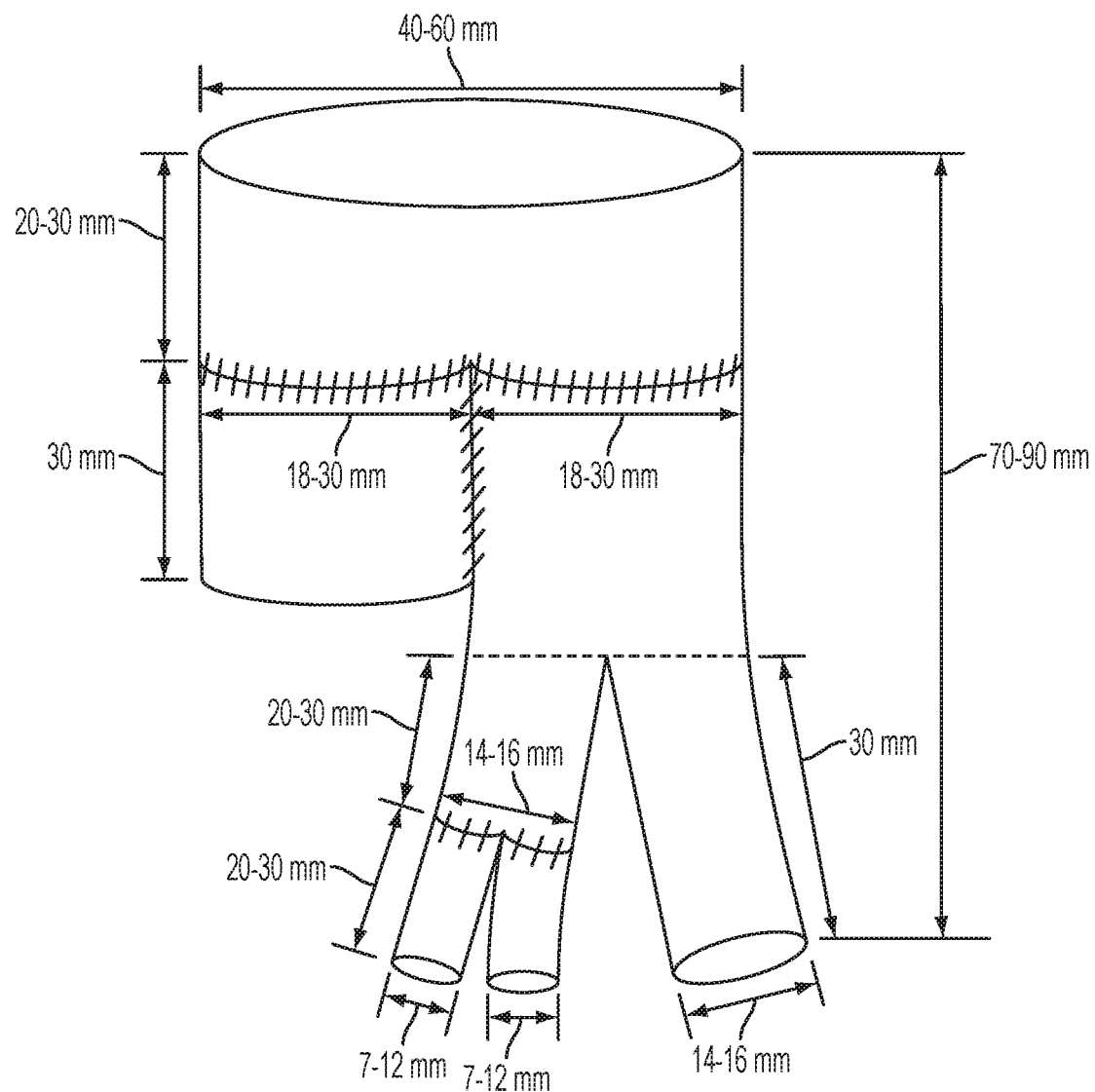
FIG. 16A is an isometric view illustrating the dimensions of one embodiment of a double-barreled and main body stent graft according to the twentieth aspect of the invention.
Figure 16B:
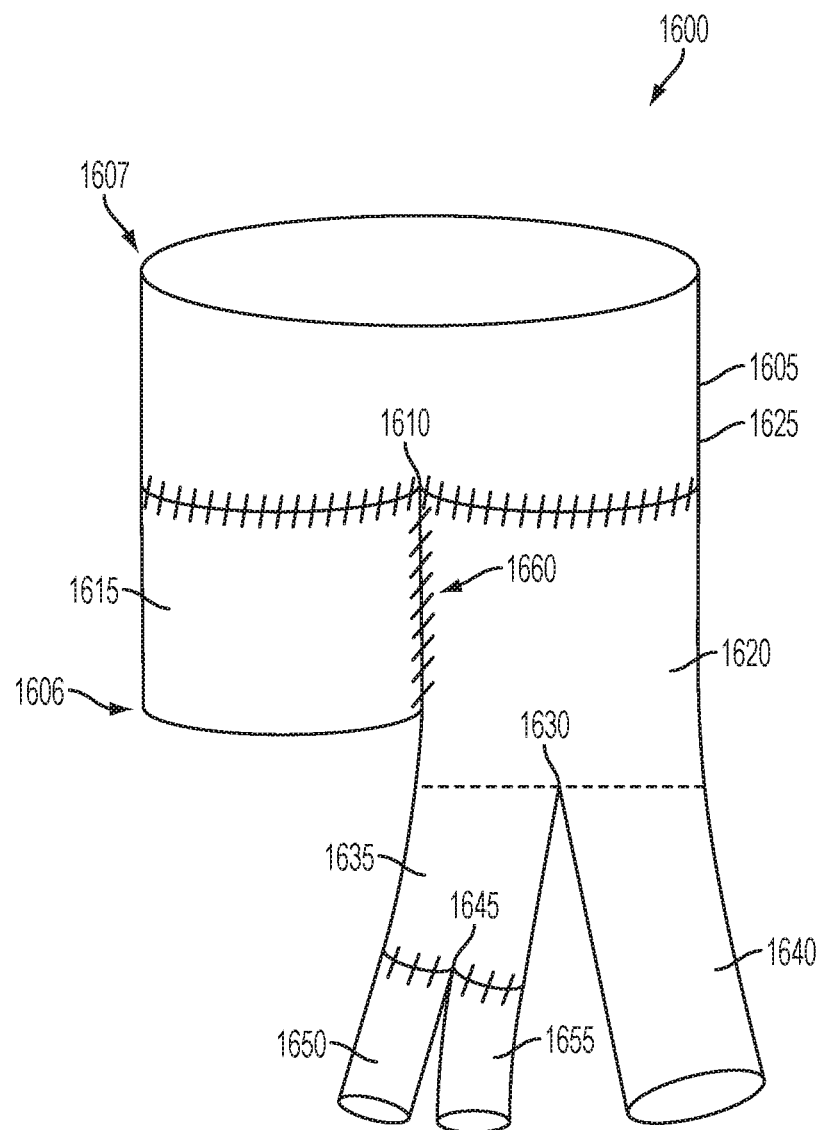
FIG. 16B is an isometric view of one embodiment of a double-barreled and main body stent graft according to the twentieth aspect of the invention.

In a twentieth aspect, as shown in FIGS. 16A and 16B, the invention provides a stent graft 1600 comprising, (a) a main body stent graft 1605 defining a single lumen and having a distal end 1606 and a proximal end 1607, (b) a first bifurcation 1610 in the range from about 20 mm to about 30 mm from the proximal end 1607 of the main body stent graft 1605 defining a first lumen 1615 and a second lumen 1620, wherein the main body stent graft 1605 defines a tubular wall 1625 that is contiguous with the first lumen 1615 and the second lumen 1620 such that any fluid entering the main body stent graft 1605 must exit by entering one of the first lumen 1615 or the second lumen 1620, wherein the main body stent graft 1605 has a diameter at the proximal end 1607 in the range from about 40 mm to about 60 mm, wherein the first lumen 1615 and the second lumen 1620 each have a diameter in the range from about 18 mm to about 30 mm, wherein the length from the proximal end 1607 of the main body stent graft 1605 to the distal end 1621 of the second lumen 1620 is in the range from about 70 mm to about 90 mm, (c) a second bifurcation 1630 within the second lumen 1620 about 30 mm from the distal end 1621 of the second lumen 1620 defining a first leg 1635 and a second leg 1640, wherein the first leg 1635 and the second leg 1640 each have a diameter in the range from about 14 mm to about 16 mm, and (d) a third bifurcation 1645 within the second leg 1640 about 20 mm to 30 mm distal from the second bifurcation 1630 defining a third leg 1650 and a fourth leg 1655, wherein the third leg and the fourth leg each have a diameter in the range from about 7 mm to about 12 mm, wherein the third leg 1650 and fourth leg 1655 each have a length in the range from about 20 mm to about 30 mm.

In one embodiment of the twentieth and the twenty-first aspects, the combination double-barreled and debranching main body stent graft 1600, 1700 can be made by joining a debranching stent graft to the complete periphery of a distal end of an existing single lumen main body stent graft and then optionally join the first lumen 1615 and the second lumen 1620 to one another along a shared length. The main body stent graft can be joined with a debranching stent graft using adhesive, sewing, bonding, or welding, or any other known mechanism, for example. The same means can be used to join the two single lumens along a shared length 1660. Alternatively, the main body stent graft and the debranching stent graft could be manufactured as a single unitary stent graft. These mechanisms for joining, securing or attaching stent graft components together prior to in vivo deployment can be used with any of the aspects for the double-barreled stent grafts, debranching stent grafts or debranching stent graft limbs disclosed herein.

In one preferred embodiment, the main body stent graft 1605 has a diameter at the proximal end 1606 of about 40 mm and, in various embodiments, may be between about 40-60 mm, 45-55 mm, about 50 mm, about 60 mm or about 40 mm. In another preferred embodiment, the first lumen 1615 has a diameter of about 20 mm and, in various embodiments, may be between about 18-30 mm, 20-28 mm, 22-26 mm or 24 mm. In a further preferred embodiment, the second lumen 1620 has a diameter in the range from about 18 mm to about 20 mm and, in various embodiments, may be between about 18-30 mm, 20-28 mm, 22-26 mm or about 24 mm. In yet another preferred embodiment, the length from the proximal end 1607 of the main body stent graft 1605 to the distal end 1621 of the second lumen 1620 is about 70 mm and, in various embodiments, may be between about 70-90 mm, 70-85 mm, 70-80 mm, 70-75 mm, 70 mm, 75-90 mm, 80-90 mm, 85-90 mm or about 90 mm. In various embodiments, each of the diameters of the first leg 1635 and the second leg 1640 may be between about 14-16 mm, 14-15 mm, 15-16 mm or about 14 mm. In various embodiments, the third leg 1650 and the fourth leg 1655 each have a diameter in the range from about 7 mm to about 12 mm and, in various embodiments, may be between about 7-12 mm, 8-11 mm, 9-10 mm or about 10 mm. In a preferred embodiment, the third leg 1650 and fourth leg 1655 each have a length of about 30 mm.

In another preferred embodiment of the twentieth and the twenty-first aspects, the first lumen and the second lumen each retain a substantially cylindrical profile. In one embodiment, a cylindrical stent structure is disposed on an exterior of the main body stent graft to aid the first and second lumens in maintaining a substantially cylindrical profile.

In one embodiment, the first lumen 1615 is secured to the second lumen 1620 along a shared length of about 30 mm. In another embodiment of the twentieth and the twenty-first aspects, the first lumen 1615 and the second lumen 1620 are secured together along the shared length 1660 via one or more of stitching, adhesive, or bonding. The two lumens are secured together in a manner that does not substantially deform the cylindrical shape of the lumens. This embodiment is equally applicable to any aspects of the double-barreled stent grafts and debranching stent grafts, especially when a given stent graft is intended for use as an anchoring main body stent graft.

Figure 17A:
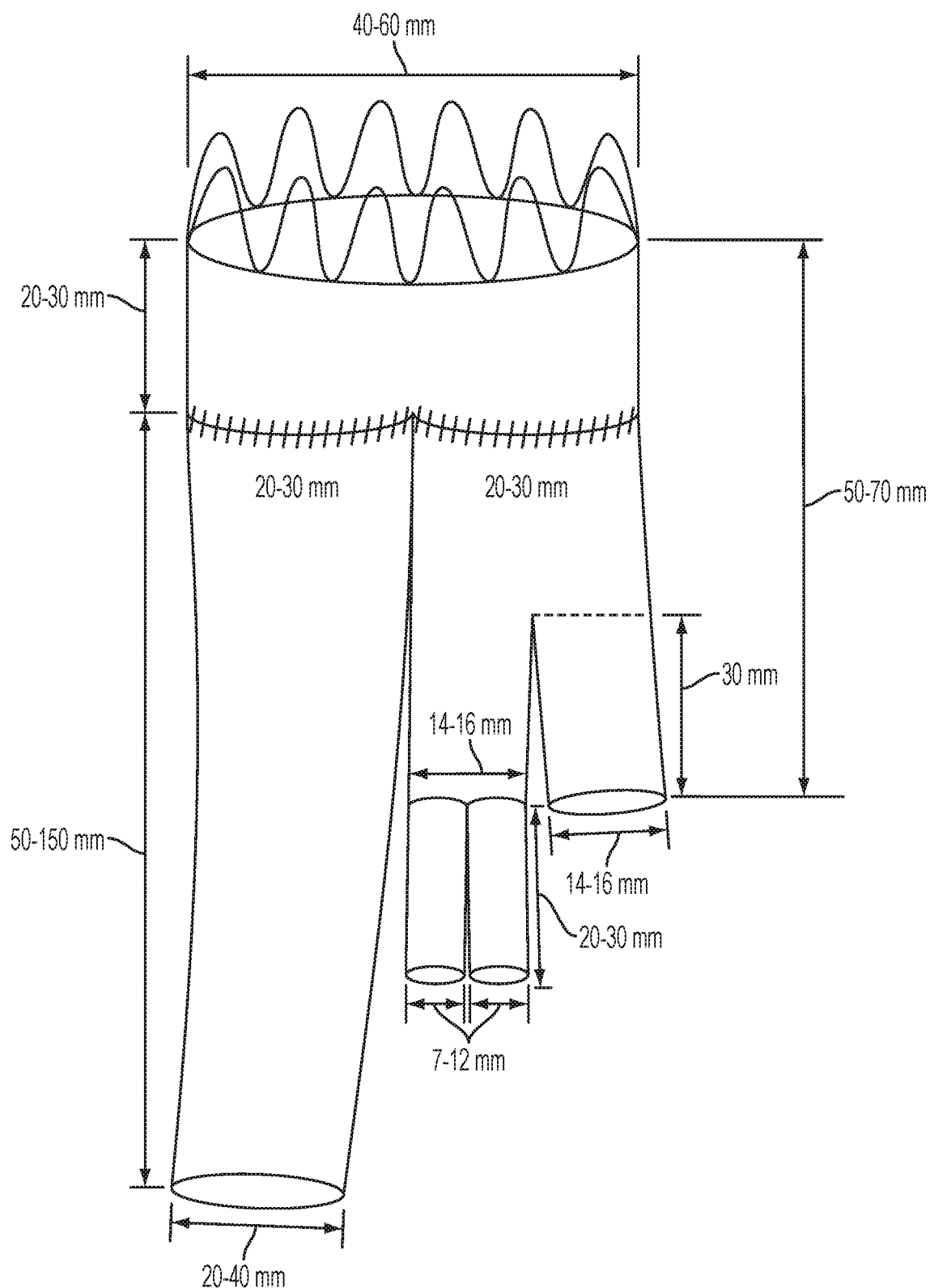
FIG. 17A is an isometric view illustrating the dimensions of one embodiment of a double-barreled and main body stent graft according to the twenty-first aspect of the invention.
Figure 17B:
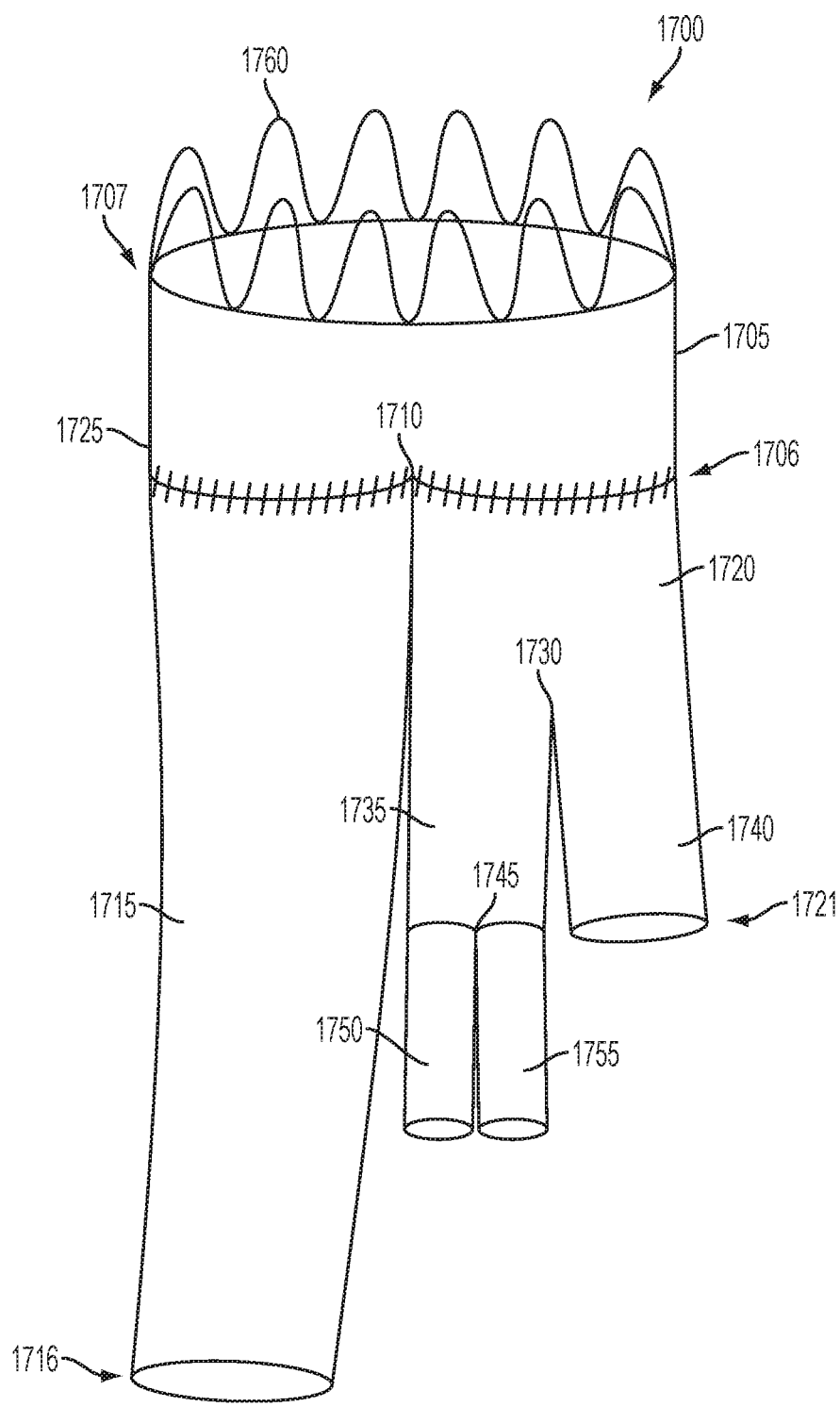
FIG. 17B is an isometric view of one embodiment of a double-barreled and main body stent graft according to the twenty-first aspect of the invention.

In another embodiment, as shown in FIGS. 17A and 17B, the twentieth and the twenty-first aspect further comprise a fixation stent 1765 affixed to the proximal end 1707 of the main body stent graft 1705. This embodiment is equally applicable to any aspects of the double-barreled stent grafts and debranching stent grafts, especially when a given stent graft is intended for use as an anchoring main body stent graft.

In a twenty-first aspect, as shown in FIGS. 17A and 17B, the invention provides a stent graft 1700 comprising, (a) a main body stent graft 1705 defining a single lumen and having a distal end 1706 and a proximal end 1707, (b) a first bifurcation 1710 in the range from about 20 mm to about 30 mm from the proximal end 1707 of the main body stent graft 1705 defining a first lumen 1715 and a second lumen 1720, wherein the main body stent graft 1705 has a diameter at the proximal end 1707 in the range from about 40 mm to about 60 mm, wherein the first lumen 1715 has a diameter in the range from about 20 mm to about 30 mm at the first bifurcation 1710 and has a diameter in the range from about 20 mm to 40 mm at the distal end 1716 of the first lumen 1715, wherein the first lumen 1715 has a length from about 50 mm to about 150 mm from the first bifurcation 1710 to the distal end 1716 of the first lumen 1715, wherein the second lumen 1720 has a diameter in the range from about 20 mm to about 30 mm at the first bifurcation 1710, (c) a second bifurcation 1730 within the second lumen 1720 about 30 mm from the distal end 1721 of the second lumen 1720 defining a first leg 1735 and a second leg 1740, wherein the first leg 1735 and the second leg 1740 each have a diameter in the range from about 14 mm to about 16 mm, wherein the length from the proximal end 1707 of the main body stent graft 1705 to the distal end 1741 of the second lumen's second leg 1740 is in the range from about 50 mm to about 70 mm, and (d) a third bifurcation 1745 within the first leg 1735 that defines a third leg 1750 and a fourth leg 1755, wherein the third leg 1750 and the fourth leg 1755 each have a diameter of about 7 mm to about 12 mm, wherein the third leg 1750 and fourth leg 1755 each have a length in the range from about 20 mm to about 30 mm.

In various embodiments, the diameter at the proximal end 1706 of the main body stent graft 1705 may be between about 40-60 mm, 40-55 mm, 40-50 mm, 40-45 mm, 45-55 mm, 45-60 mm, 50-60 mm, 55-60 mm, about 50 mm, about 60 mm or about 40 mm. In various embodiments, the first lumen 1715 has a diameter in the range from about 20 mm to 40 mm at the distal end 1716 of the first lumen 1715 and, in various embodiments, may be between about 21-45 mm, 22-40 mm, 23-35 mm, 24-30 mm or about 24 mm. In various embodiments, the length from the proximal end 1707 of the main body stent graft 1705 to the distal end 1721 of the second lumen 1720 may be between about 50-70 mm, 50-65 mm, 50-60 mm, 50-55 mm, 50 mm, 55-70 mm, 60-70 mm, 55-70 mm or about 70 mm. In various embodiments, each of the diameters of the first leg 1735 and the second leg 1740 may be between about 14-16 mm, 14-15 mm, 15-16 mm or about 14 mm. In various embodiments, the third leg 1750 and the fourth leg 1755 each have a diameter in the range from about 7 mm to about 12 mm and, in various embodiments, may be between about 8-11 mm, 9-10 mm or about 10 mm. In a preferred embodiment, the third leg 1650 and fourth leg 1655 each have a length of about 30 mm.

In one preferred embodiment, the main body stent graft 1705 defines a tubular wall 1725 that is contiguous with the first lumen 1715 and the second lumen 1720 such that any fluid entering the main body stent graft 1705 must exit by entering one of the first lumen 1715 or the second lumen 1720. This tubular wall 1725 forms a complete seal with the aortic wall.

In one embodiment, the first lumen 1715 is secured to the second lumen 1720 along a shared length 1760 from the first bifurcation 1710 to the third bifurcation 1745.

Figure 18:
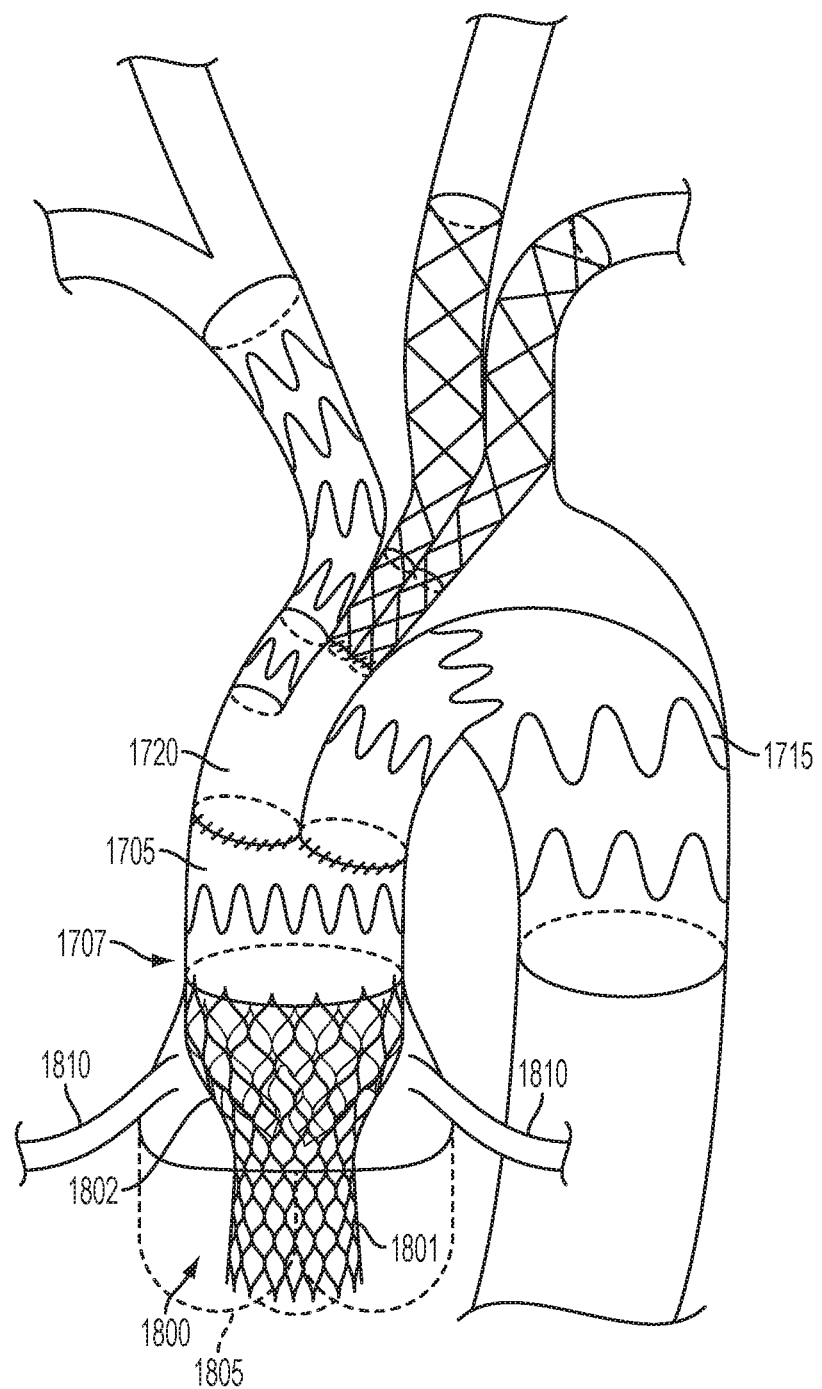
FIG. 18 is a cross-sectional view of the ascending aorta and the proximal descending aorta with an isometric view of one embodiment of double-barreled and main body stent graft including a stent valve according to the twenty-first aspect of the invention and multiple stent graft extenders after deployment during a debranching procedure.

In one embodiment, shown in FIG. 18, the twentieth and/or the twenty-first aspects further comprise a stent valve 1800 affixed to the proximal end 1707 of the main body stent graft 1705, where a free end 1801 of the stent valve 1800 is covered and a portion of the stent valve 1802 extending between the free end 1801 and the proximal end 1707 of the main body stent graft 1705 is uncovered. In this embodiment, the free covered end 1801 of the stent valve 1800 lies in the aortic outflow tract 1805, while the uncovered portion 1802 of the stent valve 1800 lays across the coronary arteries 1810 permitting blood flow to continue in a normal manner.

In a twenty-second aspect, the invention provides a method for placement of a stent graft 1600, 1700 according to one of the twentieth or twenty-first aspects of the invention, comprising, (a) introducing a guidewire into a thoracic aorta via arterial access, (b) loading a delivery catheter containing a stent graft 1600, 1700 according to one of the twentieth or twenty-first aspects of the invention onto the guidewire, (c) moving the delivery catheter along the guidewire and introducing the delivery catheter into the thoracic aorta via arterial access, and (d) deploying the stent graft 1600, 1700 into the thoracic aorta.

In a twenty-third aspect, the invention provides a method for placement of a stent graft 1600, 1700 according to one of the twentieth or twenty-first aspects of the invention, comprising, (a) introducing a guidewire into an aortic arch via arterial access, (b) loading a delivery catheter containing a stent graft 1600, 1700 according to one of the twentieth or twenty-first aspects of the invention onto the guidewire, (c) moving the delivery catheter along the guidewire and introducing the delivery catheter into the aortic arch via arterial access, and (d) deploying the stent graft 1600, 1700 into a proximal descending aorta.

In a twenty-fourth aspect, as shown in FIG. 18, the invention provides a method for placement of a stent 1600, 1700 according to one of the twentieth or twenty-first aspects of the invention, comprising, (a) introducing a guidewire into an ascending aorta 1800 via arterial access, (b) loading a delivery catheter containing a stent graft 1600, 1700 according to one of the twentieth or twenty-first aspects of the invention onto the guidewire, (c) moving the delivery catheter along the guidewire and introducing the delivery catheter into the ascending aorta 1800 via arterial access, and (d) deploying the stent graft 1600, 1700 into the ascending aorta 1800.

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. The above embodiments and other embodiments may be combined as is apparent to those of skill in the art upon studying the above description, unless noted otherwise. For example, each of the aspects drawn to double-barreled stent grafts could be deployed within any of the debranching stent grafts. Likewise, any of the debranching stent graft limbs could be deployed within any of the debranching stent grafts. The scope of the present invention includes any other applications in which embodiment of the above structures and deployment methods are used. The scope of the embodiments of the present invention should be determined with reference to claims associated with these embodiments, along with the full scope of equivalents to which such claims are entitled.

As used herein, the singular forms "a," "an" and "the" include plural referents unless the context clearly dictates otherwise. "And" as used herein is interchangeably used with "or" unless expressly stated otherwise.

All embodiments within and between different aspects of the invention can be combined unless the context clearly dictates otherwise.

Example 1: Endovascular De-Branching of a Thoraco-Abdominal Aneurysm

The ultimate vascular procedure is the open repair of the Thoracic Abdominal Aneurysm (TAA). The undertaking of such a procedure, is a challenge for the surgeon, surgical team, the institution where these procedures are performed, but none of this compares to the challenge the patient and their family endures to recover from such an invasive procedure.

There have been several surgical approaches to this procedure. There are only a few sites in the country that can offer an open TAA repair with acceptable complication rates. A newer surgical approach is de-branching, with either concurrent or delayed stenting. This approach may have reduced many of the major complication rates but has its own other major complications. Any surgeon performing this surgery understands that this is a very arduous surgery and the patient has a very challenging recovery. A fenestrated stent grafting is newer, less invasive method for repair of the TAA. These custom made grafts are either constructed on the back table in the operating room or special order. These are technically very challenging cases that are performed at a select number of centers.

A minimally invasive debranching of the TAA via bilateral femoral and one axillary artery exposure was recently performed:

A visceral doublebarreled main body stent graft was constructed, with one barrel dedicated to stent the visceral segment, while the other barrel was dedicated to the revascularization of the infra-renal aorta.

A visceral graft was constructed by modifying a standard bifurcated stent graft.

Modifications were made to the ipsilateral and contralateral limbs of the stent graft. Two 6 mm self-expandable covered stents were sewn to the ipsilateral limb and two 7 mm self-expandable covered stents were sewn to the contralateral limb. The newly constructed debranching visceral stent graft was re-sheathed by constraining the debranching visceral stent graft with spirally wrapping wire around the stent graft's exterior.

The visceral double-barreled stent graft and debranching visceral stent graft were re-sheathed. The visceral double-barreled stent graft was then positioned and deployed within the thoracic aorta. The debranching visceral stent graft was then positioned and deployed within a lumen of the visceral double-barreled main body stent graft, with the distal point of the debranching visceral stent graft about 4 cm above the osteol of the celiac artery.

From an arm approach (axillary artery with a conduit), individual selection of each renal artery was possible from one of the two 6 mm covered stents. Covered extension stent grafts were deployed from the debranching visceral stent graft to each renal artery. The same technique was used for the superior mesenteric artery ("SMA") and celiac artery through the 7 mm stent graft off of the short leg of the debranching visceral stent graft. With the visceral segment de-branched, we extended the open barrel of the visceral double-barreled main body stent graft to an infra-renal position, and the remaining part of the surgery was a standard infra-renal endovascular aortic repair ("EVAR").

The advantage of such an approach allows a less invasive approach to a very challenging surgical problem. The present invention provides a much more versatile approach that can handle an almost infinite anatomic configurative without customized graft construction.

Example 2: Endovascular De-Branching of a Thoraco-Abdominal Aneurysm

Endovascular repair of infra-renal abdominal aneurysms has become an accepted alternative to traditional open surgical repair. These techniques allow for shorter hospital stays following a less invasive procedure and initially reduced morbidity and mortality in patients. However, endovascular repair using stent grafts has been slow to overtake open surgical repair as the standard treatment for thoracoabdominal aortic aneurysms (TAA) due to anatomical restrictions and the high cost of custom stent grafts to accommodate individual aneurysm cases. The case presented here represents a method of endoluminal repair of TAA.

With the patient under general anesthesia, standard groin and right axillary incisions were made, exposing the vessels. This allowed the right/left common femoral arteries to be accessed with a 5 French sheath and measuring pigtail catheter to allow for angiograms to be performed to define the patient's specific anatomy. At this point, two grafts were constructed. One was a visceral double-barreled main body stent graft and the other was a debranching visceral stent graft. The visceral double-barreled main body stent graft was constructed from a 100 mm thoracic stent graft by sewing a seam vertically up the graft for 70 mm, thus creating a double-barrel configuration. The debranching visceral stent graft was made from a standard main body bifurcated graft with two self-expanding covered stent grafts sewn to each limb; this created a total of four stents staggered two proximal and two distal to the ipsilateral and contralateral limbs. Once sewn, the debranching visceral stent graft was re-constrained using 20 gauge surgical wire and re-sheathed. During this process, care was taken to maintain the orientation markers.

The visceral double-barreled stent graft was placed approximately 11 cm above the celiac artery. The debranching visceral stent graft was then inserted through the lumen of one of the barrels of the visceral double barrel stent graft, with approximately 4-5 cm of overlap. The distal visceral limbs were placed 4 cm above the celiac artery to allow adequate room for cannulation of the visceral segment vessels.

A 10-mm Dacron graft was sewn as a conduit off the right axillary artery allowing access through a sheath to the descending aorta. The open barrel of the visceral double-barreled main body stent graft was selected for the pigtail catheter placement and eventually for the infrarenal segment. An 8-mm long French sheath was brought in from the axillary conduit. Through the individual limbs of the debranching visceral stent graft, the celiac, SMA, and renal arteries were stented. Upon stenting of four visceral arteries, the open barrel of the visceral double-barreled main body stent graft was extended to an infrarenal position using a straight thoracic stent graft. At this point, a standard infrarenal endoluminal abdominal aortic aneurysm repair was performed.

Throughout the procedure, the patients were heparinized and stent-graft contact points were angioplastied. Completion angiograms were performed and the right axillary conduit was oversewn. The patients were protected with a lumbar drain in the usual manner with special attention to adequate spinal perfusion via control of spinal fluid pressures and mean arterial pressures.

Following the procedure, the patients were transferred to the ICU for close monitoring with a spinal drain in place. The spinal drain remained in place for 48-72 hours and upon its removal the patients were advanced to normal activity. By the fourth day of the hospital stay, they were doing well, remained neurologically intact and were getting ready for discharge. One month follow up revealed the patients were doing well.

The conventional open thoracoabdominal approach for handling thoracoabdominal aneurysms is challenging for all involved including surgical staff, post-surgery nursing staff and especially the patients. Significant complications of the open approach can include paraplegia, renal failure, and death. This has led to the exploration and acceptance of other techniques.

Open debranching followed by either concurrent or delayed stent-grafting has been performed and been shown to be successful with some reduction in complication rates. However, these remain arduous surgeries for staff and patients with significant complications. Newer techniques using fenestrated grafts are on the horizon. Unfortunately, these newer methods are geared towards juxtarenal aneurysms. Classic thoracoabdominal aneurysms extending from the mid thoracic more distally are still seldom approachable endovascularly by current technologies.

In the cases above, a complete endo-debranching was performed, which demonstrates the application of a viable alternative which preserves visceral and infrarenal blood flow with minimal insult to the patient. The advantages of this approach are its versatility with regards to anatomical variations and its inherent redundancies with regard to dealing with challenges through the operative procedure.

Example 3: Endovascular De-Branching of a Thoracic Aneurysm

The patient is a 47-year-old female who presented with a symptomatic thoracic dissection with large thoracic aneurysm, type A dissection, with unfortunate significant aneurysmal changes throughout the entire length down into her iliac artery. Her visceral segment came off of a true lumen.

The patient was placed in a supine position and the neck, chest, arms, and groins were prepped and draped in a normal sterile manner. The left common, internal and external carotid arteries were dissected out with a longitudinal incision in a standard manner and circumferentially controlled. A longitudinal incision was made over the brachial artery and dissected down to the left brachial artery with circumferential control. A vertical incision was made in both the right and left groin, dissected down to the common femoral, deep femoral, and superficial femoral arteries with circumferential control. The focus then shifted to the patient's right side where a transverse supraclavicular incision was made and dissection was carried down to the subclavian artery which was exposed proximally and distally.

At this point, the patient was heparinized. A 10-mm conduit was sewn onto the subclavian artery in an end-to-side manner. Once the conduit had adequate hemostasis, access was gained to the right common femoral artery and left common femoral artery with a pigtail catheter placed up into the aortic arch, from right common femoral artery access. Wires and catheters were placed from the left brachial artery, as well as from the left common carotid artery. Care was taken to select true lumen with the dissection in the left common carotid artery. This was done with ultrasound guidance, and wires were placed in the ascending aorta from the access points.

With the wires in place, the focus shifted to the aortic arch double-barreled main body stent graft, which was created by modification of a 40-mm Valiant stent graft on the back table prior to induction. This aortic arch double-barreled main body stent graft was then positioned in the correct orientation from right subclavian artery access and deployed, with a guidewire in one of the double-barrel lumens. The deployment was performed with holding respirations and with rapid pacing. The right common femoral artery was then used as the access point to select the other double-barrel lumen of the stent graft.

From here, we once again moved back to the right subclavian artery access and positioned and deployed the debranching Great vessel stent graft. This stent graft was modified from a standard main body 20-mm graft on the back table prior to induction. The individual legs/limbs of the debranching Great vessel stent graft were then selected retrograde from the left common carotid artery and from the left subclavian artery.

Intravascular ultrasound ("IVUS") was introduced to verify correct lumen selection. The left subclavian access was in the incorrect lumen. So an Omni Flush catheter was used from the right subclavian artery to retrograde select the subclavian Viabahn branch in an up-and-over technique. From the left subclavian, this wire was then snared. In a through-and-through manner, a wire was passed into the dedicated 10-mm Viabahn limb of the debranching Great vessel stent graft. This was then confirmed with IVUS. iCAST 10-mm stents were then used to stent from the debranching Great vessel stent graft to the subclavian artery on the left side. This stent graft was smoothed out with a 14×60 self-expanding stent.

Then an 18×150 thoracic stent graft extender was brought from the right common femoral artery up and over a very steep aortic arch for placement. This pushed the aortic arch double-barreled main body stent graft (without a stent valve attached) down towards the coronary arteries. The patient remained stable through this process. Balloons were placed from both the arm and the groin into the double-barrel lumens and the main body. The aortic arch double-barreled main body stent graft was repositioned back up into the correct location. At this point, a 16×20×82 innominate stent graft was placed from the innominate portion of the debranching Great vessel stent graft into the innominate artery. This was extended with a 23-mm Gore cuff and demonstrated good blood flow. The position was then re-locked with the balloon in the proximal portion of this stent graft and the 18×150 thoracic stent graft extender was re-advanced and positioned in a lumen of the aortic arch double-barrel main body stent graft and through the aortic arch. An additional 30×150 stent graft extender was placed within the thoracic stent graft extender and contact points were angioplastied.

From here, the connection between the left common carotid and the debranching Great vessel stent graft was completed with 10 mm iCAST stent grafts. These were smoothed out with 12 and 14 mm self-expanding stents. The thoracic aortic arch was completely debranched with good flows and equal pressures in both artery lines, right and left.

Next an angiogram was performed on the infrarenal aorta. A dissection was identified into the left common iliac artery. This was then excluded using kissing 16 mm stent grafts extending from the distal aorta into the common iliac artery right to the internal iliac bilaterally, and these points were angioplastied with very good results, and dopplerable signals.

The catheter, wires, and sheaths were removed. The brachial artery on the left side was closed with interrupted 7-0 Prolenes. The left common carotid sheath site was closed with interrupted 6-0 Prolene. The right subclavian conduit was stapled off with an Endo GIA stapler. The groin artery sheaths were removed and these were closed with interrupted 4-0 Prolenes. With adequate hemostasis at all sites, the patient's heparinization was reversed.

The incisions were irrigated and closed in layers in a standard manner. The neck incision was reapproximated with running Vicryl and drains were placed in both neck incisions. The subclavian incision on the right side was also sewn with Vicryl, while the arm incision on left and the groin incisions were closed with staples.

Angiographic findings demonstrated a patent aortic arch, patent Great vessels with a very large dissection and aneurysmal changes. After stent grafting as described above, there was retained flow to the right innominate, the right common carotid, the left common carotid, the left subclavian, as well as the vertebral arteries. There was also retained flow to the descending aorta and the distal segment with retained flow to the lower extremity, common iliac arteries, internal and external iliac arteries. There was still faint filling of the dissection.

I claim:

1. A debranching stent graft comprising:
   a main body stent graft with a first bifurcation defining a first leg and a second leg, wherein the main body stent graft has a distal end and a proximal end, and wherein the second leg is longer than the first leg;
   a first visceral limb coupled to the first leg in a unitary configuration prior to in vivo deployment of the debranching stent graft, wherein the first visceral limb has a second bifurcation defining a third leg and a fourth leg; and
   a second visceral limb coupled to the second leg in a unitary configuration prior to in vivo deployment of the debranching stent graft, wherein the second visceral limb has a third bifurcation defining a fifth leg and a sixth leg.

2. The debranching stent graft of claim 1, wherein the second leg is at least 10 mm longer than the first leg.

3. The debranching stent graft of claim 1, wherein the first bifurcation occurs in the range from about 30 mm to about 40 mm from the proximal end.

4. The debranching stent graft of claim 1, wherein the second bifurcation occurs in the range from about 70 mm to about 90 mm from the proximal end of the main body stent graft.

5. The debranching stent graft of claim 1, wherein the third bifurcation occurs in the range from about 80 mm to about 100 mm from the proximal end of the main body stent graft.

6. The debranching stent graft of claim 1, wherein the second bifurcation occurs 70 mm from the proximal end of the main body stent graft and the third bifurcation occurs 80 mm from the proximal end of the main body stent graft.

7. The debranching stent graft of claim 1, wherein the first visceral limb has a length in the range from about 30 mm to about 50 mm.

8. The debranching stent graft of claim 1, wherein each of the third leg, the fourth leg, the fifth leg and the sixth leg have a diameter of about 7 mm.

9. The debranching stent graft of claim 1, wherein the second visceral limb has a length in the range from about 30 mm to about 50 mm.

10. The debranching stent graft of claim 1, wherein the second leg is no more than about 20 mm longer than the first leg.

11. The debranching stent graft of claim 1, wherein the first leg and the second leg each have a diameter in the range from about 14 mm to about 16 mm.

12. The debranching stent graft of claim 1, wherein the distance from the proximal end of the main body stent graft to the distal end of the first leg is in the range from about 70 mm to about 90 mm, and wherein the distance from the proximal end of the main body stent graft to the distal end of the second leg is in the range from about 80 mm to about 100 mm.

13. The debranching stent graft of claim 1, further comprising a radiopaque marker at a distal end of at least one of the third leg and the fourth leg, and a radiopaque marker at a distal end of at least one of the fifth leg and the sixth leg.

14. The debranching stent graft of claim 1, further comprising a radiopaque marker at a distal end of the third leg, and a radiopaque marker at a distal end of the fifth leg.

15. The debranching stent graft of claim 1, further comprising bi-directional anchoring hooks formed as part of two individual stents coupled to the proximal end of the main body stent graft.

16. The debranching stent graft of claim 1, further comprising a fixation stent coupled to the proximal end of the main body stent graft.

17. The debranching stent graft of claim 1, wherein a diameter of the third leg is equal to a diameter of the fourth leg, and wherein a diameter of the fifth leg is equal to a diameter of the sixth leg.

18. A method for placement of a debranching stent graft, the method comprising:
   introducing a guidewire into an aorta via arterial access;
   loading a delivery catheter containing the debranching stent graft according to claim 1 onto the guidewire;
   moving the delivery catheter along the guidewire and introducing the delivery catheter into the aorta via arterial access; and
   deploying the debranching stent graft into one of the aorta or a lumen of a previously placed stent graft within the aorta.

* * * * *